United States Patent [19]

Szucs

[11] 4,224,052
[45] Sep. 23, 1980

[54] POLYSUBSTITUTED BUTANOIC ACIDS, ESTERS AND DERIVATIVES THEREOF UTILIZING THE SAME AS HERBICIDES

[75] Inventor: Stephen S. Szucs, Trenton, N.J.

[73] Assignee: American Cyanamid Company, Stamford, Conn.

[21] Appl. No.: 903,379

[22] Filed: May 5, 1978

[51] Int. Cl.$^2$ .................... A01N 9/20; C07C 121/52
[52] U.S. Cl. .................................. 71/105; 260/465 D; 260/340.5 R; 71/88; 71/90; 71/94; 71/98; 546/270; 546/284; 546/330; 549/60; 549/76; 549/77
[58] Field of Search ...................... 71/105; 260/465 D

[56] References Cited

U.S. PATENT DOCUMENTS

| | | | |
|---|---|---|---|
| 2,394,916 | 2/1946 | Jones | 71/107 |
| 2,655,526 | 10/1953 | Cope | 260/465 D |
| 3,086,990 | 4/1963 | Reeve | 71/107 |
| 3,110,723 | 11/1963 | De Benneville et al. | 71/105 |
| 3,133,954 | 5/1964 | De Benneville et al. | 71/105 |
| 3,998,965 | 12/1976 | Gittos et al. | 260/465 D |

FOREIGN PATENT DOCUMENTS 1383366 11/1964 France .................................. 260/465 D

OTHER PUBLICATIONS

Gellert et al., "Diphenylpiperidines: Synthesis etc.", (1971), CA 74, No. 111875m.

*Primary Examiner*—Glennon H. Hollrah
*Attorney, Agent, or Firm*—Harry H. Kline

[57] ABSTRACT

There are provided polysubstituted butanoic acids, esters and derivatives thereof, methods for preparing the same and herbicidal compositions employing said polysubstituted butanoic acids, esters and derivatives.

46 Claims, No Drawings

POLYSUBSTITUTED BUTANOIC ACIDS, ESTERS AND DERIVATIVES THEREOF UTILIZING THE SAME AS HERBICIDES

The present invention relates to a method for the preemergence or postemergence control of undesirable monocotyledonous and dicotyledonous plant species by applying to the foliage and stems of said plants or to soil containing seeds or other propagating organs of said plants, a herbicidally effective amount of a compound of the formula:

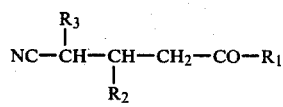

wherein $R_1$ is OH, $OR_4$, $NR_5R_6$ or OM; $R_2$ and $R_3$ each represent members selected from the group consisting of

pyridyl and thienyl; $R_4$ is alkyl $C_1$-$C_8$, monohaloalkyl $C_1$-$C_4$, hydroxyalkynyl $C_2$-$C_4$, monohaloalkynyl $C_3$-$C_4$, monohaloalkenyl $C_3$-$C_4$, alkoxy $C_1$-$C_4$ alkyl $C_1$-$C_4$; $R_5$ and $R_6$ each independently represent members selected from the group consisting of hydrogen and alkyl $C_1$-$C_2$; M is an alkali metal, ammonium, $C_1$-$C_8$ mono or di-alkylammonium or hydroxyethylammonium; and X and Y each independently represent a member selected from the group consisting of hydrogen, halogen (preferably F, Br or Cl); alkyl $C_1$-$C_4$, alkoxy $C_1$-$C_4$, $OCF_3$, $OCHF_2$, $CF_3$, CN, COOH, $NO_2$, OH, $SCH_3$, $NR_7R_8$ and $CH_3SO_2$, and when X and Y are taken together and joined to adjacent carbons of the benzene ring they can represent —$OCH_2O$— and $R_7$ and $R_8$ each represent hydrogen or alkyl $C_1$-$C_2$.

The instant invention also relates to a herbicidal composition comprising a herbicidally effective amount of a formula (I) polysubstituted butanoic acid, ester of derivative, hereinabove defined, in admixture with an inert, solid, water insoluble, diluent such as finely divided silica, kaolin, attapulgite, bentonite, montmorillonite, pumice, talc, fullers earth, diatomaceous earth, and the like. Still more particularly, the present invention relates to novel threo stereoisomers of formula (I), defined above. These novel stereoisomers, which are uniquely active as herbicidal agents, are depicted by the "sawhorse" projections shown herein below as mirror-image formulas (II) and (III):

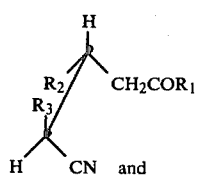

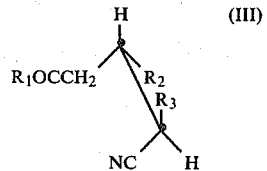

wherein $R_1$ is OH, OQ or $OR_4$; $R_2$ and $R_3$ each represent members selected from the group consisting of

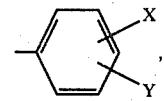

pyridyl and thienyl; $R_4$ i alkyl $C_1$-$C_8$, monohaloalkyl $C_1$-$C_4$, hydroxyalkynyl $C_2$-$C_4$; monohaloalkynyl $C_3$-$C_4$, monohaloalkenyl $C_3$-$C_4$ or alkoxy $C_1$-$C_4$ alkyl $C_1$-$C_4$; Q is ammonium, $C_1$-$C_8$ mono or dialkylammonium or hydroxyethylammonium; and X and Y each independently represent members selected from the group consisting of hydrogen, halogen (preferably F, Br or Cl), alkyl $C_1$-$C_4$, alkoxy $C_1$-$C_4$, $OCF_3$, $OCHF_2$, $CF_3$, CN, COOH, $NO_2$, OH, $SCH_3$, $NR_7R_8$ or $CH_3SO_2$, and when X and Y are taken together and joined to adjacent carbons of the benzene ring they can represent —$OCH_2O$—; $R_7$ and $R_8$ each represent hydrogen or alkyl $C_1$-$C_2$; provided that when $R_4$ is ethyl at least one of $R_2$ and $R_3$ is other than phenyl.

The hereinabove defined threo stereoisomers, namely formulas (II) and (III), are the (+) and (−) optical isomers which can be resolved by recrystallizations of the salt prepared from a mixture of the racemic acid and or appropriate optically active amine, such as (+)- or (−)-α-methylbenzylamine, in a 1:1 to 2:1 molar ratio of acid:amine. Liberation of the acids from the corresponding α-methylbenzylamine salts gives products having equal and opposite rotation. Thus, the resolution of the formula (II) or (III) threo acids yields the corresponding optically active (+)- or (−)-acid. Optical rotation has not been correlated with absolute configuration in this series.

Evaluation of the racemic modification, i.e. the threo (±) pair, the threo (−) isomer and the threo (+) isomer indicates that all are effective herbicidal agents. However, the threo (−) isomer is generally about twice as active as the 50/50 (±) threo pair and significantly more effective than the (+) threo isomer.

Illustrative of the $C_1$-$C_8$ alkyl substituents are: methyl, ethyl, n-propyl, isopropyl, n-butyl, t-butyl, sec-butyl, isobutyl, n-pentyl, n-hexyl, n-heptyl, n-octyl, 1-ethylbutyl, 2-ethylhexyl, 2-methylheptyl, 3-pentyl, 2-pentyl and 3-methylpentyl.

Exemplary halogen substituents are: chlorine, fluorine, bromine and iodine, chlorine, fluorine and bromine being preferred.

Illustrative pyridyl and thienyl substituents are: 2-pyridyl, 3-pyridyl, 4-pyridyl, 2-thienyl and 3-thienyl.

As is evident from the hereinabove defined structures and the definitions given for the several R groups utilized in describing the compounds of the present invention, a variety of structural isomers and stereoisomers are encompassed by the present invention.

Although it has been found that structural isomers within the parameters defined for formula (I) compounds generally show similarity in their herbicidal effectiveness against undesirable plant species, it has been surprisingly found that stereoisomers within the defined parameters usually exhibit marked differences in herbicidal activity against undesirable plant species. The magnitude of the differences obtained with related stereoisomers is quite significant and is demonstrated by the discovery that the threo isomers are frequently found to be as much as 100 to 250 times more effective than the corresponding erythro isomers.

Formula (I) compounds, as shown above, contain two distinct asymmetric carbon atoms in the molecule. Four stereoisomers result from the two possible arrangements of groups about the two distinct asymmetric carbon atoms.

In general, the relationship among the stereoisomers of formula (I) compounds can be illustrated by the following "saw-horse" projections:

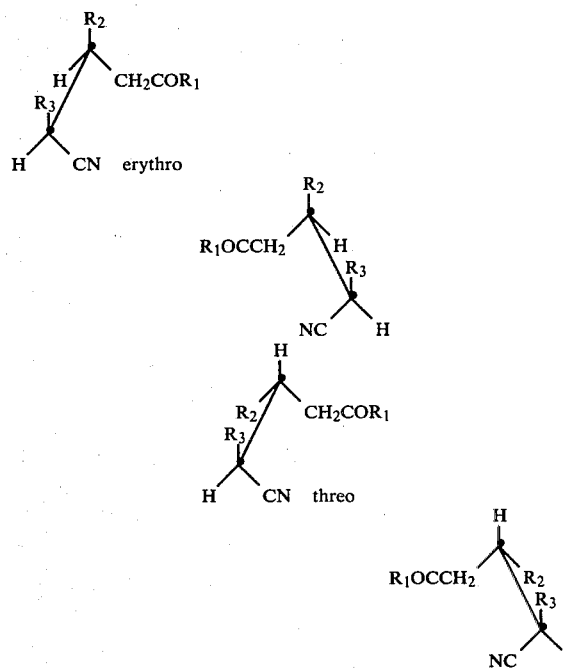

Stereoisomers A and B are non-superimposable mirror images, defined as enantiomers. The same is true for the relationship between C and D. Stereoisomers which are not mirror images of each other are referred to as diastereoisomers. Thus, A and/or B are diastereoisomers of both C and D. The erythro diastereoisomer is, by definition, the one in which at least two sets of identical or "similar" substituents on adjacent asymmetric carbons are side by side in one of its three eclipsed conformations as illustrated by A or B. The letters A through D are used instead of + and − since optical rotation has not been correlated with absolute configuration in this series. However, A and B are the (±) erythro pair, C and D are the (±) threo pair, respectively.

For purposes of the present invention and the sake of clarity in referring to the erythro and threo stereoisomers of formula (I), the substituents defined for $R_2$ and $R_3$ are considered "similar".

In practice, it has been found that the threo configuration of a given compound of the invention is generally markedly superior as a broad spectrum herbicidal agent to the corresponding erythro isomer. As such, threo compounds [formulas (II) and (III)] are especially useful for control of undesired vegetation along highways, railroad siding, rights-of-way under power transmission lines and along pipelines and/or wherever a high degree of control of undesired vegetation is required, as for example, in weed control programs for unseeded crop lands.

Preferred threo compounds useful for chemical fallow type control of undesired plants have the formula (II) or (III) configuration wherein $R_1$ is OH, OQ, or $OR_4$; $R_2$ is $C_6H_5$ and $R_3$ is $C_6H_5$, m-chlorophenyl, m-fluorophenyl, p-chlorophenyl, p-fluorophenyl or 3,5-dichlorophenyl; or $R_3$ is $C_6H_5$ and $R_2$ is m-nitrophenyl, m-trifluoromethylphenyl, m-fluorophenyl, m-bromophenyl, p-chlorophenyl, or p-fluorophenyl; or $R_2$ is p-chlorophenyl and $R_3$ is m-chlorophenyl; Q is ammonium, $C_1$–$C_8$ mono or di-alkylammonium or hydroxyethylammonium; and alkyl $C_1$–$C_8$.

Erythro-threo mixtures are similarly effective herbicidal compositions and have the advantage of selectivity in the presence of certain crops. Preferred erythro-threo mixtures which provide selective postemergence control of undesirable plant species in the presence of crops such as corn, barley and wheat, include:

erythro-threo 3-(m-Chlorophenyl)-4-cyano-4-phenylbutyric acid;

erythro-threo-4-Cyano-3,4-diphenylbutyric acid, dimethylamine salt;

erythro-threo-4-Cyano-3,4-diphenylbutyric acid, lithium salt;

erythro-threo-Ethyl 4-cyano-3-(3,5-dichlorophenyl)-4-phenylbutyrate;

erythro-threo-4-Cyano-4-(p-fluorophenyl)-3-phenylbutyric acid;

erythro-threo-4-Cyano-3-(p-fluorophenyl)-4-phenylbutyric acid;

erythro-threo-Ethyl 4-cyano-3-(p-fluorophenyl)-4-phenylbutyrate;

erythro-threo-Ethyl 4-cyano-3-(m-fluorophenyl)-4-phenylbutyrate;

erythro-threo-Ethyl 4-(m-chlorophenyl)-4-cyano-3-(2,4-dichlorophenyl)butyrate;

erythro-threo-3-(m-Bromophenyl)-4-cyano-4-phenylbutyric acid;

erythro-threo-Ethyl 4-cyano-3-(2,4-dichlorophenyl)-4-phenylbutyrate;

erythro-threo-4-Cyano-3-(m-fluorophenyl)-4-phenylbutyric acid;

erythro-threo-4-Cyano-4-[3,4-methylenedioxy)phenyl]-3-phenylbutyric acid;

erythro-threo-Ethyl 3-(3-chloro-4-fluorophenyl)-4-cyano-4-phenylbutyrate;

erythro-threo-Ethyl 4-cyano-4-(3,5-dichlorophenyl)-3-(m-nitrophenyl)butyrate;

erythro-threo-3-(m-Chlorophenyl)-4-cyano-4-phenylbutyric acid, dimethylamine salt;

erythro-threo-4-Cyano-3,4-diphenylbutyric acid, di-n-propylamine salt;

erythro-threo-4-Cyano-3,4-diphenylbutyric acid, di-isopropylamine salt;

erythro-threo-4-Cyano-3,4-diphenylbutyric acid, n-octylamine salt;

erythro-threo-4-Cyano-3,4-diphenylbutyric acid, ethylamine salt;

erythro-threo-4-Cyano-3,4-diphenylbutyric acid, 1,1,3,3-tetramethylbutylamine salt;

erythro-threo-3-(p-Chlorophenyl)-4-(m-chlorophenyl)-4-cyanobutyric acid;

erythro-threo-4-Cyano-3,4-diphenylbutyric acid;
erythro-threo-Ethyl-4-(m-chlorophenyl)-4-cyano-3-phenylbutyrate;
erythro-threo-4-(m-Chlorophenyl)-4-cyano-3-phenylbutyric acid;
erythro-threo-Methyl-4-cyano-3,4-diphenylbutyrate;
erythro-threo-Ethyl-4-cyano-3,4-diphenylbutyrate;
erythro-threo-Isopropyl-4-cyano-3,4-diphenylbutyrate;
erythro-threo-Ethyl-3-(m-chlorophenyl)-4-cyano-4-phenylbutyrate;
erythro-threo-2-Chloroallyl-4-cyano-3,4-diphenylbutyrate;
erythro-threo-4-Cyano-3-(3,4-dichlorophenyl)-4-phenylbutyric acid;
erythro-threo-2-Butoxyethyl-4-cyano-3,4-diphenylbutyrate; and
erythro-threo-4-Cyano-3-(m-cyanophenyl)-4-phenylbutyric acid.

Preferred erythro-threo preemergence herbicides selective in the presence of crops such as corn, cotton, soybeans, wheat and barley, include:
erythro-threo-Methyl 4-cyano-3,4-diphenylbutyrate;
erythro-threo-Ethyl 4-cyano-3,4-diphenylbutyrate;
erythro-threo-Isopropyl 4-cyano-3,4-diphenylbutyrate.
erythro-threo-Ethyl-4-(m-chlorophenyl)-4-cyano-3-phenylbutyrate;
erythro-threo-4-Cyano-3-(p-nitrophenyl)-4-phenylbutyric acid;
erythro-threo-Ethyl-4-cyano-3-(o-methoxyphenyl)-4-phenylbutyrate;
erythro-threo-4-Cyano-3-(3,4-dichlorophenyl)-4-phenylbutyric acid;
erythro-threo-Ethyl-3-(m-chlorophenyl)-4-cyano-4-phenylbutyrate;
erythro-threo-4-Cyano-3,4-diphenylbutyric acid, 2-aminoethanol salt;
erythro-threo-2-Chloroallyl-4-cyano-3,4-diphenylbutyrate;
erythro-threo-2-Butoxyethyl-4-cyano-3,4-diphenylbutyrate;
erythro-threo-3,4-bis(p-Chlorophenyl)-4-cyanobutyric acid;
erythro-threo-Ethyl-4-cyano-3-(m-methoxyphenyl)-4-phenylbutyrate;
erythro-threo-4-Hydroxy-2-butynyl-4-cyano-3,4-diphenylbutyrate;
erythro-threo-4-Chloro-2-butynyl-4-cyano-3,4-diphenylbutyrate;
erythro-threo-Ethyl-(4-(m-chlorophenyl)-4-cyano-3-(m-cyanophenyl)butyrate;
erythro-threo-Ethyl-4-cyano-3-(p-fluorophenyl)-4-phenylbutyrate;
erythro-threo-Cyano-3-(p-fluorophenyl)-4-phenylbutyric acid.

Erythro esters are primarily useful as intermediates for the preparation of threo and erythro-threo acids, but also appear to be involved in the improved selectivity found for erythro-threo mixtures.

In accordance with the process of the present invention, erythro esters and mixtures of erythro-threo esters of polysubstituted butanoic acid having the structure:

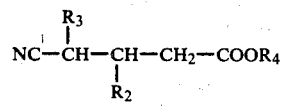

where $R_2$ and $R_3$ represent members selected from the group consisting of

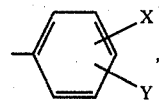

pyridyl and thienyl; $R_4$ is alkyl $C_1$-$C_8$, monohaloalkyl $C_1$-$C_4$, monohaloalkynyl $C_3$-$C_4$, monohaloalkenyl $C_3$-$C_4$, alkoxy $C_1$-$C_4$ alkyl $C_1$-$C_4$ or hdyroxyalkynyl $C_2$-$C_4$; and X and Y each independently represent members selected from the group consisting of hydrogen, halogen, alkyl $C_1$-$C_2$, $CF_3$, $OCF_3$, $OCHF_2$, alkoxy $C_1$-$C_2$, CN, COOH, $NO_2$, OH, $SCH_3$, $NR_7R_8$, and $CH_3SO_2$, or when X and Y are taken together and joined to adjacent carbon atoms they may represent —$OCH_2O$—; and $R_7$ and $R_8$ each represent hydrogen or alkyl $C_1$-$C_2$; can be prepared by reacting approximately equimolar amounts of the appropriate acetonitrile with the appropriate cinnamate in the presence of an alkali metal or alkaline earth metal base and an organic solvent at a temperature between about 0° C. and 50° C.

Among the preferred bases which may be employed are the hydroxides, $C_1$-$C_4$ alkoxides and phenoxides of sodium, potassium, or lithium.

Preferred organic solvents include $C_1$-$C_4$ aliphatic alcohols, dimethylsulfoxide and aromatic hydrocarbons, such as toluene and benzene.

The reaction may be graphically illustrated as follows:

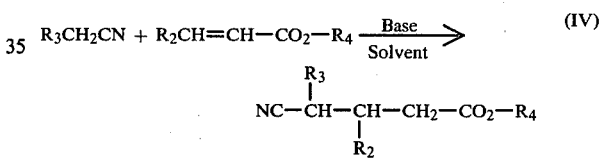

wherein $R_2$ and $R_3$ are as described above and $R_4$ is alkyl $C_1$-$C_8$. Alternatively, the formula (IV) esters can be prepared by conversion of a formula (IV) acid to the acid halide with thionyl halide and reaction thereof with a $C_1$-$C_8$ alkyl alcohol in the presence of a suitable base. These reactions yield mixtures of the erythro and threo stereoisomers which may be separated by differential solubility. As the threo isomer is almost invariably more soluble in most solvents than the corresponding erythro isomer, the erythro isomer is readily recovered substantially free of the threo isomer.

In practice, it has been found that esters of formula (IV), where $R_4$ is alkyl $C_1$-$C_8$ and $R_2$ and/or $R_3$ represent aminophenyl groups, can be readily prepared by the catalytic reduction of the corresponding nitrophenylester. These reactions are generally carried out by shaking in an atmosphere of hydrogen gas a reaction mixture comprising the nitrophenyl ester, a noble metal catalyst and an organic solvent.

Among the preferred catalysts useful in these reactions are platinum, platinum on carbon, platinum on silica, palladium, palladium on carbon and palladium on silica and the preferred solvents include lower aliphatic alcohols, ethyl acetate and acetic acid.

Preparation of formula (1) polysubstituted butyric acids can be obtained by reaction of an ester of formula (IV) with an alkali metal or alkaline earth metal base, preferably sodium or potassium hydroxide, sodium or potassium $C_1$–$C_4$ alkoxide or sodium or potassium phenoxide, in the presence of water and an organic solvent at a temperature ranging between about 25° C. and 100° C. The reaction yields a mixture of erythro and threo acids which may be separated by fractional crystallization using a solvent such as methanol, ethanol, chloroform, carbon tetrachloride, ethylene dichloride, methylene chloride, tetrahydrofuran, ether, dioxane, cyclohexanone or benzene.

The reaction is graphically illustrated below, using potassium hydroxide as the base and ethanol as the solvent.

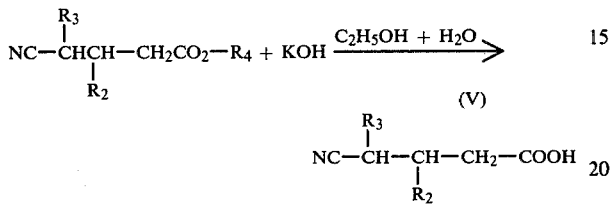

(V)

Fractional crystallization of the erythro-threo acid mixture, preferably from carbon tetrachloride, yields the erythro acid essentially free of the threo acid and likewise the threo acid substantially free of the erythro acid.

Treatment of the erythro-threo formula (V) acid mixture or the threo acid with ammonia, alkylamine, dialkylamine or amino alcohol, yields the amine salt corresponding to the formula (V) acid used. This reaction is preferably conducted at a temperature between 0° and 25° C. in the presence of a solvent such as diethyl ether.

Other salts of the formula (V) erythro-threo acids can be prepared in essentially the same manner as described for the amine and alkylamine salts, excepting that an alkali metal hydroxide is substituted for the ammonia, alkylamine, dialkylamine or amino alcohol hereinabove mentioned.

The compounds of the present invention are highly effective preemergence and postemergence herbicidal agents effective for the control of undesirable monocotyledonous and dicotyledonous plants.

In practice, the erythro-threo stereoisomeric mixtures are generally applied to the foliage and stems of undesirable plants or to soil containing seeds, seedlings or other propagating organs thereof, in admixture with an adjuvant and at a rate of application between about 0.035 and 11.2 kg per hectare of active ingredient.

The threo isomers are also generally applied in admixture with an adjuvant, usually an inert, solid, water insoluble diluent. However, rates of application as low as 0.018 kg per hectare may be employed for the preemergence or postemergence control of undesirable plants. While rates of application as high as 11.2 kg per hectare of the threo isomers can be used, generally it will not be necessary to exceed about 4.5 kg per hectare to achieve the weed control desired.

The polysubstituted butanoic acids, esters and derivatives of formulas (I), (II) and (III), are generally formulated as wettable powders, emulsifiable concentrates, or flowable (thixotrophic) concentrates which are usually dispersed in water or other inexpensive liquid diluent for application as a liquid spray. The above compounds may also be prepared as granular formulations containing, generally, about 10% to 15% by weight of toxicant.

Typically, a wettable powder can be prepared by grinding together about 25% to 80% by weight of a formula (I), (II) or (III) compound, about 2% to 15% by weight of a surfactant such as sodium N-methyl-N-oleoyl taurate, alkyl phenoxy polyoxyethylene ethanol, or sodium alkyl naphthalene sulfonate, and 18% to 65% by weight of a finely divided carrier such as kaolin, attapulgite, diatomaceous earth, or the like.

A typical formulation prepared in accordance with the above description can be defined as follows: 66% by weight of a formula (I), (II) or (III) toxicant, 10% by weight of sodium salt of sulfated nonylphenoxypoly(ethyleneoxy)ethanol, and 24% by weight of precipitated silica.

Advantageously, flowable (thixotropic) concentrates can be prepared by grinding together 40% to 60% by weight of a formula (I), (II) or (III) toxicant, 1% to 4% by weight of the sodium salt of condensed naphthalene sulfonic acids, 2% to 3% by weight of a gelling clay, 2% by weight of propylene glycol, and from 54% to 32% by weight of water.

A typical granular formulation can be prepared by dissolving or dispersing the active compound in a solvent and applying the toxicant to a sorptive of nonsorptive carrier such as attapulgite, corn cob grits, limestone, silica, montmorillonite, bentonite or the like.

A typical emulsifiable concentrate can be prepared by admixing 13% by weight of the formula (I), (II) or (III), compound with 6% by weight of a nonionic surfactant, such as a polyoxyethylene sorbitol ester, with 81% by weight of isophorone or 37% by weight of isophorone and 44% by weight of an aromatic petroleum distillate (B.P. 304°–330° F.) Sp.G. 15/56° C.=0.853–0.875.

The practice of the present invention and the practical limits thereof are further illustrated by the following examples.

EXAMPLE 1

Preparation of erythro-threo and erythro-Ethyl 4-Cyano-3,4-diphenylbutyrate

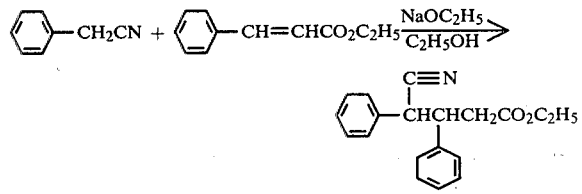

A solution of 46.9 g (0.40 mol) of benzyl cyanide and 70.5 g (0.40 mol) of ethyl cinnamate was added dropwise to a stirred solution of 3.37 g (0.147 g-atom) of sodium in 50 ml of absolute ethanol at room temperature. The solution was stirred for 15 hours at room temperature. The resulting cake was treated with saturated aqueous ammonium chloride and sufficient 10% hydrochloric acid to neutralize the base. The yellow solids containing the erythro-threo isomer mixture were collected, washed with water and ethanol, dried and recrystallized from 95% ethanol to yield 82.3 g (70.4%) of the erythro ester as white needles, m.p. 97°–98.5° C. The infrared and nmr spectra are in accord with the assigned structure. All of the esters originating from a substituted benzyl cyanide and/or a substituted ethyl cinnamate were prepared by a similar procedure and were purified by recrystallization, column chromatography on silica gel, or a combination of both.

Among the compounds prepared by the above procedure are:

erythro-threo-Ethyl 4-cyano-3-phenyl-4-o-tolylbutyrate, m.p. 60°-89° C., (another mixture had m.p. 88°-90°);

erythro-threo-Ethyl 4-(m-chlorophenyl)-4-cyano-3-phenylbutyrate, orange oil;

erythro-Ethyl 4-(p-chlorophenyl)-4-cyano-3-phenylbutyrate, m.p. 97°-99° C.;

erythro-Ethyl 4-cyano-4-(2,4-dichlorophenyl)-3-phenylbutyrate, m.p. 105°-107° C.;

erythro-threo-Ethyl 4-cyano-3-phenyl-4-(3-pyridyl)butyrate, yellow oil;

erythro-Methyl 4-cyano-3,4-diphenylbutyrate, m.p. 104°-106° C.;

erythro-threo-Ethyl 4-cyano-4-phenyl-3-p-tolylbutyrate, clear pink syrup;

erythro-Ethyl 4-cyano-4-phenyl-3-p-tolylbutyrate, m.p. 75°-76° C.;

erythro-Ethyl 4-cyano-3-(3,4-dichlorophenyl)-4-phenylbutyrate, 108.5°-113.5° C.;

erythro-Methyl 4-cyano-3-(p-nitrophenyl)-4-phenylbutyrate, m.p. 142°-142.5° C.;

erythro-threo-Ethyl 4-cyano-4-(p-nitrophenyl)-3-phenylbutyrate, m.p. 196°-202° C.;

erythro-Ethyl 4-cyano-4-(2,6-dichlorophenyl)-3-phenylbutyrate, m.p. 148.5°-149.5° C.;

erythro-threo-Methyl 4-cyano-3,4-diphenylbutyrate, m.p. 85°-99.5° C.;

erythro-threo-Ethyl 4-cyano-3,4-diphenylbutyrate, m.p. 79°-92° C.;

erythro-threo-Isopropyl 4-cyano-3,4-diphenylbutyrate, m.p. 85°-98° C.;

erythro-Ethyl 4-cyano-4-(3,5-dichlorophenyl)-3-phenylbutyrate, m.p. 99.5°-101.5° C.;

erythro-threo-Ethyl 3-(o-chlorophenyl)-4-cyano-4-phenylbutyrate, yellow oil;

erythro-threo-Ethyl 3-(p-chlorophenyl)-4-(m-chlorophenyl)-4-cyanobutyrate, yellow oil;

erythro-threo-Ethyl 3,4-bis(p-chlorophenyl)-4-cyanobutyrate, colorless oil;

erythro-threo-Ethyl 4-cyano-3-(m-methoxyphenyl)-4-phenylbutyrate, oily solid;

erythro-threo-Ethyl 4-(m-chlorophenyl)-4-cyano-3-(2,4-dichlorophenyl)butyrate, colorless oil;

erythro-threo-Ethyl 4-cyano-3-(p-fluorophenyl)-4-phenylbutyrate, white solid m.p. 81°-91° C.;

erythro-threo-Ethyl 4-(m-chlorophenyl)-4-cyano-3-(m-cyanophenyl)butyrate, yellow syrup;

erythro-threo-Ethyl 4-cyano-3-(2,4-dichlorophenyl)-4-phenylbutyrate, clear oil;

erythro-threo-Ethyl 4-cyano-3-(m-fluorophenyl)-4-phenylbutyrate, white solid, m.p. 88°-91° C.;

erythro-threo-Ethyl 4-cyano-3-(p-dimethylaminophenyl)-4-phenylbutyrate, light orange semi-solid;

erythro-threo-Ethyl 4-(o-chlorophenyl)-4-cyano-3-phenylbutyrate, yellow oil;

erythro-Ethyl 4-cyano-4-(p-methoxyphenyl)-3-phenylbutyrate, m.p. 93°-95° C.;

erythro-Ethyl 4-cyano-4-[3,4-(methylenedioxy)phenyl]-3-phenylbutyrate, m.p. 110°-112° C.;

erythro-threo-Ethyl 4-cyano-3-(3,4-difluorophenyl)-4-phenylbutyrate, yellow oily solid;

erythro-threo-Ethyl 3-(3-chloro-4-fluorophenyl)-4-cyano-4-phenylbutyrate, viscous oil;

erythro-threo-Ethyl 4-cyano-4-(3,5-dichlorophenyl)-3-(m-nitrophenyl)butyrate, m.p. 149°-157° C.;

erythro-threo-Ethyl 4-cyano-4-(3,5-dichlorophenyl)-3-(m-nitrophenyl)butyrate, m.p. 143°-146° C.;

erythro-threo-Ethyl 4-cyano-4-(o-fluorophenyl)-3-phenylbutyrate, pink oily solid;

erythro-Methyl 3-(m-chlorophenyl)-4-cyano-4-phenylbutyrate, m.p. 94°-98° C.

EXAMPLE 2

Preparation of erythro- and threo-4-Cyano-3,4-diphenylbutyric Acid and Separation of the erythro and threo

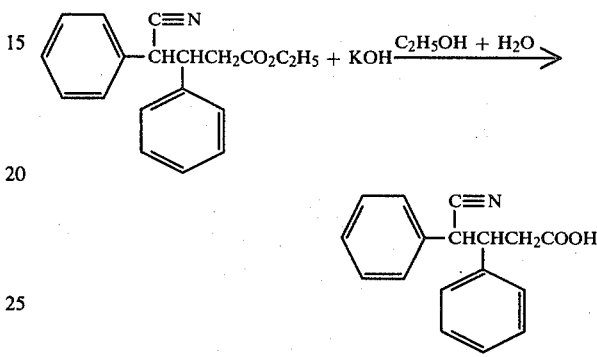

A solution of 15.0 g (0.229 mol) of 85.7% potassium hydroxide in 60 ml of 95% ethanol was added to a stirred solution of 50.0 g (0.170 mol) of erythro-ethyl 4-cyano-3,4-diphenylbutyrate in 500 ml of 95% ethanol at 65° C. The solution was stirred at 65°-68° C. for 0.5 hours, treated dropwise with 175 ml of water over a 0.75 hour period, and stirred for an additional hour at 65°-68° C. The mixture was cooled to 30° C., treated with an excess of glacial acetic acid, cooled to 5° C., and diluted with 1.25 liters of water. The white solids were collected, water washed, and dried to yield 38.1 g (84.2%) of product, m.p. 130°-148° C. The nmr spectrum and broad melting point range indicated that the product was a mixture of isomers. The isolation of each isomer was achieved by fractional crystallization from carbon tetrachloride.

erythro-4-Cyano-3,4-diphenylbutyric acid is characterized by its white needles and a m.p.=163.5°-165° C.

Analysis calculated for $C_{17}H_{15}NO_2$: C 76.96; H 5.70; N 5.28. Found: C 76.75; H 5.56; N 5.16.

threo-4-Cyano-3,4-diphenylbutyric acid is characterized by its white crystals and a m.p.=148°-149.5° C.

Analysis calculated for $C_{17}H_{15}NO_2$: C 76.96; H 5.70; N 5.28. Found: C 76.41; H 5.69; N 5.22.

Following the above procedure but employing the appropriate erythro or erythro-threo ester, yields the following 4-cyano-polysubstituted butyric acids:

erythro-threo-4-(p-Chlorophenyl)-4-cyano-3-phenylbutyric acid, m.p. 151°-164° C.;

erythro-threo-4-Cyano-4-(2,4-dichlorophenyl)-3-phenylbutyric acid, m.p. 64°-66° C.;

erythro-threo-4-Cyano-4-phenyl-3-p-tolylbutyric acid, m.p. 144°-149° C.;

erythro-threo-4-(m-Chlorophenyl)-4-cyano-3-phenylbutyric acid, m.p. 104°-144° C.;

erythro-threo-4-Cyano-3-phenyl-4-o-tolylbutyric acid, m.p. 127.5°-138° C.;

erythro-threo-4-Cyano-3-phenyl-4-(3-pyridyl)butyric acid, m.p. 148.5°-168° C.;

erythro-threo-4-Cyano-3-(p-nitrophenyl)-4-phenylbutyric acid, m.p. 196°-202° C.;
erythro-threo-4-Cyano-3-(3,4-dichlorophenyl)-4-phenylbentyric acid, m.p. 143°-154.5° C.;
erythro-threo-4-Cyano-3-(m-nitrophenyl)-4-phenylbutyric acid, m.p. 152°-156° C.;
erythro-threo-4-Cyano-3-(2,6-dichlorophenyl)-4-phenylbutyric acid, m.p. 167°-178° C.;
erythro-4-Cyano-3-phenyl-4-m-tolylbutyric acid, m.p. 149.5°-152.0° C.;
erythro-threo-4-Cyano-3-phenyl-4-m-tolylbutyric acid, m.p. 114°-129° C.;
erythro-threo-3-(m-Chlorophenyl)-4-cyano-4-phenylbutyric acid, m.p. 112°-120° C.;
erythro-threo-4-Cyano-3-(o-methoxyphenyl)-4-phenylbutyric yellow gum;
erythro-threo-3-(p-Chlorophenyl)-4-cyano-4-phenylbutyric acid, m.p. 168°-174° C.;
erythro-3-(p-Chlorophenyl)-4-cyano-4-phenylbutyric acid, m.p. 158°-164° C.;
erythro-4-Cyano-4-phenyl-3-($\alpha,\alpha,\alpha$-trifluoro-m-tolyl)butyric acid, m.p. 142°-151° C.;
erythro-threo-3-(o-Chlorophenyl)-4-cyano-4-phenylbutyric acid, m.p. 120°-128° C.;
erythro-threo-4-Cyano-4-phenyl-3-($\alpha,\alpha,\alpha$-trifluoro-m-tolyl)butyric acid, clear glass;
erythro-threo-3-(p-Chlorophenyl)-4-(m-chlorophenyl)-4-cyanobutyric acid, m.p. 161°-169° C.;
erythro-threo-4-Cyano-4-(3,5-dichlorophenyl)-3-phenylbutyric acid, m.p. 117.5°-147° C.;
erythro-threo-4-Cyano-4-(p-fluorophenyl)-3-phenylbutyric acid, m.p. 129°-137° C.;
erythro-threo-3,4-bis(p-Chlorophenyl)-4-cyanobutyric acid, m.p. 136°-159° C.;
erythro-threo-4-Cyano-3-(m-methoxyphenyl)-4-phenylbutyric acid, m.p. 249°-251° C.;
erythro-threo-4-Cyano-4-(3,4-dichlorophenyl)-3-phenylbutyric acid, m.p. 132°-156° C.;
erythro-threo-4-Cyano-3-(p-fluorophenyl)-4-phenylbutyric acid, m.p. 148°-167° C.;
erythro-threo-4-(m-Chlorophenyl)-4-cyano-3-(2,4-dichlorophenyl)butyric acid, m.p. 130°-159° C.;
erythro-threo-4-Cyano-3-(m-cyanophenyl)-4-phenylbutyric acid, colorless liquid;
erythro-threo-3-(m-Bromophenyl)-4-cyano-4-phenylbutyric acid;
erythro-threo-4-Cyano-3-phenyl-4-p-tolylbutyric acid;
erythro-threo-4-Cyano-3-(m-fluorophenyl)-4-phenylbutyric acid.
erythro-threo-4-Cyano-4-(3,5-dichlorophenyl)-3-(m-nitrophenyl)butyric acid, m.p. 62°-68° C.;
erythro-threo-4-Cyano-3-[p-(dimethylamino)phenyl]-4-phenylbutryic acid, m.p. 185°-194° C.;
erythro-threo-4-Cyano-3-(3,4-difluorophenyl)-4-phenylbutyric acid, m.p. 125°-146° C.;
erythro-threo-4-(o-Chlorophenyl)-4-cyano-3-phenylbutyric acid, m.p. 90°-110° C.;
erythro-threo-4-Cyano-4-[3,4-(methylenedioxy)phenyl]butyric acid, m.p. 151°-178° C.;
erythro-threo-4-Cyano-4-(p-methoxyphenyl)-3-phenylbutyric acid, m.p. 150°-188° C.;
erythro-threo-3-(3-Chloro-4-fluorophenyl)-4-cyano-4-phenylbutyric acid, yellow foam;
erythro-threo-4-Cyano-4-(o-fluorophenyl)-3-phenylbutyric acid, pink oily solid.

EXAMPLE 3

Preparation of threo-Ethyl 4-Cyano-3,4-diphenylbutyrate

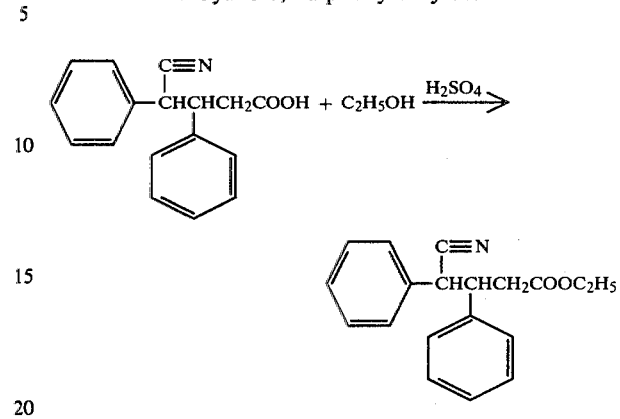

A suspension of 60.0 g (0.226 mol) threo-4-cyano-3,4-diphenylbutyric acid and 0.46 g of concentrated sulfuric acid in 400 ml absolute ethanol was heated to reflux for 26 hours in a flask fitted with a Soxhlet extractor containing 35 g 3 A molecular sieves. The mixture was stripped to a yellow syrup, diluted with 250 ml ether and filtered. The filtrate was diluted with 500 ml ether, shaken with 1% aqueous potassium hydrogen carbonate, washed with $H_2O$, and stirred over magnesium sulfate. The filtered solution was stripped to a syrup which crystallized. The white solid obtained after drying weighed 63.1 g (95%), m.p. 60.5°-63°, 59° (sinter).

Following the above procedure of Example 1, the following compounds were isolated after purification by column chromatography on silica gel and recrystalized when necessary:

threo-Ethyl 4-(m-chlorophenyl)-4-cyano-3-phenylbutyrate, m.p. 68°-69.5° C.;
threo-Ethyl 4-cyano-4-(o-nitrophenyl)-3-phenylbutyrate, brown oil;
threo-Ethyl 4-cyano-3-(m-nitrophenyl)-4-phenylbutyrate, yellow syrup;
threo-Ethyl 4-cyano-3-(m-cyanophenyl)-4-phenylbutyrate, clear oil;
threo-Ethyl 3-(m-bromophenyl)-4-cyano-4-phenylbutyrate, yellow oil;
threo-Ethyl 4-cyano-4-phenyl-3-($\alpha,\alpha,\alpha$-trifluoro-m-tolyl)butyrate, syrup;
threo-Ethyl 4-cyano-4-(3,5-dichlorophenyl)-3-phenylbutyrate, m.p. 109°-111.5° C.;
threo-Ethyl 3-(p-chlorophenyl)-4-(m-chlorophenyl)-4-cyanobutyrate, yellow oil;
threo-Ethyl 4-Cyano-4-(2,6-dichlorophenyl)-3-phenylbutyrate, m.p. 91°-95.5° C.;

EXAMPLE 4

Preparation of 4-Cyano-3,4-diphenylbutyryl Chloride

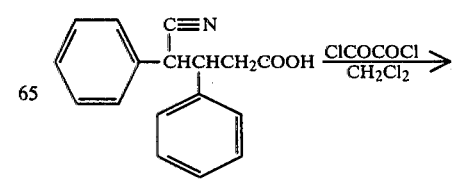

-continued

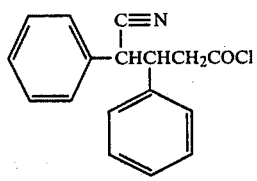

A suspension of 10.0 g (0.038 mol) of 4-cyano-3,4-diphenylbutyric acid in 100 ml of methylene chloride and 9.57 g (0.075 mol) of oxalyl chloride was heated to reflux under a nitrogen atmosphere for 5.5 hours. The reaction mixture was stripped, dissolved in 10 ml of benzene, and stripped again to yield 10.7 g of the acid chloride.

The acid chloride obtained by this procedure was used as an intermediate in preparing several esters and amides.

EXAMPLE 5

Preparation of 4-Hydroxy-2-butynyl 4-Cyano-3,4-diphenylbutyrate

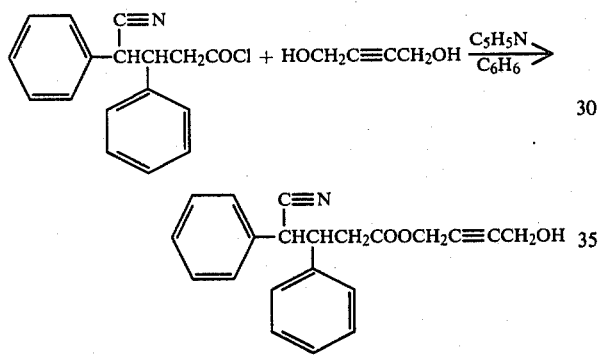

A solution of 10.7 g (0.038 mol) of 4-cyano-3,4-diphenylbutyryl chloride in 30 ml of benzene was added over a 45 minute period to a stirred solution of 6.5 g (0.076 mol) of 2-butyn-1,4-diol and 3.4 ml of pyridine in 100 ml of THF at 0°. The reaction mixture was stirred for 24 hours at room temperature in a flask equipped with a Drierite tube. The solution was poured into 50 ml of water and the layers were separated. Two 60-ml ether extractions of the aqueous layer were combined with the THF layer, were washed twice with 100 ml of H₂O, with 100 ml saturated aqueous sodium bicarbonate, and with 100 ml saturated aqueous sodium chloride and were stirred over MgSO₄. The filtered solution was stripped and purified by column chromatography on silica gel (hexanes/methylene chloride) to give two fractions weighing 12.6 g (47%) having different isomer ratios as determined from the nmr spectra. The infrared and nmr spectra are in accord with the assigned structure.

erythro-4-Hydroxy-2-butynyl 4-cyano-3,4-diphenylbutyrate, Colorless oil.

Analysis calculated for $C_{21}H_{19}NO_3$: C 75.66; H 5.75; N 4.20. Found: C 73.54; H 5.68; N 4.61.

erythro-threo-4-Hydroxy-2-butynyl 4-cyano-3,4-diphenylbutyrate, Colorless oil.

Analysis calculated for $C_{21}H_{19}NO_3$: C 75.66; H 5.75; N 4.20. Found: C 74.65; H 5.74; N 4.24.

The following amide and esters were prepared using a similar procedure:

threo-Octyl 4-cyano-3,4-diphenylbutyrate, clear oil;

erythro-threo-2-Butoxyethyl 4-cyano-3,4-diphenylbutyrate, m.p. 45°–50° C.;

erythro-threo-2-Chloroallyl 4-cyano-3,4-diphenylbutyrate, colorless oily solid;

erythro-threo-4-Cyano-N,N-dimethyl-3,4-diphenylbutyramide, clear sticky solid.

EXAMPLE 6

Preparation of 4-Chloro-2-butynyl 4-Cyano-3,4-diphenylbutyrate

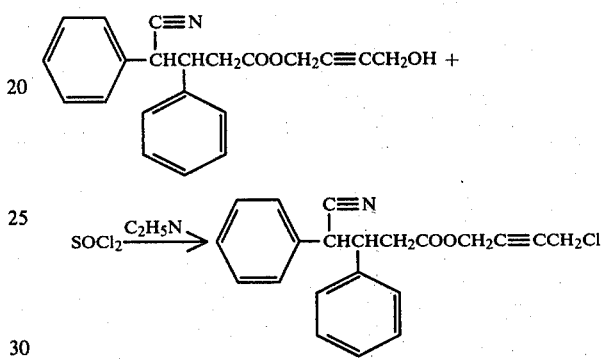

Thionyl chloride (3.56 g, 30.0 mmol) was added via syringe over a 5 min period to a stirred solution of 8.00 g (24.0 mmol) of 4-hydroxy-2-butynyl 4-cyano-3,4-diphenylbutyrate in 2.4 ml of pyridine at 0°. The reaction mixture was stirred at room temperature for 2 hours in a flask equipped with a Drierite tube. The mixture was diluted with 40 ml of ether and 100 ml of methylene chloride and was washed sequentially with 40 ml of hydrochloric acid, 40 ml of saturated aqueous sodium bicarbonate, three 40-ml portions of water and 40 ml of saturated aqueous sodium chloride. The organic phase was dried (MgSO₄), filtered, stripped and purified by column chromatography on silica gel (hexanes/methylene chloride) to yield 2.11 g (25%) of the title compound. The infrared and nmr spectra are in accord with the assigned structure.

erythro-threo 4-chloro-2-butynyl 4-cyano-3,4-diphenylbutyrate, Colorless oil.

Analysis calculated for $C_{21}H_{18}ClNO_2$: C 71.69; H 5.16; N 3.98; Cl 10.08. Found: C 70.87; H 5.17; N 3.78; Cl 10.96.

EXAMPLE 7

Preparation of Lithium Salt of erythro- and threo-4-Cyano-3,4-diphenylbutyric Acid

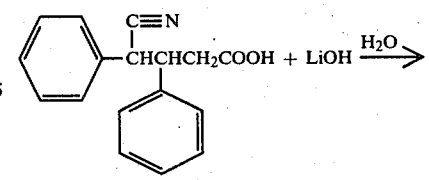

-continued

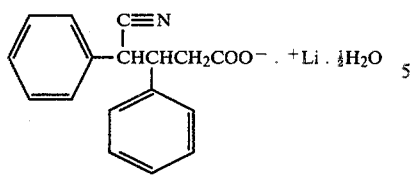

The lithium salt was obtained in 97% yield using the procedure described for the preparation of the sodium salt described in Example 10 below and has a melting point 266°–270° (decomp). The infrared and nmr spectra are in accord with the assigned structure.

Analysis calculated for $NO_2C_{17}H_{14}Li.\frac{1}{2}H_2O$: C 72.86; H 5.40; N 5.00. Found: C 73.41; H 5.67; N 5.06.

EXAMPLE 8

Preparation of Dimethylamine Salt of erythro- and threo-4-Cyano-3,4-Diphenylbutyric Acid

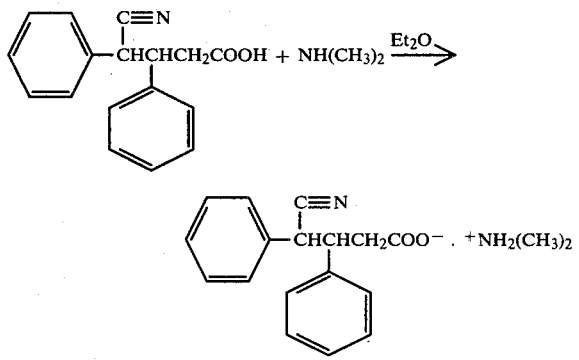

Dimethylamine was bubbled over a 45 minute period into a stirred solution of 2.40 g (9.05 mmol) of erythro- and threo-4-cyano-3,4-diphenylbutyric acid in 180 ml of anhydrous diethyl ether chilled in an ice bath. The resulting white suspension with stirred an additional 45 minutes and cooled in a dry ice-acetone bath. The white solids were collected, washed with ether and dried to yield 2.58 g (91.9%), m.p. 109°–118°. The infrared and nmr spectra are in accord with the assigned structure.

Analysis calculated for $C_{19}H_{22}N_2O_2$: C 73.52; H 7.14; N 9.02. Found: C 73.43; H 7.07; N 8.53.

Following the above procedure but substituting the appropriate amine for dimethylamine, yields the following compounds:
erythro-threo-Methylamine salt of 4-cyano-3,4-diphenylbutyric acid, m.p. 135°–147° C.;
threo-Ammonium salt of 4-cyano-3,4-diphenylbutyric acid, m.p. 118°–137° C.;
erythro-threo-Ethylamine salt of 4-cyano-3,4-diphenylbutyric acid, m.p. 143°–156° C.; and
erythro-threo-Dimethylamine salt of 3-(m-chlorophenyl)-4-cyano-4-phenylbutyric acid, m.p. 108°–119° C.

EXAMPLE 9

Preparation of Ethanolamine Salt of erythro- and threo-4-Cyano-3,4-Diphenylbutyric Acid

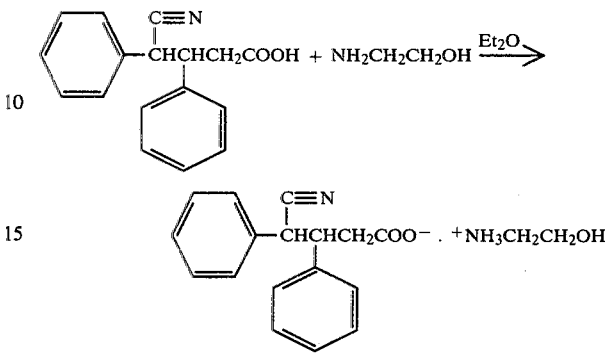

A mixture of 0.55 g (9.0 mmol) of 2-aminoethanol in 5 ml anhydrous ether and 1.5 ml absolute ethanol was added over a 10 minute period to a stirred solution of 2.40 g (9.04 mmol) of erythro- and threo-4-cyano-3,4-diphenylbutyric acid in 185 ml of anhydrous ether cooled in an ice bath. The resulting suspension was stirred at room temperature for 21 hours and chilled in a dry ice-acetone bath. The white solids were collected, washed with ether and dried to yield 2.70 g (91.4%), m.p. 132°–136° C. The infrared and nmr spectra are in accord with the assigned structure.

Analysis calculated for $C_{19}H_{22}N_2O_3$: C 69.92; H 6.79; N 8.58. Found: C 70.35; H 7.02; N 8.48.

Following the above procedure, but substituting the appropriate amine for ethanolamine, yields the following compounds:
erythro-threo-Dipropylamine salt of 4-cyano-3,4-diphenylbutyric acid, m.p. 120°–126° C.;
erythro-threo-Diisopropylamine salt of 4-cyano-3,4-diphenylbutyric acid, m.p. 130°–140° C.;
erythro-threo-Octylamine salt of 4-cyano-3,4-diphenylbutyric acid, m.p. 124°–130° C.

EXAMPLE 10

Preparation of Sodium Salt of erythro- and threo-4-Cyano-3,4-diphenylbutyric Acid

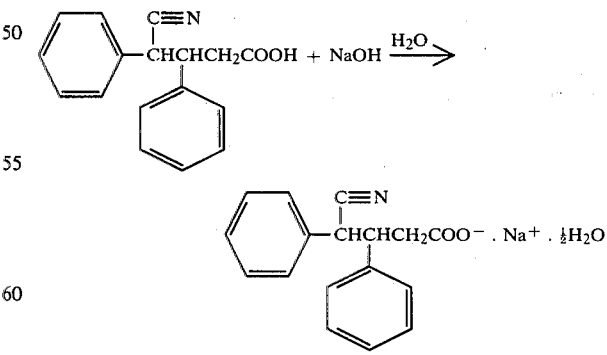

To a suspension of 2.48 g (9.35 mmol) of erythro- and threo-4-cyano-3,4-diphenylbutyric acid in 50 ml $H_2O$ stirred in an ice bath was added dropwise a solution of 0.38 g (9.2 equiv.) sodium hydroxide in 5 ml $H_2O$. The acid gradually dissolved after stirring at room temperature for 12 hours. The mixture was filtered, stripped and dried to yield 2.52 g (93.8%) of a white solid, m.p. 252°–257° C., 222° (sinter). The infrared and nmr spectra are in accord with the assigned structure.

Analysis calculated for $C_{17}H_{14}NO_2Na \cdot \frac{1}{2}H_2O$: C68.91; H 5.10; N 4.73. Found: C 69.52; H 5.28; N 4.80.

EXAMPLE 11

Preparation of Dimethylamine Salt of threo-4-Cyano-3,4-Diphenylbutyric Acid

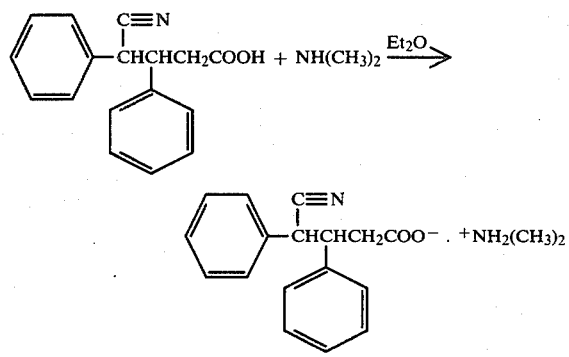

The dimethylamine salt of the threo-butyric acid was obtained in 90% yield using a procedure similar to that described for the preparation of the erythro-threo-salt in Example 8. The white powder has a melting point 102°–116° (bubbles), 94° (softening). The infrared spectrum is in accord with the assigned structure and the nmr spectrum indicates that no appreciable epimerization had occurred.

A solution of 0.48 g of the dimethylamine salt of threo-4-cyano-3,4-diphenylbutyric acid in 1.00 g of deionized water was kept in a stoppered vial for 50 days at room temperature (17°–22° C.) A 0.20 ml sample was diluted with 4 ml deionized water, acidified with 10% HCl to pH 1, and stirred at room temperature for 20 hours. The white solids were collected and dried in vacuo for 50 hours at 40°–45° C. The nmr spectrum indicated that no significant isomerization has occurred over the 50-day period.

EXAMPLE 12

Preparation of (−)-α-Methylbenzylamine Salt of (−)-threo-4-cyano-3,4-diphenylbutyric acid A mixture of 12.5 g (47.1 mmol) of threo-4-cyano-3,4-diphenylbutyric acid and 2.88 g (23.8 mmol) (−)-α-methylbenzylamine in 50 ml of absolute ethanol was heated to reflux and cooled slowly to room temperature. Crystallization yielded 3.49 g (19.2% from acid) of the (−)-α-methylbenzylamine salt [α] = −0.73°. Recrystallization from 18 ml of absolute ethanol give 2.41 g (13.2% from acid) of (−)-α-methylbenzylamine salt, [α] = −0.80°.

EXAMPLE 13

Preparation of (−)-threo-4-Cyano-3,4-diphenylbutyric Acid

A stirred suspension of 2.42 g (6.26) mmol of the (−)-α-methylbenzylamine salt of (−)-threo-4-cyano-3,4-diphenylbutyric acid in 38 ml of water was treated dropwise with 11 ml of 10% hydrochloric acid. The mixture was stirred at room temperature overnight. White solids were collected and dried in vacuo at 40° to give 1.52 g (91.5%) with [α] = −3.05°, m.p. 140°–142°.

88% (−)-threo from the F-19 nmr spectrum of the D-α-(trifluoromethyl)benzyl ester.

EXAMPLE 14

Preparation of (+)-threo-4-Cyano-3,4-diphenylbutyric acid

The procedure of Example 13 is repeated but the (+)-α-methylbenzylamine salt of (+)-threo-4-cyano-3,4-diphenylbutyric acid is substituted for (−)-α-methylbenzylamine salt of (−)-threo-4-cyano-3,4-diphenylbutyric acid. The reaction yields the above-named product in 96.3% yield with [α] = +3.04°, m.p. 139.5–142°, 88% (+)-threo determined as in Example 13.

EXAMPLE 15

Preemergence Herbicidal Activity

The preemergence herbicidal activity of the compounds of the present invention is exemplified by the following tests in which the seeds or propagating organs of a variety of monocotyledonous and dicotyledonous plants are separately mixed with potting soil and planted on top of approximately 2.5 cm of soil in separate cups. After planting, the cups are sprayed with the selected aqueous acetone solution containing test compound in sufficient quantity to provide the equivalent of about 0.13 kg to 11.2 kg per hectare of test compound per cup. The treated cups are then placed on greenhouse benches, watered and cared for in accordance with conventional greenhouse procedures. Three to five weeks after treatment, the tests are terminated and each cup is examined and rated according to the rating system provided below. The data obtained are reported in Table I below.

| Rating System | | |
|---|---|---|
| Rating | Meaning | % Control (compared to Check) |
| 0 | No effect | 0 |
| 1 | Trace effect | 1–5 |
| 2 | Slight effect | 6–15 |
| 3 | Moderate effect | 16–29 |
| 4 | Injury | 30–44 |
| 5 | Definite injury | 45–64 |
| 6 | Herbicidal effect | 65–79 |
| 7 | Good herbicidal effect | 80–90 |
| 8 | Approaching complete kill | 91–99 |
| 9 | Complete kill | 100 |

*Based on visual determination of stand, size, vigor, chlorosis, growth malformation and over-all plant appearance.

Plant Abbreviations, common name and scientific name
PN—Nutsedge (*Cyperus rotundus*)
SE—Sesbania (*Sesbania exaltata*)
LA—Lambsquarters (*Chenopodium album*)
MU—Mustard (*Brassica kaber*)
PI—Pigweed (*Amaranthus retroflexus*)
RW—Ragweed (*Ambrosia artemisiifolia*)
MG—Morningglory (*Ipomoea purpurea*) and (*Ipomea hederacea*)
BA—Barnyardgrass (*Echinochloa crusgalli*)
CR—Crabgrass (*Digitaria sanguinalis*)
FO—Green Foxtail (*Setaria viridis*)
WO—Wild Oats (*Avena fatua*)
TB—Tartary Buckwheat (*Fagopyrum tartaricum*)
VL—Velvetleaf (*Abutilon theophrasti*)

DB—Downy Brome (*Bromus tectorum*)
CH—Cheat (*Bromus secalinus*)
CG—Canarygrass (*Phalaris minor*)
CN—Corn (*Zea mays*)
SY—Soybean (*Glycine max*)

AN—Spring Wheat, Anza (*Triticum durum*)
NG—Winter Wheat, Nugaines (*Triticum aestivum*)
ER—Spring Wheat, Era (*Triticum aestivum*)
BB—Winter Wheat, Blueboy (*Triticum aestivum*)
ST—Barley, Steptoe (*Hordeum vulgare*)
BG—Blackgrass (*Alopecurus myosuroides*)

TABLE I

Preemergence Herbicidal Activity of Polysubstituted Acids and Derivatives having the Formula:

$$N\equiv C-CH-CH-CH_2-CO-R_1$$
$$\phantom{N\equiv C-}|\phantom{CH-}|$$
$$\phantom{N\equiv C-}R_3\phantom{H}R_2$$

| Structure | Rate kg/ha | PN | SE | LA | MU | PI | RW | MG | VL | TB | BA | CR | FO | WO | DB | CH | CG | CN | SY | AN | NG | ER | BB | ST |
|---|---|---|---|---|---|---|---|---|---|---|---|---|---|---|---|---|---|---|---|---|---|---|---|---|
| *R₁ = OH | 4.48 | 7 | 8.5 | 8 | 8.3 | 8.3 | 5.3 | 8 | 8.7 | — | 9 | 3.3 | 9 | 9 | 0 | — | — | 5.6 | 6.3 | — | — | — | — | — |
| R₂ = Phenyl | 2.24 | 5.9 | — | — | 7.9 | 5.6 | 1.7 | 5.9 | 8.2 | 6.2 | 7.9 | 0 | 8.5 | 8.6 | 0 | — | — | 2 | 4 | 4.7 | 3.2 | 2 | 2.5 | 6.5 |
| R₃ = Phenyl | 1.12 | 3.1 | 8 | 6.3 | 7.3 | 2.6 | 0 | 2.8 | 7.5 | 3.3 | 7.7 | 0 | 8.1 | 7.6 | 0 | — | — | 1.5 | 3.0 | 1.5 | 2.0 | 1.2 | 1.1 | 5.8 |
| E + T | 0.56 | 1.3 | 6 | 4.5 | 4.7 | 1.0 | 0 | 1.4 | 4.3 | 1.7 | 4.6 | 0 | 6.8 | 5.6 | 0 | — | — | 0.4 | 1.0 | 0 | 1.0 | 0.6 | 0 | 3.0 |
| (67/33) | | | | | | | | | | | | | | | | | | | | | | | | | |
| *R₁ = OH | 1.12 | 9 | 9 | 9 | 8.5 | 8 | 3 | 6.5 | 8 | 6 | 9 | 0 | 7 | 9 | — | — | — | 6 | 8 | 8 | 7 | — | — | 9 |
| R₂ = Phenyl | 0.56 | 3 | 7 | 9 | 8.5 | 6 | 3 | 4.5 | 7 | 0 | 9 | 0 | 7 | 9 | — | — | — | 0 | 7 | 2 | 3 | — | — | 7 |
| R₃ = Phenyl | 0.28 | 3 | 7 | 2 | 1.0 | 0 | 0 | 0 | 7 | 0 | 7 | 0 | 6 | 7 | — | — | — | 0 | 5 | 2 | 0 | — | — | 2 |
| T | 0.14 | — | — | — | 0 | — | — | 0 | 3 | 0 | 5 | — | 5 | 7 | — | — | — | 0 | 5 | 0 | 0 | — | — | 0 |
| (5/95) | | | | | | | | | | | | | | | | | | | | | | | | | |
| R₁ = OH | 4.48 | 0 | 8 | — | 9 | 9 | 0 | 8 | 8 | — | 9 | 9 | 9 | 7 | — | — | — | 6 | 5 | — | — | — | — | — |
| R₂ = Phenyl | 1.12 | 0 | 0 | — | 8 | 8 | 0 | 3 | 0 | — | 8 | 6 | 7 | 2 | — | — | — | 5 | 2 | — | — | — | — | — |
| R₃ = 4-Chlorophenyl | | | | | | | | | | | | | | | | | | | | | | | | | |
| E + T | | | | | | | | | | | | | | | | | | | | | | | | | |
| R₁ = OH | 11.2 | 1 | 9 | — | 9 | 9 | 6 | 0 | 5 | — | 7 | 6 | 8 | 5 | — | — | — | — | — | — | — | — | — | — |
| R₂ = 2,4-Dichlorophenyl | | | | | | | | | | | | | | | | | | | | | | | | | |
| R₃ = Phenyl | | | | | | | | | | | | | | | | | | | | | | | | | |
| E + T | | | | | | | | | | | | | | | | | | | | | | | | | |
| R₁ = OC₂H₅ | 11.2 | 0 | 0 | — | 0 | — | 0 | 0 | 6 | — | 9 | 2 | 9 | 6 | — | — | — | — | — | — | — | — | — | 7 |
| R₂ = Phenyl | 4.48 | — | 3 | — | 5 | 8 | 3 | 1 | 8 | — | 9 | 0 | 9 | — | — | — | — | — | — | — | — | — | — | — | 2 |
| R₃ = 2-Methylphenyl | 1.12 | — | 0 | — | 0 | 2 | 2 | 0 | 0 | — | 0 | 0 | 2 | — | — | — | — | — | — | — | — | — | — | — | 0 |
| E + T | | | | | | | | | | | | | | | | | | | | | | | | | |
| (64/36) | | | | | | | | | | | | | | | | | | | | | | | | | |
| R₁ = OC₂H₅ | 11.2 | 7 | 8 | — | 9 | 9 | 7 | 7 | 9 | 8 | 9 | 7 | 9 | 9 | 9 | — | — | 5 | 7 | — | — | 2 | 2 | 0 |
| R₂ = Phenyl | 4.48 | 1 | 1 | — | 9 | 9 | 2 | 9 | 9 | 7 | 9 | 0 | 9 | 9 | 9 | — | — | 0 | 2 | — | — | 0 | 0 | 7 |
| R₃ = 3-Chlorophenyl | 0.56 | 0 | 0 | — | 3 | 8 | 0 | 0 | 8 | 0 | 9 | 0 | 9 | 5 | 9 | — | — | 0 | 0 | — | — | 0 | 0 | 0 |
| E + T | 0.28 | — | 0 | — | 0 | 5 | 0 | 0 | 0 | 7 | 0 | 0 | 8 | 0 | 0 | — | — | 0 | 0 | — | — | 0 | 0 | 0 |
| R₁ = OCH₃ | 4.48 | 9 | — | — | 9 | 9 | 0 | 9 | 9 | 8 | 9 | 7 | 9 | 9 | 9 | — | — | 5 | 9 | — | — | 2 | 0 | 9 |
| R₂ = Phenyl | 1.12 | 6 | — | — | 8 | 2 | 0 | 7 | 9 | 7 | 9 | 0 | 9 | 9 | 9 | — | — | 0 | 9 | — | — | 0 | 0 | 2 |
| R₃ = Phenyl | 0.56 | 0 | — | — | 7 | 2 | 0 | 0 | 7 | 0 | 8 | 0 | 9 | 5 | 9 | — | — | 0 | 9 | — | — | 0 | 0 | 0 |
| E + T | 0.28 | 0 | — | — | 6 | 0 | 5 | 0 | 8 | 7 | 7 | 0 | 9 | 7 | 9 | — | — | 5 | 9 | — | — | 6 | 6 | 0 |
| R₁ = OH | 2.24 | 9 | — | — | 9 | 9 | 0 | 9 | 8 | 6 | 9 | 9 | 7 | 8 | 9 | — | — | 0 | 9 | — | — | 0 | 0 | 9 |
| R₂ = Phenyl | 1.12 | 9 | — | — | 8 | 9 | 0 | 3 | 8 | 0 | 9 | 9 | 6 | 5 | 5 | — | — | 0 | 9 | — | — | 0 | 0 | 2 |
| R₃ = 3-Pyridyl | 0.56 | 3 | — | — | 9 | 0 | 0 | 0 | 2 | 0 | 8 | 3 | 3 | 0 | 0 | — | — | 0 | 9 | — | — | 0 | 0 | 0 |
| E + T | 0.28 | 0 | — | — | 5 | — | 0 | 0 | 0 | 0 | 0 | 2 | 3 | 0 | 0 | — | — | 0 | 0 | — | — | 0 | 0 | 0 |
| (70/30) | | | | | | | | | | | | | | | | | | | | | | | | | |
| R₁ = OC₂H₅ | 4.48 | 8 | — | — | 9 | 9 | 0 | 9 | 8 | 8 | 9 | 8 | 9 | 9 | 9 | — | — | 2 | 5 | — | — | 2 | 0 | 9 |
| R₂ = Phenyl | 1.12 | 0 | — | — | 8 | 0 | 0 | 3 | 8 | 3 | 9 | 0 | 9 | 9 | 9 | — | — | 0 | 0 | — | — | 0 | 0 | 2 |
| R₃ = Phenyl | 0.56 | 0 | — | — | 8 | 0 | 0 | 0 | 6 | 0 | 8 | 0 | 8 | 9 | 9 | — | — | 0 | 0 | — | — | 0 | 0 | 0 |
| E + T | 0.28 | 0 | — | — | 6 | — | 0 | 0 | 6 | 0 | 8 | 0 | 8 | 6 | 3 | — | — | 0 | 0 | — | — | 0 | 0 | 0 |
| R₁ = OCH(CH₃)₂ | 4.48 | 0 | — | — | 8 | 9 | 0 | 2 | 7 | 8 | 9 | 8 | 9 | 9 | 9 | — | — | 0 | 2 | — | — | 5 | 2 | 9 |
| R₂ = Phenyl | 1.12 | 0 | — | — | 2 | 0 | 0 | 0 | 0 | 3 | 9 | 9 | 9 | 9 | 9 | — | — | 0 | 0 | — | — | 2 | 0 | 5 |
| R₃ = Phenyl | 0.56 | 0 | — | — | 0 | 0 | 0 | 0 | 0 | 0 | 9 | 0 | 9 | 9 | 9 | — | — | 0 | 0 | — | — | 0 | 0 | 0 |

TABLE I-continued

Preemergence Herbicidal Activity of Polysubstituted Acids and Derivatives having the Formula:

$$N\equiv C-\underset{R_3}{\overset{}{C}}H-\underset{R_2}{\overset{}{C}}H-CH_2-CO-R_1$$

| Structure | Rate kg/ha | PN | SE | LA | MU | PI | RW | MG | VL | TB | BA | CR | FO | WO | DB | CH | CG | CN | SY | AN | NG | ER | BB | ST |
|---|---|---|---|---|---|---|---|---|---|---|---|---|---|---|---|---|---|---|---|---|---|---|---|---|
| E + T (69/31) | 0.28 | 0 | — | — | 0 | — | 0 | — | 0 | 0 | 8 | 0 | 8 | 0 | 5 | — | — | 0 | 0 | — | — | 0 | 0 | 0 |
| $R_1$ = OH | 11.2 | 8 | 9 | — | 9 | 9 | 7 | 8 | 9 | — | 8 | 9 | 9 | 9 | — | — | — | — | — | — | — | — | — | — |
| $R_2$ = 3,4-Dichlorophenyl | 2.24 | 2 | — | — | 8 | 7 | 0 | 0 | 7 | — | 3 | 3 | 8 | 6 | — | — | — | — | — | — | — | — | — | — |
| $R_3$ = Phenyl | 1.12 | 2 | — | — | 9 | 6 | 0 | 0 | 7 | — | 2 | 0 | 5 | 2 | — | — | — | — | — | — | — | — | — | — |
| E + T (62/38) | | | | | | | | | | | | | | | | | | | | | | | | |
| $R_1$ = OH | 11.2 | 2 | 8 | — | 9 | 8 | 0 | 8 | 7 | — | 8 | 9 | 9 | 9 | — | — | — | — | — | — | — | — | — | — |
| $R_2$ = 3-Pyridyl | 2.24 | 0 | — | — | 8 | 0 | 0 | 0 | 0 | — | 0 | 6 | 0 | 8 | — | — | — | — | — | — | — | — | — | — |
| $R_3$ = Phenyl | | | | | | | | | | | | | | | | | | | | | | | | |
| E + T (63/37) | | | | | | | | | | | | | | | | | | | | | | | | |
| $R_1$ = OH | 2.24 | 0 | — | — | 9 | 7 | 0 | 7 | 8 | 3 | 5 | 7 | 9 | 7 | 9 | — | — | 3 | 9 | — | — | 2 | 3 | 7 |
| $R_2$ = 2-Methoxyphenyl | 1.12 | 0 | — | — | 8 | 0 | 0 | 0 | 7 | 0 | 2 | 6 | 9 | 0 | 9 | — | — | 0 | 2 | — | — | 2 | 0 | 2 |
| $R_3$ = Phenyl | 0.56 | 0 | — | — | 2 | 0 | 0 | 0 | 0 | 0 | 0 | 0 | 7 | 0 | 9 | — | — | 0 | 2 | — | — | 0 | 0 | 0 |
| E + T (52/48) | 0.28 | 0 | — | — | 0 | 0 | 0 | 0 | 0 | 0 | 0 | 3 | 8 | 0 | 0 | — | — | 0 | 0 | — | — | 0 | 0 | 0 |
| $R_1$ = OH | 2.24 | 9 | — | — | 9 | 9 | 2 | 8 | 8 | 8 | 5 | 7 | 9 | 9 | 9 | — | — | 7 | 2 | — | — | 9 | 9 | 9 |
| $R_2$ = 4-Nitrophenyl | 1.12 | 2 | — | — | 9 | 9 | 0 | 2 | 8 | 0 | 6 | 5 | 6 | 8 | 9 | — | — | 1 | — | — | — | 9 | 8 | 9 |
| $R_3$ = Phenyl | 0.56 | 2 | — | — | 9 | 7 | 0 | 0 | 7 | 0 | 5 | 0 | 3 | 1 | 9 | — | — | 0 | 0 | — | — | 6 | 8 | 8 |
| E + T (69/31) | 0.28 | 2 | — | — | 8 | 6 | 0 | 0 | 2 | 0 | 2 | 3 | 0 | 0 | 9 | — | — | 0 | 0 | — | — | 3 | 0 | 3 |
| $R_1$ = OH | 2.24 | 9 | — | — | 9 | 9 | 3 | 3 | 9 | 8 | 9 | 9 | 9 | 9 | 9 | — | — | 8 | 9 | — | — | 9 | 9 | 9 |
| $R_2$ = 3-Nitrophenyl | 1.12 | 2 | — | — | 9 | 8 | 0 | 1 | 8 | 1 | 9 | 9 | 9 | 9 | 9 | — | — | 0 | 7 | — | — | 8 | 9 | 9 |
| $R_3$ = Phenyl | 0.56 | 0 | — | — | 8 | 2 | 0 | 0 | 7 | 0 | 9 | 9 | 9 | 7 | 9 | — | — | 0 | 0 | — | — | 5 | 3 | 2 |
| T (3/97) | 0.28 | 0 | — | — | 8 | 2 | 0 | — | 7 | 0 | 8 | 9 | 9 | 7 | 7 | — | — | 0 | 0 | — | — | 2 | 1 | 0 |
| $R_1$ = OH | 2.24 | 9 | — | — | 9 | 8 | 0 | 2 | 8 | 7 | 7 | 8 | 9 | 9 | 7 | — | — | 5 | 6 | — | — | 7 | 7 | 6 |
| $R_2$ = 3-Nitrophenyl | 1.12 | 2 | — | — | 9 | 0 | 0 | 0 | 7 | 0 | 2 | 7 | 7 | 6 | 0 | — | — | 1 | 0 | — | — | 3 | 0 | 3 |
| $R_3$ = Phenyl | 0.56 | 0 | — | — | 8 | 0 | 0 | 0 | 1 | 0 | 0 | 0 | 2 | 0 | 0 | — | — | 1 | 0 | — | — | 1 | 0 | 0 |
| E + T (70/30) | | | | | | | | | | | | | | | | | | | | | | | | |
| $R_1$ = OC$_2$H$_5$ | 2.24 | 8 | — | — | 9 | 9 | 0 | 8 | 0 | 9 | 9 | 6 | 9 | 9 | 1 | — | — | 3 | 3 | — | — | 0 | 5 | 8 |
| $R_2$ = 3-Chlorophenyl | 1.12 | 0 | — | — | 9 | 9 | 0 | 2 | 7 | 5 | 8 | 0 | 9 | 9 | 0 | — | — | 2 | 0 | — | — | 0 | 0 | 7 |
| $R_3$ = Phenyl | 0.28 | 0 | — | — | 9 | 9 | 0 | 0 | 2 | 0 | 7 | 0 | 7 | 7 | 0 | — | — | 0 | 0 | — | — | 0 | 0 | 0 |
| E + T (30/70) | 0.14 | 0 | — | — | 8 | 9 | 0 | 0 | 0 | 0 | 6 | 0 | 6 | 7 | 0 | — | — | 0 | 0 | — | — | 0 | 0 | 0 |
| $R_1$ = OH | 2.24 | 9 | — | — | 9 | 9 | 2 | 2 | 8 | 7 | 6 | 0 | 9 | 8 | 0 | — | — | 3 | 0 | — | — | 1 | 3 | 6 |
| $R_2$ = Phenyl | 1.12 | 0 | — | — | 9 | 9 | 0 | 2 | 7 | 6 | 7 | 0 | 9 | 7 | 0 | — | — | 2 | 0 | — | — | 0 | 0 | 6 |
| $R_3$ = 3-Methylphenyl | 0.28 | — | — | — | 9 | 9 | 0 | 0 | 7 | 0 | 3 | 0 | 7 | 1 | 0 | — | — | 0 | 0 | — | — | 0 | 0 | 3 |
| E + T (66/34) | 0.14 | 0 | — | — | 9 | 7 | 0 | 0 | 3 | 0 | 3 | 0 | 5 | 0 | 0 | — | — | 0 | 0 | — | — | 0 | 0 | 0 |
| $R_1$ = OC$_2$H$_5$ | 2.24 | 2 | — | — | 9 | 3 | 0 | 9 | 8 | 9 | 9 | 0 | 8 | 9 | 0 | — | — | 5 | 9 | 5 | 5 | — | — | 9 |
| $R_2$ = Phenyl | 1.12 | 0 | — | — | 8 | 0 | — | 2 | 5 | 8 | 9 | 0 | 7 | 9 | 0 | — | — | 3 | 6 | 2 | 0 | — | — | 8 |
| $R_3$ = Phenyl | 0.56 | 0 | — | — | 9 | 0 | 0 | 0 | 2 | 9 | 8 | 0 | 7 | 9 | 0 | — | — | 0 | 6 | 0 | 0 | — | — | 8 |

TABLE I-continued

Preemergence Herbicidal Activity of Polysubstituted Acids and Derivatives having the Formula:

$$N \equiv C - \underset{\underset{R_2}{|}}{\overset{\overset{R_3}{|}}{C}} - CH - CH - CH_2 - CO - R_1$$

| Structure | Rate kg/ha | PN | SE | LA | MU | PI | RW | MG | VL | TB | BA | CR | FO | WO | DB | CH | CG | CN | SY | AN | NG | ER | BB | ST |
|---|---|---|---|---|---|---|---|---|---|---|---|---|---|---|---|---|---|---|---|---|---|---|---|---|
| (3/97) T | | | | | | | | | | | | | | | | | | | | | | | | |
| R₁ = OH | 0.28 | 0 | — | — | 2 | 0 | 0 | 0 | 2 | 0 | 8 | 0 | 6 | 9 | 0 | — | — | 0 | — | 0 | 0 | — | — | 2 |
| R₁ = OH | 2.24 | 2 | — | — | 9 | 8 | 0 | 7 | 7 | 6 | 2 | 2 | 7 | 7 | 8 | — | — | 3 | 6 | — | — | 6 | 6 | 7 |
| R₂ = 2-Methoxyphenyl | 1.12 | 2 | — | — | 8 | 6 | 0 | 6 | 7 | 3 | 2 | 0 | 7 | 7 | 7 | — | — | 5 | 5 | — | — | 6 | 6 | 7 |
| R₃ = Phenyl | 0.56 | 2 | — | — | 8 | 6 | 0 | 3 | 5 | 3 | 0 | 0 | 6 | 6 | 7 | — | — | 2 | — | — | — | 7 | 3 | 7 |
| E + T (48/52) | 0.28 | 2 | — | — | 8 | 0 | 0 | 0 | 0 | 2 | 0 | 0 | 0 | 0 | 3 | — | — | 0 | 5 | — | — | 0 | 0 | 5 |
| R₁ = OH . NH₂CH₂CH₂OH | 2.24 | 7 | — | — | 8 | 0 | 0 | 2 | 8 | 9 | 0 | 0 | 6 | 9 | 0 | — | — | 0 | 9 | 0 | 0 | — | — | 7 |
| R₂ = Phenyl | 1.12 | 0 | — | — | 2 | 0 | 0 | 0 | 8 | 9 | 0 | 0 | 0 | 8 | 0 | — | — | 0 | 0 | 0 | 0 | — | — | 5 |
| R₃ = Phenyl | 0.56 | 0 | — | — | 0 | 0 | 0 | 0 | 0 | 5 | 0 | 0 | 0 | 2 | 0 | — | — | 0 | 0 | 0 | 0 | — | — | 3 |
| E + T (66/34) | | | | | | | | | | | | | | | | | | | | | | | | |
| R₁ = OH . NH(CH₃)₂ | 2.24 | 2 | — | — | 8 | 2 | 0 | 0 | 6 | 0 | 0 | 0 | 2 | 8 | 0 | — | — | 0 | 0 | 0 | 3 | — | — | 7 |
| R₂ = Phenyl | 1.12 | 0 | — | — | 3 | 0 | 0 | 0 | 2 | 0 | 0 | 0 | 0 | 8 | 0 | — | — | 0 | 0 | 0 | 2 | — | — | 7 |
| R₃ = Phenyl | | | | | | | | | | | | | | | | | | | | | | | | |
| E + T (67/33) | | | | | | | | | | | | | | | | | | | | | | | | |
| R₁ = ONa . ½H₂O | 2.24 | 9 | — | — | 9 | 7 | 0 | 2 | 7 | 7 | 7 | 3 | 7 | 9 | 6 | — | — | 1 | 0 | 2 | 3 | — | — | 8 |
| R₂ = Phenyl | 1.12 | 0 | — | — | 8 | 0 | 0 | 2 | 5 | 2 | 2 | 0 | 5 | 9 | 6 | — | — | 0 | 0 | 0 | 2 | — | — | 8 |
| R₃ = Phenyl | 0.56 | 0 | — | — | 5 | 0 | 0 | 0 | 0 | 0 | 0 | 0 | 6 | 9 | 0 | — | — | 0 | 0 | 0 | 0 | — | — | 6 |
| E + T (40/60) | | | | | | | | | | | | | | | | | | | | | | | | |
| R₁ = OH | 2.24 | 0 | — | — | 9 | 9 | 2 | 7 | 9 | 8 | 9 | 3 | 9 | 8 | 6 | — | — | 6 | 3 | 2 | 6 | — | — | 8 |
| R₂ = 4-Chlorophenyl | 1.12 | 0 | — | — | 8 | 9 | 0 | 2 | 8 | 2 | 7 | 0 | 8 | 7 | 6 | — | — | 2 | 0 | 0 | 3 | — | — | 6 |
| R₃ = Phenyl | 0.56 | 0 | — | — | 8 | 3 | 0 | 0 | 7 | 0 | 6 | 0 | 5 | 7 | 0 | — | — | 0 | 0 | 0 | 0 | — | — | 0 |
| E + T (69/31) | 0.28 | 0 | — | — | 7 | 0 | 0 | 0 | 7 | 0 | 0 | 0 | 0 | 6 | 0 | — | — | 0 | 0 | 0 | 0 | — | — | 0 |
| R₁ = OH | 2.24 | 9 | — | — | 9 | 9 | 9 | 9 | 9 | 9 | 9 | 9 | 9 | 9 | 9 | — | — | 9 | 7 | 9 | 9 | — | — | 9 |
| R₂ = 4-Chlorophenyl | 1.12 | 9 | — | — | 9 | 9 | 7 | 9 | 9 | 9 | 9 | 8 | 9 | 9 | 8 | — | — | 8 | 6 | 8 | 8 | — | — | 8 |
| R₃ = Phenyl | 0.28 | 0 | — | — | 8 | 9 | 0 | 0 | 9 | 8 | 9 | 0 | 8 | 8 | 7 | — | — | 5 | 0 | 7 | 7 | — | — | 8 |
| T (12/88) | 0.14 | 0 | — | — | 8 | 9 | 0 | 0 | 7 | 0 | 7 | 0 | 8 | 8 | 2 | — | — | 2 | 0 | 3 | 3 | — | — | 5 |
| R₁ = OC₂H₅ | 2.24 | 0 | — | — | 9 | 8 | 0 | 3 | 8 | 0 | 8 | 0 | 9 | 9 | 2 | — | — | 2 | 0 | 7 | 7 | — | — | 8 |
| R₂ = 4-Chlorophenyl | 1.12 | 0 | — | — | 8 | 7 | 0 | 0 | 5 | 0 | 7 | 0 | 7 | 8 | 2 | — | — | 2 | 0 | 5 | 5 | — | — | 7 |
| R₃ = Phenyl | 0.56 | 0 | — | — | 7 | 0 | 0 | 0 | 0 | 0 | 3 | 0 | 3 | 3 | 0 | — | — | 0 | 0 | 2 | 2 | — | — | 5 |
| E + T (77/23) | | | | | | | | | | | | | | | | | | | | | | | | |
| R₁ = OC₂H₅ | 2.24 | 0 | — | — | 9 | 0 | 0 | 0 | 7 | 7 | 3 | 0 | 7 | 9 | 0 | — | — | 0 | 0 | 0 | 0 | — | — | 3 |
| R₂ = 3-Trifluoromethylphenyl | 1.12 | 0 | — | — | 7 | 0 | 0 | 0 | 6 | 0 | 0 | 0 | 6 | 5 | 0 | — | — | 0 | 0 | 0 | 0 | — | — | 0 |
| R₃ = Phenyl | | | | | | | | | | | | | | | | | | | | | | | | |
| E + T | | | | | | | | | | | | | | | | | | | | | | | | |
| R₁ = OLi . ½H₂O | 2.24 | 0 | — | — | 8 | 0 | 0 | 2 | 7 | 2 | 6 | 0 | 8 | 9 | 0 | — | — | 2 | 2 | 2 | 2 | — | — | 6 |
| R₂ = Phenyl | 1.12 | 0 | — | — | 7 | 0 | 0 | 0 | 6 | 0 | 5 | 0 | 7 | 8 | 0 | — | — | 0 | 0 | 0 | 0 | — | — | 3 |
| R₃ = Phenyl | | | | | | | | | | | | | | | | | | | | | | | | |

TABLE I-continued

Preemergence Herbicidal Activity of Polysubstituted Acids and Derivatives having the Formula:

$$N\equiv C-CH-CH-CH_2-CO-R_1$$
$$\phantom{N\equiv C-}\overset{R_3}{|}\phantom{-}\overset{|}{R_2}$$

| Structure | Rate kg/ha | PN | SE | LA | MU | PI | RW | MG | VL | TB | BA | CR | FO | WO | DB | CH | CG | CN | SY | AN | NG | ER | BB | ST |
|---|---|---|---|---|---|---|---|---|---|---|---|---|---|---|---|---|---|---|---|---|---|---|---|---|
| E + T (71/29) $R_1$ = OCH$_2$CCl=CH$_2$ $R_2$ = Phenyl $R_3$ = Phenyl | 2.24 1.12 0.56 | 0 0 0 | — — — | — — — | 8 5 0 | 0 0 0 | 0 0 0 | 0 0 0 | 3 3 0 | 3 0 0 | 9 9 6 | 0 0 0 | 9 8 7 | 9 8 8 | 0 0 0 | — — — | — — — | 0 0 0 | 3 0 0 | 0 0 0 | 3 0 0 | — — — | — — — | 0 0 0 |
| E + T (27/73) $R_1$ = OH $R_2$ = 3-Trifluoromethylphenyl $R_3$ = Phenyl | 2.24 1.12 0.56 | 0 0 0 | — — — | — — — | 9 8 8 | 6 0 0 | 3 0 0 | 1 0 0 | 8 8 8 | 7 0 0 | 2 0 0 | 2 0 0 | 9 8 6 | 7 3 5 | 0 0 0 | — — — | — — — | 5 2 0 | 0 0 0 | 9 7 1 | 5 3 0 | — — — | — — — | 7 7 2 |
| E + T (29/71) $R_1$ = OC$_2$H$_5$ $R_2$ = Phenyl $R_3$ = 3,5-Dichlorophenyl | 2.24 1.12 0.56 | 0 0 0 | — — — | — — — | 6 0 0 | 3 0 0 | 0 0 0 | 0 0 0 | 2 0 0 | 0 0 0 | 7 3 0 | 9 9 9 | 8 7 6 | 0 0 0 | 0 0 0 | — — — | — — — | 0 0 0 | 0 0 0 | 3 0 0 | 2 0 0 | — — — | — — — | 2 0 0 |
| — $R_1$ = OC$_2$H$_5$ $R_2$ = Phenyl $R_3$ = 3,5-Dichlorophenyl T | 2.24 1.12 0.56 0.14 | 1 0 0 0 | — — — — | — — — — | 8 7 6 1 | 9 8 7 2 | 7 1 1 0 | 0 0 0 0 | 7 3 0 0 | 0 0 0 0 | 9 9 9 7 | 9 9 9 9 | 9 9 9 8 | 9 8 8 2 | 9 8 6 0 | — — — — | — — — — | 6 3 0 0 | 0 0 0 0 | 7 6 7 1 | 7 7 5 0 | — — — — | — — — — | 5 6 5 1 |
| (5/95) $R_1$ = OC$_2$H$_5$ $R_2$ = 2-Chlorophenyl $R_3$ = Phenyl E + T | 2.24 1.12 | 0 0 | — — | — — | 3 2 | 3 2 | 7 0 | 1 0 | 3 2 | 0 0 | 3 1 | 2 0 | 7 6 | 8 7 | 0 0 | — — | — — | 0 0 | 2 0 | 5 3 | 3 2 | — — | — — | 6 2 |
| $R_1$ = OC$_2$H$_5$ $R_2$ = 4-Chlorophenyl $R_3$ = 3-Chlorophenyl E + T (70/30) | 2.24 1.12 | 0 0 | — — | — — | 8 8 | 5 5 | 3 0 | 0 0 | 5 0 | 7 2 | 9 8 | 9 6 | 9 6 | 9 9 | 7 3 | — — | — — | 5 2 | 0 0 | 2 2 | 3 0 | — — | — — | 3 2 |
| $R_1$ = OC$_2$H$_5$ $R_2$ = 4-Chlorophenyl $R_3$ = 4-Chlorophenyl | 2.24 1.12 | 0 0 | — — | — — | 3 2 | 5 0 | 0 0 | 0 0 | 0 0 | 0 0 | 8 1 | 9 9 | 9 7 | 5 2 | 0 0 | — — | — — | 0 0 | 0 0 | 3 0 | 3 0 | — — | — — | 3 0 |
| E + T (45/55) $R_1$ = OH $R_2$ = Phenyl $R_3$ = 3-Methylphenyl | 2.24 1.12 0.56 | 3 2 0 | — — — | — — — | 8 7 5 | 9 7 0 | 0 0 0 | 8 8 7 | 6 6 5 | 5 5 3 | 9 7 5 | 2 0 0 | 8 7 2 | 7 6 0 | 8 7 7 | — — — | — — — | 3 2 0 | 7 3 2 | 7 2 0 | — — — | — — — | 7 8 0 | 8 7 5 |
| E + T $R_1$ = OH $R_2$ = 4-Chlorophenyl $R_3$ = 3-Chlorophenyl | 2.24 1.12 0.56 | 6 0 0 | — — — | — — — | 8 8 7 | 9 9 8 | 5 2 0 | 6 1 0 | 8 8 2 | 3 0 0 | 9 8 7 | 9 8 2 | 8 8 2 | 9 6 5 | 7 7 0 | — — — | — — — | 7 3 0 | 0 0 0 | 7 2 0 | 7 6 7 | — — — | — — — | 3 2 0 |

TABLE I-continued

Preemergence Herbicidal Activity of Polysubstituted Acids and Derivatives having the Formula:

$$N\equiv C-CH(R_3)-CH(R_2)-CH_2-CO-R_1$$

| Structure | Rate kg/ha | PN | SE | LA | MU | PI | RW | MG | VL | TB | BA | CR | FO | WO | DB | CH | CG | CN | SY | AN | NG | ER | BB | ST |
|---|---|---|---|---|---|---|---|---|---|---|---|---|---|---|---|---|---|---|---|---|---|---|---|---|
| E + T (79/21) | 0.28 | 0 | — | — | 3 | 7 | 0 | 0 | 0 | 0 | 8 | 0 | 0 | 1 | 0 | — | — | 0 | 0 | 0 | 0 | — | — | 0 |
| $R_1$ = OH | 2.24 | 2 | — | — | 9 | 9 | 8 | 6 | 8 | 3 | 9 | 9 | 8 | 9 | 9 | — | — | 7 | 0 | 8 | 9 | — | — | 7 |
| $R_2$ = 4-Chlorophenyl | 1.12 | 1 | — | — | 8 | 9 | 8 | 5 | 8 | 3 | 9 | 9 | 7 | 9 | 9 | — | — | 1 | 0 | 7 | 8 | — | — | 6 |
| $R_3$ = 3-Chlorophenyl | 0.28 | 0 | — | — | 8 | 9 | 0 | 0 | 3 | — | 8 | 8 | 7 | 5 | 8 | — | — | 0 | 0 | 3 | 3 | — | — | 1 |
| E + T (30/70) | 0.14 | 0 | — | — | 8 | 9 | 0 | 0 | — | 0 | 5 | 3 | 0 | 3 | 7 | — | — | 0 | 0 | 0 | 0 | — | — | 0 |
| $R_1$ = OH | 2.24 | 7 | — | — | 9 | 9 | 8 | 7 | 8 | 5 | 9 | 9 | 9 | 8 | 9 | — | — | 7 | 0 | 7 | 8 | — | — | 9 |
| $R_2$ = Phenyl | 1.12 | 2 | — | — | 8 | 9 | 3 | 3 | 8 | 3 | 9 | 9 | 9 | 8 | 9 | — | — | 2 | 0 | 6 | 7 | — | — | 9 |
| $R_3$ = 3,5-Dichlorophenyl | 0.56 | 1 | — | — | 8 | 9 | 0 | 0 | 1 | 3 | 9 | 9 | 9 | 7 | 9 | — | — | 0 | 0 | 3 | 6 | — | — | 9 |
| E + T (58/42) | 0.14 | 0 | — | — | 2 | 7 | 0 | 0 | 0 | 0 | 5 | 3 | 8 | 1 | 6 | — | — | 0 | 0 | 1 | 1 | — | — | 6 |
| $R_1$ = OH | 2.24 | 9 | — | — | 8 | 9 | 0 | 8 | 8 | 8 | 9 | 9 | 9 | 9 | 2 | — | — | 9 | 5 | 6 | 6 | — | — | 8 |
| $R_2$ = Phenyl | 1.12 | 9 | — | — | 7 | 8 | 0 | 7 | 8 | 8 | 9 | 9 | 9 | 9 | 0 | — | — | 7 | 1 | 5 | 5 | — | — | 7 |
| $R_3$ = 4-Fluorophenyl | 0.56 | 8 | — | — | 7 | 8 | 0 | 5 | 7 | 7 | 9 | 9 | 7 | 9 | 0 | — | — | 5 | 0 | 2 | 3 | — | — | 5 |
| E + T (56/44) | 0.14 | 7 | — | — | 5 | 5 | 0 | 3 | 3 | 0 | 9 | 9 | 8 | 8 | 0 | — | — | 1 | 0 | 0 | 0 | — | — | 0 |
| $R_1$ = OCH$_2$CH$_2$—O—C$_4$H$_9$-n | 2.24 | 7 | — | — | 8 | 7 | 5 | 2 | 8 | 7 | 9 | 0 | 9 | 9 | 7 | — | — | 0 | 3 | 3 | 3 | — | — | 7 |
| $R_2$ = Phenyl | 1.12 | 5 | — | — | 3 | 2 | 0 | 0 | 7 | 1 | 9 | 0 | 9 | 8 | 0 | — | — | 0 | 3 | 2 | 2 | — | — | 3 |
| $R_3$ = Phenyl | 0.56 | 0 | — | — | 3 | 0 | 0 | 0 | 2 | 0 | 9 | 0 | 9 | 8 | — | — | — | 0 | 0 | 0 | 0 | — | — | 3 |
| E + T (40/60) | 0.28 | 0 | — | — | 0 | 0 | 0 | 0 | 0 | 0 | 9 | 0 | 9 | 7 | 0 | — | — | 0 | 0 | 0 | 0 | — | — | 1 |
| $R_1$ = OC$_2$H$_5$ | 2.24 | 0 | — | — | 8 | 8 | 2 | 8 | 7 | 1 | 9 | 9 | 8 | 9 | 5 | — | — | 3 | 1 | 7 | 8 | — | — | 8 |
| $R_2$ = 4-Chlorophenyl | 1.12 | 0 | — | — | 8 | 8 | 0 | 7 | 6 | 0 | 9 | 9 | 9 | 8 | 0 | — | — | 1 | 0 | 5 | 7 | — | — | 6 |
| $R_3$ = 3-Chlorophenyl | 0.56 | 0 | — | — | 8 | 7 | 0 | 1 | 3 | 0 | 9 | 6 | 6 | 8 | 0 | — | — | 0 | 0 | 3 | 5 | — | — | 2 |
| T (19/81) | 0.28 | 0 | — | — | 7 | 0 | 0 | 0 | 0 | 0 | 7 | 6 | 6 | 3 | 0 | — | — | 0 | 0 | 2 | 2 | — | — | 0 |
| $R_1$ = OH | 2.24 | 0 | — | — | 8 | 9 | 0 | 0 | 7 | 0 | 9 | 8 | 9 | 7 | 7 | — | — | 0 | 0 | 2 | 0 | — | — | 5 |
| $R_2$ = 4-Chlorophenyl | 1.12 | 0 | — | — | 8 | 8 | 0 | 0 | 2 | 0 | 9 | 5 | 9 | 5 | 2 | — | — | 0 | 0 | 0 | 0 | — | — | 1 |
| $R_3$ = 4-Chlorophenyl | 0.56 | 0 | — | — | 8 | 6 | 0 | 0 | 0 | 0 | 5 | 2 | 3 | 0 | 2 | — | — | 0 | 0 | 0 | 0 | — | — | 0 |
| E + T (37/63) | 2.24 | 6 | — | — | 8 | 7 | 2 | 2 | 8 | 2 | 9 | 3 | 9 | 8 | 5 | — | — | 2 | 1 | 6 | 5 | — | — | 3 |
| $R_1$ = OC$_2$H$_5$ | 1.12 | 3 | — | — | 7 | 0 | 0 | 1 | 7 | 0 | 9 | 5 | 9 | 8 | 0 | — | — | 1 | 0 | 5 | 3 | — | — | 2 |
| $R_2$ = 3-Methoxyphenyl | 0.56 | 0 | — | — | 5 | 0 | 0 | 0 | 3 | 0 | 9 | 3 | 9 | 1 | 0 | — | — | 0 | 0 | 0 | 2 | — | — | 0 |
| $R_3$ = Phenyl | 0.28 | 0 | — | — | 0 | 0 | 0 | 0 | 0 | 0 | 7 | 0 | 7 | 0 | 0 | — | — | 0 | 0 | 0 | 0 | — | — | 0 |
| E + T (60/40) | 4.48 | 0 | 7 | — | 9 | 9 | 0 | 1 | 3 | — | 9 | 9 | 9 | 9 | — | — | — | — | — | — | — | — | — | — |
| *$R_1$ = OC$_2$H$_5$ | 1.12 | 0 | 0 | — | 2 | 8 | 0 | 0 | 0 | — | 9 | 9 | 9 | 1 | — | — | — | — | — | — | — | — | — | — |
| $R_2$ = Phenyl | 0.56 | 0 | 0 | — | 2 | 2 | 0 | 0 | 0 | — | 9 | 7 | 2 | 0 | — | — | — | — | — | — | — | — | — | — |
| $R_3$ = 3-Pyridyl E + T (58/42) | 1.12 | 3 | 7 | 2 | 9 | 9 | 2 | 8 | 8 | 0 | 9 | 9 | 9 | 2 | — | — | — | — | — | — | — | — | — | — |
| *$R_1$ = OC$_2$H$_5$ | 0.56 | 0 | 7 | 2 | 8 | 8 | 0 | 0 | 6 | 0 | 9 | 9 | 9 | 0 | — | — | — | — | — | — | — | — | — | — |
| $R_2$ = 4-Methylphenyl | 0.28 | 0 | 3 | 2 | 3 | 3 | 0 | 0 | 5 | 0 | 9 | 9 | 9 | 0 | — | — | — | — | — | — | — | — | — | — |
| $R_3$ = Phenyl | | | | | | | | | | | | | | | | | | | | | | | | |

TABLE I-continued

Preemergence Herbicidal Activity of Polysubstituted Acids and Derivatives having the Formula:

$$N\equiv C-\underset{R_2}{\underset{|}{C}}H-\underset{R_3}{\underset{|}{C}}H-CH_2-CO-R_1$$

| Structure | Rate kg/ha | PN | SE | LA | MU | PI | RW | MG | VL | TB | BA | CR | FO | WO | DB | CH | CG | CN | SY | AN | NG | ER | BB | ST |
|---|---|---|---|---|---|---|---|---|---|---|---|---|---|---|---|---|---|---|---|---|---|---|---|---|
| E + T (51/49) |||||||||||||||||||||||||
| R₁ = OH | 2.24 | 8 | — | — | 9 | 9 | 8 | 9 | 9 | 9 | 9 | 9 | 9 | 9 | 9 | — | — | 5 | 9 | — | — | 8 | 8 | 9 |
| R₂ = Phenyl | 1.12 | 6 | — | — | 9 | 9 | 5 | 9 | 8 | 5 | 9 | 9 | 9 | 9 | 9 | — | — | 3 | 0 | — | — | 8 | 7 | 9 |
| R₃ = 3-Chlorophenyl | 0.56 | 3 | — | — | 8 | 9 | 1 | 9 | 8 | 0 | 9 | 9 | 9 | 9 | 9 | — | — | 2 | 0 | — | — | 6 | 3 | 7 |
| E + T (67/33) | 0.28 | 2 | — | — | 7 | 7 | 0 | 8 | 8 | 0 | 9 | 9 | 9 | 8 | 9 | — | — | 3 | 0 | — | — | 3 | 3 | 7 |
| R₁ = OH | 2.24 | 7 | — | — | 8 | 8 | 3 | 7 | 8 | 7 | 9 | 6 | 9 | 9 | 9 | — | — | 5 | 3 | 7 | 7 | — | — | 6 |
| R₂ = 3-Methoxyphenyl | 1.12 | 7 | — | — | 8 | 7 | 0 | 3 | 8 | 2 | 8 | 1 | 9 | 7 | 6 | — | — | 1 | 3 | 3 | 5 | — | — | 6 |
| R₃ = Phenyl | 0.56 | 5 | — | — | 7 | 3 | 0 | 0 | 6 | 0 | 7 | 0 | 8 | 2 | 2 | — | — | 0 | 0 | 2 | 3 | — | — | 0 |
| E + T (65/35) |||||||||||||||||||||||||
| R₁ = OH | 2.24 | 0 | — | — | 9 | 9 | 0 | 8 | 8 | 3 | 9 | 9 | 9 | 9 | 9 | — | — | 5 | 0 | 5 | 7 | — | — | 7 |
| R₂ = Phenyl | 1.12 | 0 | — | — | 8 | 9 | 0 | 2 | 5 | 3 | 9 | 9 | 9 | 9 | 7 | — | — | 3 | 0 | 1 | 3 | — | — | 6 |
| R₃ = 3,4-Dichlorophenyl | 0.28 | 0 | — | — | 8 | 8 | 0 | 0 | 2 | 0 | 8 | 9 | 8 | 8 | — | — | — | 0 | 0 | 0 | 0 | — | — | 1 |
| E + T (57/43) | 0.14 | 0 | — | — | 7 | 8 | 0 | 0 | 0 | 0 | 8 | 7 | 6 | 0 | 0 | — | — | 0 | 0 | 0 | 0 | — | — | 0 |
| R₁ = O—CH₂—C≡CCH₂OH | 2.24 | 7 | — | — | 8 | 0 | 0 | 3 | 8 | 7 | 9 | 0 | 9 | 9 | 7 | — | — | 3 | 0 | 3 | 3 | — | — | 7 |
| R₂ = Phenyl | 1.12 | 6 | — | — | 7 | 0 | 0 | 0 | 7 | 0 | 9 | 0 | 9 | 8 | 5 | — | — | 2 | 0 | 1 | 0 | — | — | 3 |
| R₃ = Phenyl | 0.56 | 0 | — | — | 3 | 0 | 0 | 0 | 3 | 0 | 9 | 0 | 9 | 7 | 5 | — | — | 0 | 0 | 0 | 0 | — | — | 3 |
| E + T (60/40) | 0.28 | 0 | — | — | 2 | 0 | 0 | 0 | — | — | 9 | 0 | 8 | 3 | 0 | — | — | 0 | 0 | 0 | 0 | — | — | 2 |
| R₁ = OC₈H₁₇-n | 2.24 | 5 | — | — | 5 | 8 | 2 | 2 | 7 | 2 | 9 | 0 | 9 | 8 | 5 | — | — | 5 | 2 | 3 | 2 | — | — | 2 |
| R₂ = Phenyl | 1.12 | 5 | — | — | 2 | 0 | 0 | 0 | 3 | 0 | 9 | 0 | 9 | 8 | 0 | — | — | 1 | 1 | 1 | 1 | — | — | 1 |
| R₃ = Phenyl | 0.56 | 0 | — | — | 0 | 0 | 0 | 0 | — | 0 | 9 | 0 | 9 | 8 | 0 | — | — | 0 | 0 | 0 | 0 | — | — | 0 |
| T (5/95) | 0.28 | 0 | — | — | 0 | 0 | 0 | 0 | — | — | 9 | 0 | 7 | 5 | 0 | — | — | 0 | 0 | 0 | 0 | — | — | 0 |
| R₁ = OCH₂C≡CCH₂Cl | 2.24 | 7 | — | — | 7 | 3 | 0 | 0 | 3 | 0 | 9 | 0 | 9 | 9 | 0 | — | — | 0 | 1 | 0 | 0 | — | — | 1 |
| R₂ = Phenyl | 1.12 | 0 | — | — | 2 | 0 | 0 | 0 | 1 | 0 | 8 | 0 | 9 | 7 | 0 | — | — | 0 | 0 | 0 | 0 | — | — | 0 |
| R₃ = Phenyl | 0.56 | 0 | — | — | 1 | 0 | 0 | 0 | 0 | 0 | 8 | 0 | 8 | 5 | 0 | — | — | 0 | 0 | 0 | 0 | — | — | 0 |
| E + T (65/35) |||||||||||||||||||||||||
| R₁ = OC₂H₅ | 2.24 | 0 | — | — | 0 | 7 | 0 | 0 | 0 | 0 | 8 | 9 | 8 | 3 | 0 | — | — | 1 | 0 | 0 | 0 | — | — | 0 |
| R₂ = 2,4-Dichlorophenyl | 1.12 | 0 | — | — | 0 | 0 | 0 | 0 | 0 | 0 | 3 | 8 | 5 | 2 | 0 | — | — | 0 | 0 | 0 | 0 | — | — | 0 |
| R₃ = 3-Chlorophenyl |||||||||||||||||||||||||
| E + T (50/50) |||||||||||||||||||||||||
| R₁ = OC₂H₅ | 2.24 | 7 | — | — | 8 | 7 | 0 | 1 | 3 | 7 | 9 | 8 | 9 | 9 | 0 | — | — | 2 | 2 | 8 | 7 | — | — | 8 |
| R₂ = 3-Cyanophenyl | 1.12 | 2 | — | — | 8 | 0 | 0 | 0 | 0 | 1 | 9 | 7 | 9 | 8 | 0 | — | — | 0 | 0 | 7 | 5 | — | — | 7 |
| R₃ = Phenyl | 0.56 | 0 | — | — | 8 | 0 | 0 | 0 | 0 | 7 | 7 | 3 | 7 | 8 | 0 | — | — | 0 | 0 | 5 | 2 | — | — | 2 |
| T (15/85) | 0.28 | 0 | — | — | 5 | 0 | 0 | 0 | 0 | 7 | 7 | 1 | 5 | 8 | 0 | — | — | 0 | 0 | 5 | 2 | — | — | 0 |
| R₁ = OC₂H₅ | 2.24 | 3 | — | — | 9 | 9 | 3 | 0 | 7 | 0 | 9 | 9 | 9 | 9 | 0 | — | — | 3 | 3 | 7 | 7 | — | — | 7 |
| R₂ = 3-Cyanophenyl | 1.12 | 0 | — | — | 8 | 8 | 0 | 0 | 0 | 0 | 9 | 9 | 7 | 9 | 0 | — | — | 0 | 3 | 2 | 5 | — | — | 7 |

TABLE I-continued
Preemergence Herbicidal Activity of Polysubstituted Acids and Derivatives having the Formula:

$$N\equiv C-CH-CH-CH_2-CO-R_1$$
$$\phantom{N\equiv C-}|\phantom{CH-}|$$
$$\phantom{N\equiv C-}R_3\phantom{H-}R_2$$

| Structure | Rate kg/ha | PN | SE | LA | MU | PI | RW | MG | VL | TB | BA | CR | FO | WO | DB | CH | CG | CN | SY | AN | NG | ER | BB | ST |
|---|---|---|---|---|---|---|---|---|---|---|---|---|---|---|---|---|---|---|---|---|---|---|---|---|
| $R_3$ = 3-Chlorophenyl | 0.56 | 0 | — | — | 5 | 6 | 0 | 0 | 0 | 0 | 9 | 8 | 2 | 5 | 0 | — | — | 0 | 0 | 2 | 3 | — | — | 3 |
| E + T (50/50) | 0.28 | 0 | — | — | 2 | 2 | 0 | 0 | 0 | 0 | 5 | 8 | 0 | 2 | 0 | — | — | 0 | 0 | 2 | 0 | — | — | 1 |
| $R_1$ = OC$_2$H$_5$ | 2.24 | 7 | — | — | 8 | 6 | 2 | 0 | 9 | 8 | 9 | 3 | 9 | 9 | 0 | — | — | 2 | 2 | 5 | 5 | — | — | 8 |
| $R_2$ = 4-Fluorophenyl | 1.12 | 7 | — | — | 8 | 6 | 0 | 0 | 8 | 0 | 9 | 1 | 9 | 9 | 0 | — | — | 1 | 0 | 5 | 5 | — | — | 8 |
| $R_3$ = Phenyl | 0.56 | 8 | — | — | 8 | 0 | 0 | 0 | 2 | 0 | 8 | 0 | 9 | 7 | 0 | — | — | 0 | 0 | 3 | 3 | — | — | 6 |
| E + T (60/40) | 0.28 | 0 | — | — | 1 | 0 | 0 | 0 | 0 | 0 | 7 | 0 | 5 | 3 | 0 | — | — | 0 | 0 | 1 | 2 | — | — | 2 |
| $R_1$ = OH | 2.24 | 9 | — | — | 8 | 8 | 2 | 2 | 8 | 7 | 9 | 2 | 9 | 9 | 7 | — | — | 5 | 3 | 5 | 7 | — | — | 7 |
| $R_2$ = 4-Fluorophenyl | 1.12 | 9 | — | — | 8 | 8 | 0 | 0 | 8 | 6 | 9 | 1 | 9 | 9 | 7 | — | — | 1 | 0 | 2 | 6 | — | — | 5 |
| $R_3$ = Phenyl | 0.56 | 7 | — | — | 8 | 3 | 0 | 0 | 8 | 2 | 7 | 0 | 8 | 7 | 3 | — | — | 0 | 0 | 1 | 4 | — | — | 5 |
| E + T (76/24) | 0.28 | 0 | — | — | 3 | 0 | 0 | 0 | 2 | 0 | 6 | 0 | 7 | 2 | 0 | — | — | 0 | 0 | 0 | 0 | — | — | 3 |
| $R_1$ = OH | 2.24 | 3 | — | — | 8 | 9 | 5 | 5 | 8 | 0 | 8 | 8 | 5 | 8 | 0 | — | — | 2 | 0 | 2 | 0 | — | — | 1 |
| $R_2$ = 2,4-Dichlorophenyl | 1.12 | 0 | — | — | 3 | 2 | 0 | 0 | 1 | 0 | 7 | 7 | 1 | 8 | 0 | — | — | 0 | 0 | 0 | 0 | — | — | 0 |
| $R_3$ = 3-Chlorophenyl | 0.56 | 0 | — | — | 1 | 0 | 0 | 0 | 0 | 0 | 6 | 5 | 0 | 0 | 0 | — | — | 0 | 0 | 0 | 0 | — | — | 0 |
| E + T (50/50) | | | | | | | | | | | | | | | | | | | | | | | | |
| $R_1$ = OH | 2.24 | 7 | — | — | 8 | 0 | 0 | 2 | 8 | 7 | 9 | 5 | 9 | 8 | 8 | — | — | 1 | 0 | 7 | 7 | — | — | 6 |
| $R_2$ = 3-Cyanophenyl | 1.12 | 2 | — | — | 8 | 0 | 0 | 0 | 2 | 0 | 0 | 0 | 2 | 7 | 0 | — | — | 0 | 0 | 2 | 5 | — | — | 5 |
| $R_3$ = Phenyl | 0.56 | 0 | — | — | 8 | 0 | 0 | 0 | 0 | 0 | 0 | 0 | 0 | 2 | 0 | — | — | 0 | 0 | 0 | 3 | — | — | 0 |
| E + T (75/25) | | | | | | | | | | | | | | | | | | | | | | | | |
| $R_1$ = OC$_2$H$_5$ | 1.12 | 2 | 8 | — | 9 | 9 | 5 | 9 | — | — | 9 | 9 | 9 | 9 | — | — | — | — | — | — | — | — | — | — |
| $R_2$ = Phenyl | 0.56 | 1 | 8 | — | 9 | 9 | 3 | 5 | 8 | — | 9 | 9 | 9 | 8 | — | — | — | — | — | — | — | — | — | — |
| $R_3$ = 3-Chlorophenyl | 0.28 | 1 | 0 | — | 6 | 9 | 2 | 3 | — | — | 9 | 9 | 9 | 8 | — | — | — | — | — | — | — | — | — | — |
| T (1/99) | | | | | | | | | | | | | | | | | | | | | | | | |
| $R_1$ = OC$_2$H$_5$ | 11.2 | 0 | 0 | — | 7 | 0 | 0 | 2 | 1 | — | 9 | 8 | 9 | 9 | — | — | — | 0 | — | — | — | — | — | 0 |
| $R_2$ = p-Dimethylaminophenyl | 2.0 | 6 | — | — | 2 | 7 | — | 2 | 2 | — | 6 | 6 | 8 | 2 | — | — | — | — | 2 | — | — | — | — | — |
| $R_3$ = Phenyl | | | | | | | | | | | | | | | | | | | | | | | | |
| E + T (62/38) | | | | | | | | | | | | | | | | | | | | | | | | |
| $R_1$ = OC$_2$H$_5$ | 11.2 | 5 | 5 | — | 8 | 7 | 0 | 3 | 7 | — | 0 | 0 | 6 | 7 | — | — | — | — | — | — | — | — | — | — |
| $R_2$ = Phenyl | | | | | | | | | | | | | | | | | | | | | | | | |
| $R_3$ = p-Methoxyphenyl | | | | | | | | | | | | | | | | | | | | | | | | |
| E (95/5) | | | | | | | | | | | | | | | | | | | | | | | | |
| $R_1$ = OH | 11.2 | 8 | 9 | — | 8 | 9 | — | 9 | 8 | — | 9 | 9 | 9 | 9 | — | — | — | 7 | 7 | 5 | — | — | — | 8 |
| $R_2$ = Phenyl | 2.0 | 6 | — | — | 8 | 9 | 2 | 8 | 9 | — | 9 | 9 | 9 | 9 | — | — | — | 3 | 5 | 0 | — | — | — | 1 |
| $R_3$ = 4-[3,4(Methylene- | 1.0 | 5 | — | — | 7 | 3 | — | 5 | 7 | — | 9 | 9 | 9 | 7 | — | — | — | 3 | — | 0 | — | — | — | 0 |
| dioxy)phenyl]-3-phenyl | 0.5 | 2 | — | — | 7 | 0 | — | 0 | 6 | — | 8 | 8 | 5 | 0 | — | — | — | 0 | — | 0 | — | — | — | — |
| E + T (59/41) | | | | | | | | | | | | | | | | | | | | | | | | |
| $R_1$ = OH · NH(n-C 3H$_7$)$_2$ | 11.2 | 9 | 9 | — | 9 | 9 | — | 8 | 8 | — | 9 | 6 | 9 | 9 | — | — | — | — | — | — | — | — | — | — |

TABLE I-continued

Preemergence Herbicidal Activity of Polysubstituted Acids and Derivatives having the Formula:

$$N\equiv C-CH-CH-CH_2-CO-R_1$$
$$\phantom{N\equiv C-CH}|\phantom{CH-}|$$
$$\phantom{N\equiv C-CH-CH-CH-CH}R_3\phantom{-}R_2$$

| Structure | Rate kg/ha | PN | SE | LA | MU | PI | RW | MG | VL | TB | BA | CR | FO | WO | DB | CH | CG | CN | SY | AN | NG | ER | BB | ST |
|---|---|---|---|---|---|---|---|---|---|---|---|---|---|---|---|---|---|---|---|---|---|---|---|---|
| $R_2$ = Phenyl<br>$R_3$ = Phenyl<br>E + T | | | | | | | | | | | | | | | | | | | | | | | | | |
| $R_1$ = OC$_2$H$_5$<br>$R_2$ = 3-Chloro-4-fluorophenyl<br>$R_3$ = Phenyl<br>E + T<br>(63/32) | 11.2<br>2.0<br>1.0 | 6<br>3<br>0 | 8<br>—<br>— | —<br>—<br>— | 9<br>8<br>8 | 9<br>9<br>9 | 7<br>0<br>0 | 0<br>0<br>0 | 7<br>5<br>2 | —<br>—<br>— | 9<br>6<br>2 | 9<br>7<br>2 | 9<br>8<br>5 | 9<br>3<br>0 | —<br>—<br>— | —<br>—<br>— | —<br>—<br>— | —<br>0<br>0 | —<br>0<br>0 | —<br>0<br>0 | —<br>—<br>— | —<br>—<br>— | —<br>—<br>— | —<br>3<br>0 |
| $R_1$ = OC$_2$H$_5$<br>$R_2$ = m-Nitrophenyl<br>$R_3$ = 3,5-Dichlorophenyl<br>E + T<br>(77/23) | 11.2<br>2.0<br>1.0 | 2<br>0<br>0 | 0<br>—<br>— | —<br>—<br>— | 8<br>0<br>0 | 9<br>0<br>0 | 9<br>0<br>— | 0<br>0<br>0 | 2<br>0<br>0 | —<br>—<br>— | 9<br>8<br>7 | 9<br>9<br>9 | 8<br>5<br>0 | 9<br>2<br>0 | —<br>—<br>— | —<br>—<br>— | —<br>—<br>— | —<br>0<br>0 | —<br>0<br>0 | —<br>1<br>0 | —<br>—<br>— | —<br>—<br>— | —<br>—<br>— | —<br>1<br>0 |
| $R_1$ = OC$_2$H$_5$<br>$R_2$ = m-Nitrophenyl<br>$R_3$ = 3,5-Dichlorophenyl<br>T<br>(5/95) | 11.2<br>2.0<br>1.0 | 2<br>0<br>0 | 0<br>—<br>— | —<br>—<br>— | 8<br>7<br>1 | 9<br>0<br>0 | 9<br>0<br>0 | 0<br>0<br>0 | 3<br>0<br>0 | —<br>—<br>— | 9<br>9<br>9 | 9<br>9<br>9 | 9<br>9<br>8 | 9<br>9<br>8 | —<br>—<br>— | —<br>—<br>— | —<br>—<br>— | —<br>3<br>0 | —<br>0<br>0 | —<br>3<br>1 | —<br>—<br>— | —<br>—<br>— | —<br>—<br>— | —<br>3<br>0 |
| $R_1$ = OH . (CH$_3$)$_2$NH<br>$R_2$ = m-Chlorophenyl<br>$R_3$ = Phenyl<br>E + T<br>(65/35) | 11.2<br>2.0<br>1.0 | 9<br>9<br>3 | 9<br>—<br>— | —<br>—<br>— | 9<br>9<br>9 | 9<br>8<br>7 | 9<br>3<br>0 | 9<br>3<br>0 | 9<br>8<br>8 | —<br>—<br>— | 9<br>9<br>9 | 9<br>8<br>7 | 9<br>9<br>9 | 9<br>8<br>8 | —<br>—<br>— | —<br>—<br>— | —<br>—<br>— | —<br>5<br>3 | —<br>5<br>0 | —<br>5<br>3 | —<br>—<br>— | —<br>—<br>— | —<br>—<br>— | —<br>7<br>5 |
| $R_1$ = OH . 1,1,3,3-Tetra-<br>methylbutyl amine<br>$R_2$ = Phenyl<br>$R_3$ = Phenyl<br>E + T | 11.2<br>2.0<br>1.0 | 9<br>9<br>5 | 8<br>—<br>— | —<br>—<br>— | 8<br>8<br>7 | 9<br>3<br>0 | —<br>3<br>0 | 8<br>7<br>7 | 8<br>8<br>8 | —<br>—<br>— | 9<br>9<br>9 | 3<br>0<br>0 | 8<br>9<br>9 | 9<br>8<br>3 | —<br>—<br>— | —<br>—<br>— | —<br>—<br>— | —<br>5<br>3 | —<br>6<br>5 | —<br>3<br>3 | —<br>—<br>— | —<br>—<br>— | —<br>—<br>— | —<br>8<br>7 |
| $R_1$ = OH<br>$R_2$ = p-Dimethylaminophenyl<br>$R_3$ = Phenyl<br>E + T | 11.2<br>2.0<br>1.0 | 0<br>0<br>0 | 4<br>—<br>— | —<br>—<br>— | 9<br>8<br>8 | 6<br>8<br>5 | 2<br>0<br>0 | 6<br>0<br>0 | 8<br>8<br>3 | —<br>—<br>— | 6<br>9<br>8 | 0<br>0<br>0 | 9<br>8<br>3 | 0<br>9<br>0 | —<br>—<br>— | —<br>—<br>— | —<br>—<br>— | —<br>0<br>0 | —<br>0<br>0 | —<br>0<br>0 | —<br>—<br>— | —<br>—<br>— | —<br>—<br>— | —<br>7<br>3 |
| $R_1$ = OH<br>$R_2$ = m-Nitrophenyl<br>$R_3$ = 3,5-Dichlorophenyl<br>E + T<br>$R_1$ = OH<br>$R_2$ = 3-Chloro-4-fluorophenyl<br>$R_3$ = Phenyl<br>E + T<br>(60/40) | 11.2<br>2.0<br>1.0<br>0.5<br>11.2<br>2.0<br>1.0 | 2<br>0<br>0<br>0<br>6<br>—<br>0 | 8<br>—<br>—<br>—<br>8<br>—<br>— | —<br>—<br>—<br>—<br>—<br>—<br>— | 9<br>8<br>8<br>9<br>9<br>9<br>8 | 9<br>7<br>7<br>7<br>9<br>3<br>0 | 7<br>0<br>0<br>0<br>2<br>0<br>0 | 7<br>0<br>0<br>0<br>0<br>0<br>0 | 8<br>0<br>0<br>0<br>8<br>7<br>7 | —<br>—<br>—<br>—<br>—<br>—<br>— | 9<br>9<br>8<br>7<br>8<br>8<br>8 | 9<br>9<br>9<br>7<br>9<br>8<br>5 | 9<br>8<br>6<br>5<br>9<br>9<br>8 | 9<br>9<br>7<br>0<br>9<br>8<br>7 | —<br>—<br>—<br>—<br>—<br>—<br>— | —<br>—<br>—<br>—<br>—<br>—<br>— | —<br>—<br>—<br>—<br>—<br>—<br>— | —<br>7<br>3<br>0<br>—<br>3<br>2 | —<br>0<br>0<br>0<br>—<br>3<br>0 | —<br>7<br>0<br>0<br>—<br>0<br>0 | —<br>—<br>—<br>—<br>—<br>—<br>— | —<br>—<br>—<br>—<br>—<br>—<br>— | —<br>—<br>—<br>—<br>—<br>—<br>— | —<br>3<br>3<br>—<br>5<br>3 |
| $R_1$ = OC$_2$H$_5$<br>$R_2$ = Phenyl<br>$R_3$ = o-Fluorophenyl | 11.2 | 6 | 8 | — | 9 | 9 | 6 | 3 | 8 | — | 9 | 2 | 9 | 7 | — | — | — | — | — | — | — | — | — | — |

TABLE I-continued

Preemergence Herbicidal Activity of Polysubstituted Acids and Derivatives having the Formula:

$$N\equiv C-\underset{R_2}{\underset{|}{C}}H-\underset{R_3}{\underset{|}{C}}H-CH_2-CO-R_1$$

| Structure | Rate kg/ha | PN | SE | LA | MU | PI | RW | MG | VL | TB | BA | CR | FO | WO | DB | CH | CG | CN | SY | AN | NG | ER | BB | ST |
|---|---|---|---|---|---|---|---|---|---|---|---|---|---|---|---|---|---|---|---|---|---|---|---|---|
| $R_1$ = OC$_2$H$_5$<br>$R_2$ = 3,4-Difluorophenyl<br>$R_3$ = Phenyl<br>E + T | 11.2 | 9 | 8 | — | 9 | 9 | 3 | 0 | 8 | — | 9 | 8 | 9 | 9 | — | — | — | — | — | — | — | — | — | — |
| $R_1$ = OH . NH$_3$<br>$R_2$ = Phenyl<br>$R_3$ = Phenyl<br>E + T | 11.2 | 9 | 8 | — | 9 | 9 | 8 | 9 | 8 | — | 9 | 2 | 9 | 9 | — | — | — | — | — | — | — | — | — | — |
| $R_1$ = OH . CH$_3$NH$_2$<br>$R_2$ = Phenyl<br>$R_3$ = Phenyl<br>E + T | 11.2 | 9 | 9 | — | 9 | 9 | 5 | 8 | 8 | — | 9 | 2 | 9 | 9 | — | — | — | — | — | — | — | — | — | — |
| $R_1$ = OH<br>$R_2$ = Phenyl<br>$R_3$ = o-Fluorophenyl<br>E + T | 11.2 | 8 | 8 | — | 9 | 8 | 2 | 7 | 8 | — | 8 | 2 | 8 | 8 | — | — | — | — | — | — | — | — | — | — |

*Average 2 or more tests.
E = Erythro, which means that at least 80%, by weight, of the compound is the erythro isomer.
T = Threo, which means that at least 80%, by weight, of the compound is the threo isomer.
E + T = Erythro/Threo mixture, which means it contains any combination of isomers which is present in an amount less than 80% of either of the isomers.

EXAMPLE 16

Postemergence Herbicidal Activity

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in separate cups for about 2 weeks. The test compounds are dispersed in 50/50 acetone/water mixtures containing 0.1% of a spreader activator such as an alkylaryl polyoxyethylene glycol plus free fatty acid and isopropanol, in sufficient quantity to provide the equivalent of about 0.017 kg to 11.2 kg per hectare of active compound when applied to the plants through a spray nozzle operating a 2.81 kg/cm$^2$ pressure for a predetermined time. After spraying, the plants are placed on greenhouse benches and are cared for in the usual manner, commensurate with conventional greenhouse practices. Two to five weeks after treatment, the seedling plants are examined and rated according to the rating system set forth in Example 15. The data obtained are reported in Table II below.

TABLE II

Postemergence Herbicidal Activity of Polysubstituted Acids and Derivatives having the Formula:

$$N\equiv C-CH-CH-CH_2-CO-R_1$$
$$\phantom{N\equiv C-}\overset{|}{R_3}\phantom{-CH}\overset{|}{R_2}$$

| Structure | Rate kg/ha | N | SE | LA | MU | PI | RW | MG | VL | TB | BA | CR | FO | WO | BG | CH | CG | CN | SY | AN | NG | ER | BB | ST |
|---|---|---|---|---|---|---|---|---|---|---|---|---|---|---|---|---|---|---|---|---|---|---|---|---|
| *R$_1$ = OH | 2.24 | — | — | 1.0 | 8.5 | — | — | — | — | 7.5 | 6.3 | 0 | 7.0 | 8.5 | 7.4 | 8.7 | 7.5 | 0 | — | 2.1 | 4.0 | 3.7 | 3.0 | 8.0 |
| R$_2$ = Phenyl | 1.12 | — | — | 2.8 | 5.6 | — | — | — | — | 6.3 | 2.8 | 0 | 4.8 | 8.3 | 4.9 | 8.4 | 7.4 | 1.2 | — | 0.9 | 1.6 | 2.8 | 0.7 | 5.6 |
| R$_3$ = Phenyl | 0.56 | — | — | 1.3 | 1.5 | — | — | — | — | 5.7 | 1.1 | 0 | 3.0 | 7.8 | 4.8 | 6.8 | 7.0 | 0 | — | 0.4 | 0.9 | 2.0 | 0.4 | 5.6 |
| E + T | 0.28 | — | — | 0.5 | 0 | — | — | — | 6 | 3.8 | 0.1 | 0 | 2.1 | 8.0 | 2.0 | 5.7 | 6.6 | 0 | 6 | 0.7 | 0.5 | 1.2 | 0 | 5.3 |
| *R$_1$ = OH | 1.12 | 5 | 7 | 7 | 7 | 5 | 6 | — | 6 | 8.5 | 6.6 | 0 | 8 | 9 | 8.5 | 8 | 7 | 5 | 6 | 6 | 8.5 | 1.6 | 2.2 | 9 |
| R$_2$ = Phenyl | 0.56 | 3 | 5 | 6 | 6 | 5 | 4 | 6 | 4.5 | 8.5 | 6.6 | 3 | 8 | 9 | 8.5 | 8 | 7 | 5 | 6 | 5 | 8 | 7 | 3 | 3 | 9 |
| R$_3$ = Phenyl | 0.28 | 2 | 3 | 5 | 5 | 5 | 0 | 1 | 3 | 8 | 5.3 | 0 | 8 | 9 | 5.5 | 8 | 7 | 3.5 | 3 | 3 | 7 | 3.3 | 3 | 2.2 | 9 |
| T | 0.14 | — | — | 5 | 3 | — | — | — | — | 8 | 5.5 | 3 | 7.5 | 9 | 4.5 | 8 | 7 | 1 | — | 5 | 5.5 | 2.2 | 2 | 2.1 | 9 |
| (74/26) | 0.07 | — | — | 4 | 4 | — | — | — | — | 7 | 5 | 0 | 6 | 8.5 | 3.5 | 7 | 6 | 0 | — | — | 5 | 1.4 | — | — | 8 |
| *R$_1$ = OC$_2$H$_5$ | 4.48 | — | — | — | 7 | — | — | — | — | 6 | 6 | 3 | 6 | 9 | — | 8 | — | 6 | 7 | — | — | 7 | — | — | — |
| R$_2$ = Phenyl | 1.12 | — | — | — | 2 | 2 | 0 | 0 | 2 | — | 1 | 3 | 3 | 8.5 | — | — | — | 6 | 5 | 6.5 | — | 6.5 | — | — | 6.5 |
| R$_3$ = 4-Chlorophenyl | 0.56 | — | — | — | 2 | 0 | 0 | 0 | 0 | 1 | 0 | 8 | 6 | 9 | — | 6 | — | — | — | — | — | 5.5 | — | — | — |
| E + T | 0.28 | — | — | — | — | — | — | — | — | — | — | — | 5 | — | — | — | — | — | — | — | — | — | — | — | 6 |
| *R$_1$ = OC$_2$H$_5$ | 2.24 | 0 | — | 3 | 8 | — | — | — | — | 9 | 8 | 7 | 8 | 9 | 9 | 7 | — | 7 | — | — | 3 | 9 | 9 | 9 |
| R$_2$ = Phenyl | 1.12 | 0 | — | 1 | 7.5 | — | — | — | — | 3 | 8 | 4.5 | 7.5 | 9 | 8 | 7 | 8 | 7 | — | — | 0 | 9 | 9 | 8 |
| R$_3$ = 3-Chlorophenyl | 0.56 | 0 | — | 1 | 5.5 | 5 | — | — | — | 3 | 8 | 3 | 4.5 | 9 | 9 | 7 | 8 | 7 | 5 | — | 0 | 0 | 0 | 9 | 5 |
| E + T | 0.28 | 0 | — | — | 1 | — | — | — | — | — | 7 | 7 | 0 | 1.5 | 9 | 2 | 3 | 8 | — | — | — | — | 1 | — | — |
| (74/26) | 0.07 | — | — | — | 4 | — | — | — | — | 2 | 3 | 0 | 0 | 9 | 0 | 3 | 7 | — | — | — | — | — | — | — | — |
| *R$_1$ = OC$_2$H$_5$ | 1.12 | 3 | — | 7 | 9 | — | — | — | — | 8 | 8.5 | 8.5 | 8 | 9 | 8 | 9 | 9 | 8 | — | — | 9 | 9 | — | 9 | 9 |
| R$_2$ = Phenyl | 0.56 | 0 | — | 6 | 9 | — | — | — | — | 9 | 8.5 | 8.5 | 8 | 9 | 8 | 9 | 7 | 8 | — | — | 9 | 9 | — | 3 | 9 |
| R$_3$ = 3-Chlorophenyl | 0.14 | 0 | — | 5 | 8 | — | — | — | — | 8 | 8.5 | 7 | 8 | 9 | 8 | 9 | 7 | 8 | — | — | 8 | 5 | — | 3 | 9 |
| E + T | 0.035 | — | — | 0 | 2 | — | — | — | — | 2 | 7 | 3 | 7 | 9 | 0 | 9 | 7 | — | — | — | — | — | — | — | 9 |
| (1/99) | 0.017 | — | — | 0 | 2 | — | — | — | — | 2 | 7 | 0 | 5 | 9 | 0 | 9 | 5 | 6 | 5 | — | — | — | — | — | — |
| R$_1$ = OC$_2$H$_5$ | 2.24 | 0 | — | 2 | 9 | — | — | — | — | 5 | 8 | 0 | 0 | 9 | — | 8 | — | 7 | — | — | — | 8 | 3 | 7 |
| R$_2$ = Phenyl | 1.12 | 0 | — | 2 | 5 | — | — | — | — | 5 | 6 | 0 | 0 | 9 | — | 6 | — | 6 | — | — | — | 9 | 3 | 7 |
| R$_3$ = 3-Pyridyl | 0.56 | 0 | — | 2 | 5 | — | — | — | 8 | 5 | 0 | 0 | 0 | 9 | — | — | — | — | — | — | — | 9 | 9 | 7 |
| E + T | | | | | | | | | | | | | | | | | | | | | | | | | |
| (58/42) | | | | | | | | | | | | | | | | | | | | | | | | | |
| R$_1$ = OC$_2$H$_5$ | 11.2 | 7 | — | — | 8 | — | — | — | — | — | 7 | 4 | 7 | 9 | — | — | — | — | — | — | — | — | — | — |
| R$_2$ = 4-Methylphenyl | 2.24 | 0 | — | 2 | 8 | — | — | — | — | — | 8 | 0 | 8 | 2 | — | 6 | — | 3 | — | — | — | 9 | 0 | 7 |
| R$_3$ = Phenyl | 1.12 | 0 | — | 2 | 8 | — | — | — | — | — | 7 | 0 | 8 | 7 | — | 5 | — | 3 | — | — | — | 9 | 0 | 7 |
| E + T | 0.56 | 0 | — | 2 | 8 | — | — | — | — | — | 3 | 0 | 3 | 0 | — | 0 | — | 0 | — | — | — | 7 | 0 | 7 |
| (51/49) | | | | | | | | | | | | | | | | | | | | | | | | | |
| R$_1$ = OH | 1.12 | 0 | — | 0 | 9 | — | — | — | — | 8 | 7 | 0 | 6 | 9 | 2 | 8 | 7 | 0 | — | — | 7 | 8 | 0 | 7 |
| R$_2$ = Phenyl | 0.56 | 0 | — | 0 | 7 | — | — | — | — | 8 | 8 | 0 | 3 | 9 | 2 | 8 | 7 | 0 | — | — | 3 | 9 | 0 | 7 |
| R$_3$ = 3-Chlorophenyl | 0.28 | 0 | — | 0 | 3 | — | — | — | — | 8 | 6 | 0 | 3 | 9 | 0 | 8 | 7 | 0 | — | — | 3 | 9 | 0 | 5 |
| EtO·&T | 0.14 | — | — | 0 | 2 | — | — | — | — | 3 | 3 | 0 | 3 | 9 | — | 8 | — | 0 | — | — | 0 | 5 | 0 | — |
| (67/33) | | | | | | | | | | | | | | | | | | | | | | | | | |
| R$_1$ = OCH$_3$ | 1.12 | 0 | — | 0 | 6 | — | — | — | — | 3 | 0 | 0 | 3 | 9 | — | — | — | 0 | — | — | — | 9 | 7 | 9 |
| | 0.56 | 0 | — | 0 | 3 | — | — | — | — | 3 | 0 | 0 | 1 | 9 | — | — | — | 0 | — | — | — | 7 | 0 | 8 |
| R$_2$ = Phenyl | 0.28 | 0 | — | 0 | 2 | — | — | — | — | 3 | 0 | 0 | 0 | 9 | — | — | — | 0 | — | — | — | 7 | 0 | 8 |

TABLE II-continued

Postemergence Herbicidal Activity of Polysubstituted Acids and Derivatives having the Formula:

$$N\equiv C-CH-CH-CH_2-CO-R_1$$
$$\phantom{N\equiv C-CH-}\,|\phantom{CH-CH_2-CO-}|$$
$$\phantom{N\equiv C-CH-}R_3\phantom{-CH-}R_2$$

| Structure | Rate kg/ha | N | SE | LA | MU | PI | RW | MG | VL | TB | BA | CR | FO | WO | BG | CH | CG | CN | SY | AN | NG | ER | BB | ST |
|---|---|---|---|---|---|---|---|---|---|---|---|---|---|---|---|---|---|---|---|---|---|---|---|---|
| R₃ = Phenyl E + T (68/32) | 0.14 | 0 | — | 0 | 0 | — | — | — | — | 3 | 0 | 0 | 0 | 9 | — | — | — | 0 | — | — | — | 7 | 0 | 8 |
| R₁ = OC₂H₅ | 1.12 | 0 | — | 0 | 0 | — | — | — | — | 6 | 0 | 0 | 0 | 9 | — | — | — | 0 | — | — | — | 8 | 0 | 9 |
|  | 0.56 | 0 | — | 0 | 0 | — | — | — | — | 6 | 0 | 0 | 0 | 9 | — | — | — | 0 | — | — | — | 7 | 0 | 9 |
| R₂ = Phenyl | 0.28 | 0 | — | 0 | 0 | — | — | — | — | 5 | 0 | 0 | 0 | 9 | — | — | — | 0 | — | — | — | 6 | 0 | 9 |
| R₃ = Phenyl E + T (74/26) | 0.07 | 0 | — | 0 | 0 | — | — | — | — | 3 | 0 | 0 | 0 | 9 | — | — | — | 0 | — | — | — | 6 | 0 | 9 |
| R₁ = OCH(CH₃)₂ | 1.12 | 0 | — | 0 | 0 | — | — | — | — | — | 0 | 0 | 1 | 9 | — | — | — | 0 | — | — | — | 9 | 0 | 9 |
|  | 0.56 | 0 | — | 0 | 0 | — | — | — | — | — | 0 | 0 | 1 | 9 | — | — | — | 0 | — | — | — | 9 | 0 | 9 |
| R₂ = Phenyl | 0.28 | 0 | — | 0 | 0 | — | — | — | — | — | 0 | 0 | 1 | 9 | — | — | — | 0 | — | — | — | 8 | 0 | 9 |
| R₃ = Phenyl E + T (69/31) | 0.07 | 0 | — | 0 | 0 | — | — | — | — | — | 0 | 0 | 0 | 8 | — | — | — | 0 | — | — | — | 9 | 0 | 3 |
| R₁ = OC₂H₅ | 1.12 | 0 | — | — | 9 | — | — | — | — | 7 | 3 | 6 | 7 | 9 | 9 | 9 | — | 8 | — | — | — | 9 | 9 | 9 |
|  | 0.45 | 0 | — | — | 7 | — | — | — | — | 6 | 3 | 5 | 7 | 9 | 9 | 9 | — | 8 | — | — | — | 9 | 9 | 9 |
| R₂ = 3-Nitrophenyl | 0.14 | 0 | — | — | 6 | — | — | — | — | 1 | 0 | 0 | 0 | 9 | 5 | 9 | — | 6 | — | — | — | 3 | 9 | 3 |
| R₃ = Phenyl T (3/97) | 0.07 | 0 | — | — | 6 | — | — | — | — | 1 | 0 | 0 | 0 | 9 | 2 | 9 | — | 6 | — | — | — | 3 | 8 | 3 |
| *R₁ = OC₂H₅ | 1.12 | 5 | — | — | 3 | — | — | — | — | 3 | 2 | 0 | 2 | 9 | 5 | 9 | — | 0 | — | — | — | 9 | 0 | 8 |
|  | 0.56 | 0 | — | — | 3 | — | — | — | — | 3 | 1 | 0 | 2 | 9 | 3 | 8 | — | 0 | — | — | — | 8 | 0 | 7 |
| R₂ = 3-Chlorophenyl | 0.14 | 0 | — | — | 0 | — | — | — | — | 3 | 0 | 0 | 0 | 9 | 5 | 5 | — | 0 | — | — | — | 3 | 0 | 3 |
| R₃ = Phenyl E + T (30/70) | 0.07 | 0 | — | — | 0 | — | — | — | — | 3 | 0 | 0 | 0 | 8 | 2 | 3 | — | 0 | — | — | — | 3 | 0 | 3 |
| *R₁ = OH | 1.12 | 3.3 | — | 2.5 | 8.5 | — | — | — | — | 6.3 | 1 | 0 | 5.3 | 8 | 5 | 9 | — | 2.3 | — | 0 | 2 | 1 | 1.5 | 0 |
| R₂ = 3-Chlorophenyl | 0.56 | 0 | — | 2 | 7 | 5 | 0 | 0 | 2 | 6.3 | 0 | 0 | 3 | 8.6 | 3 | 4.5 | — | 1 | — | 0 | 0 | 0 | 0 | 0 |
| R₃ = Phenyl | 0.07 | 0 | — | 0 | 1.5 | 0 | 0 | 0 | 0 | 4.6 | 0 | 0 | 2 | 8 | 0 | 4 | — | 0 | — | 0 | 0 | 0 | 0 | 0 |
| E + T (66/34) | 0.035 | 0 | — | 0 | 0 | 0 | 0 | 0 | 0 | 2.3 | 0 | 0 | 0 | 6.3 | 0 | 4 | — | 0 | — | 0 | 0 | 0 | 0 | 0 |
| *R₁ = OC₂H₅ | 1.12 | 0 | — | 0 | 5.5 | 5 | 0 | 0 | 2 | 4 | 2.6 | 0 | 3.3 | 6.4 | 3 | 7.6 | 9 | 2.3 | 0 | 3.4 | 0 | 1 | 3 | 3 |
|  | 0.56 | 0 | — | 0 | 0 | 0 | 0 | 0 | 0 | 3.7 | 1 | 0 | 2.6 | 5.5 | 2.6 | 3.3 | 7 | 1.6 | 0 | 2.3 | 0 | 0 | 0 | 2.4 |
| R₂ = 4-Chlorophenyl | 0.28 | 0 | — | 0 | 0 | 0 | 0 | 0 | 0 | 0.8 | 0 | 0 | 0 | 5.5 | 0.8 | 0.8 | 7 | 0.8 | 0 | 1.7 | 0 | 0 | 0 | 2 |
| R₃ = Phenyl E (95/5) | 0.14 | 0 | — | 0 | 0 | 0 | 0 | 0 | 0 | 0.8 | 0 | 0 | 0 | 4.7 | 0 | 0 | 7 | 0 | 0 | 1 | 0 | 0 | 0 | 1 |
| *R₁ = OC₂H₅ | 2.24 | 3 | — | 7 | 9 | — | — | — | — | 8 | 8 | 8 | 8 | 8 | 9 | 8 | 9 | 8 | 7 | — | — | 5 | — | — |
|  | 1.12 | 0 | — | 7 | 9 | — | — | — | — | 7.5 | 5 | 0 | 8 | 9 | 5.6 | 8.5 | 8 | 7 | — | 9 | 5 | — | 9 | 8.5 |
| R₂ = Phenyl | 0.56 | 0 | — | 5.5 | 7.5 | — | — | — | — | 7.5 | 3 | 0 | 8 | 9 | 4 | 6.5 | 8 | 7 | — | 9 | 5 | — | 9 | 8 |
| R₃ = Phenyl T (3/97) | 0.28 | 0 | — | 5 | 1.5 | — | — | — | — | 5.5 | 0 | 0 | 7 | 8 | 4 | 6.5 | 8 | 3 | — | 8 | 5 | — | 7 | 8.5 |
| *R₁ = OH . NH(CH₃)₂ | 1.12 | 0 | — | 4 | 3 | — | — | — | — | 4 | 0 | 0 | 4 | 8.2 | 5.6 | 7 | — | 0 | — | 2.2 | 1 | 0 | 2 | 3.6 |

TABLE II-continued

Postemergence Herbicidal Activity of Polysubstituted Acids and Derivatives having the Formula:

$$N\equiv C-CH-CH-CH_2-CO-R_1$$
$$\quad\quad\quad\;\;|\;\;\;\;\;\;\;|$$
$$\quad\quad\quad\;R_3\;\;R_2$$

| Structure | Rate kg/ha | N | SE | LA | MU | PI | RW | MG | VL | TB | BA | CR | FO | WO | BG | CH | CG | CN | SY | AN | NG | ER | BB | ST |
|---|---|---|---|---|---|---|---|---|---|---|---|---|---|---|---|---|---|---|---|---|---|---|---|---|
| $R_2$ = Phenyl | 0.45 | 0 | — | 1.5 | 0.5 | — | — | — | — | 3 | 0 | 0 | 3.3 | 8.2 | 5.6 | 7.5 | — | 0 | — | 1.8 | 0.8 | 0 | 0 | 2 |
| $R_3$ = Phenyl | 0.28 | 0 | — | 0 | 0 | — | — | — | — | 1.5 | 0 | 0 | 0.6 | 8 | 4.3 | 4 | — | 0 | — | 1.8 | 0.3 | 0 | 0 | 0.8 |
| E + T | 0.14 | 0 | — | 0 | 0 | — | — | — | — | 1.5 | 0 | 0 | 0 | 6.3 | 4.2 | 2.5 | — | 0 | — | 0 | 0 | 0 | 0 | 0 |
| (67/33) | | | | | | | | | | | | | | | | | | | | | | | | |
| $R_1$ = ONa . ½H$_2$O | 1.12 | 0 | — | 3 | 9 | — | — | — | — | 7 | 0 | 0 | 7 | 9 | 0 | 9 | — | 2 | — | 7 | — | — | 5 | 5 |
| | 0.56 | 0 | — | 3 | 5 | — | — | — | — | 2 | 0 | 0 | 5 | 9 | 0 | 9 | — | 0 | — | 7 | — | — | 3 | 5 |
| $R_2$ = Phenyl | 0.28 | 0 | — | 0 | 0 | — | — | — | — | 2 | 0 | 0 | 5 | 8 | 0 | 9 | — | 0 | — | 3 | — | — | 2 | 3 |
| $R_3$ = Phenyl | 0.14 | 0 | — | 0 | 0 | — | — | — | — | 2 | 0 | 0 | 6 | 8 | 0 | 9 | — | 0 | — | 5 | — | — | 0 | 5 |
| E + T (40/60) | | | | | | | | | | | | | | | | | | | | | | | | |
| *$R_1$ = OH | 1.12 | 1 | — | 2.6 | 7.6 | — | — | — | — | 6.6 | 1 | 2.6 | 3.3 | 8.6 | 8.6 | 8 | 7 | 6.5 | — | 5.5 | 4.3 | — | — | 7.3 |
| $R_2$ = 4-Chlorophenyl | 0.56 | 0 | — | 3 | 6.9 | — | — | — | — | 6.6 | 1 | 0 | 0.8 | 8.6 | 8.6 | 7 | 7 | 2.5 | — | 4.3 | 3 | — | — | 7.3 |
| $R_3$ = Phenyl | 0.07 | 0 | — | 0.8 | 0 | — | — | — | — | 2.3 | 1 | 0 | 0 | 6.6 | 1.5 | 0.8 | 5 | 0.5 | — | 1 | 0.8 | — | — | 2 |
| E + T (69/31) | 0.035 | 0 | — | 0 | 0 | — | — | — | — | 0 | 1 | 0 | 0 | 5 | 0 | 2.5 | 3 | 0 | — | 0 | 0 | — | — | 0.3 |
| *$R_1$ = OH | 1.12 | 6 | — | 8 | 9 | — | — | — | — | 8.6 | 7.6 | 1.6 | 7.3 | 9 | 8.6 | 9 | 7 | 7.5 | — | 9 | 8.6 | — | — | 9 |
| $R_2$ = 4-Chlorophenyl | 0.28 | 0.5 | — | 7.5 | 8.5 | — | — | — | — | 8 | 5.6 | 0.8 | 4.3 | 9 | 8.6 | 8.6 | 7 | 7 | — | 9 | 7.6 | — | — | 8.6 |
| $R_3$ = Phenyl | 0.07 | 0 | — | 3 | 7 | — | — | — | — | 7 | 4.5 | 0 | 1 | 9 | 8.6 | 5.5 | 7 | 1 | — | 1.5 | 3.5 | — | — | 8.5 |
| T (12/88) | 0.018 | 0 | — | 2 | 5 | — | — | — | — | 1 | 3 | 0 | 0 | 7 | 3 | 4.5 | 6 | — | — | — | — | — | — | 0.8 |
| *$R_1$ = OC$_2$H$_5$ | 1.12 | 0 | — | 0 | 7.6 | — | — | — | — | 8.6 | 2.3 | 0 | 2.6 | 9 | 8.6 | 7.6 | 9 | 6.5 | — | 8.5 | 8 | — | — | 8.6 |
| $R_2$ = 4-Chlorophenyl | 0.28 | 0 | — | 0 | 4.3 | — | — | — | — | 6.6 | 1 | 0 | 0 | 9 | 8.3 | 8.6 | 7 | 5.5 | — | 5 | 5 | — | — | 7.3 |
| $R_3$ = Phenyl | 0.07 | 0 | — | 0 | 0 | — | — | — | — | 2.3 | 0 | 0 | 0 | 8 | 2.6 | 5 | 5 | 2.5 | — | 0 | 0.6 | — | — | 4.3 |
| E + T (77/23) | 0.035 | 0 | — | 0 | 0 | — | — | — | — | 0.7 | 0 | 0 | 0 | 7 | 2.6 | 1 | 5 | 0 | — | 0 | 0 | — | — | 3.6 |
| *$R_1$ = OC$_2$H$_5$ | 1.12 | 0 | — | 6 | 8 | — | — | — | — | 7 | 3 | 3 | 2.5 | 9 | 8 | 9 | 8 | 7 | — | 1 | 1.5 | 0 | 0 | 0.5 |
| $R_2$ = 3,5-Dichloro- | 0.28 | 0 | — | 3 | 3 | — | — | — | — | 5 | 0 | 0 | 2.5 | 8.6 | 7 | 8 | 8 | 7 | — | 0 | 0 | 0 | 0 | 0 |
| phenyl | 0.07 | 0 | — | 0 | 0 | — | — | — | — | 0 | 0 | 0 | 0 | 8.6 | 0 | 8 | 8 | 6 | — | 0 | 0 | 0 | 0 | 0 |
| $R_3$ = Phenyl E + T (60/40) | 0.035 | 0 | — | 0 | 0 | — | — | — | — | 0 | 0 | 0 | 0 | 7.6 | 0 | 3 | 6 | 3 | — | 0 | 0 | 0 | 0 | 0 |
| *$R_1$ = OLi . ½H$_2$O | 1.12 | 0 | — | 0 | 3 | — | — | — | — | 5 | 6 | 0 | 3.5 | 8.6 | 6.5 | 7 | 7 | 2 | — | 2.5 | 2 | 0 | 0 | 4.5 |
| $R_2$ = Phenyl | 0.56 | 0 | — | 0 | 0 | — | — | — | — | 3 | 0 | 0 | 3.5 | 8.6 | 2.5 | 3 | 6 | 0 | — | 1.5 | 0 | 0 | 0 | 4 |
| $R_3$ = Phenyl | 0.14 | 0 | — | 0 | 0 | — | — | — | — | 0 | 0 | 0 | 0 | 8.3 | 0 | 0 | 5 | 0 | — | 1 | 0 | 0 | 0 | 3.5 |
| E + T (71/29) | 0.07 | 0 | — | 0 | 0 | — | — | — | — | 0 | 0 | 0 | 0 | 7.6 | 0 | 0 | 2 | 0 | — | 1 | 0 | 0 | 0 | 1.5 |
| $R_1$ = OC$_2$H$_5$ | 1.12 | 3 | — | 3 | 8 | — | — | — | — | 6 | 3 | 0 | 0 | 9 | 8 | 8 | — | 6 | — | 7 | 5 | — | — | 8 |
| $R_2$ = 3-Trifluoro- | 0.56 | 0 | — | 0 | 7 | — | — | — | — | 5 | 0 | 0 | 0 | 9 | 9 | 8 | — | 1 | — | 8 | 5 | — | — | 9 |
| methylphenyl | 0.14 | 0 | — | 0 | 0 | — | — | — | — | 3 | 0 | 0 | 0 | 8 | 7 | 3 | — | 0 | — | 2 | 5 | — | — | 5 |
| $R_3$ = Phenyl T | 0.07 | 0 | — | 0 | 0 | — | — | — | — | 0 | 0 | 0 | 0 | 8 | 6 | 2 | — | 0 | — | 2 | 5 | — | — | 5 |
| $R_1$ = OCH$_2$CCl=CH$_2$ | 1.12 | 3 | — | 5 | 9 | — | — | — | — | 9 | 0 | 0 | 5 | 9 | 7 | 9 | — | 6 | — | 7 | 5 | — | — | 9 |
| | 0.56 | 2 | — | 2 | 5 | — | — | — | — | 9 | 0 | 0 | 5 | 9 | 0 | 9 | — | 3 | — | 6 | 3 | — | — | 9 |

TABLE II-continued

Postemergence Herbicidal Activity of Polysubstituted Acids and Derivatives having the Formula:

$$N\equiv C-CH-CH-CH_2-CO-R_1$$
$$\qquad\;\; |\quad\;\; |$$
$$\qquad\;\; R_3\;\;\; R_2$$

| Structure | Rate kg/ha | N | SE | LA | MU | PI | RW | MG | VL | TB | BA | CR | FO | WO | BG | CH | CG | CN | SY | AN | NG | ER | BB | ST |
|---|---|---|---|---|---|---|---|---|---|---|---|---|---|---|---|---|---|---|---|---|---|---|---|---|
| $R_2$ = Phenyl | 0.14 | 0 | — | 0 | 0 | — | — | — | — | 2 | 0 | 0 | 0 | 9 | 0 | 9 | — | 1 | — | 0 | 0 | — | — | 9 |
| $R_3$ = Phenyl | 0.018 | 0 | — | 0 | 0 | — | — | — | — | 0 | 0 | 0 | 0 | 8 | 0 | 8 | — | 0 | — | 0 | 0 | — | — | 8 |
| E + T (27/73) | | | | | | | | | | | | | | | | | | | | | | | | |
| $R_1$ = OH | 1.12 | 0 | — | 2 | 8 | — | — | — | — | 5 | 0 | 0 | 3 | 9 | 0 | 9 | — | 3 | — | 6 | 6 | — | — | 9 |
| $R_2$ = 3-Trifluoro- | 0.56 | 0 | — | 0 | 8 | — | — | — | — | 5 | 0 | 0 | 3 | 9 | 0 | 9 | — | 0 | — | 6 | 6 | — | — | 9 |
| methylphenyl | 0.28 | 0 | — | 0 | 8 | — | — | — | — | 3 | 0 | 0 | 0 | 9 | 0 | 3 | — | 0 | — | 6 | 5 | — | — | 9 |
| $R_3$ = Phenyl | 0.14 | 0 | — | 0 | 5 | — | — | — | — | 0 | 0 | 0 | 0 | 6 | 0 | 2 | — | 0 | — | 2 | 1 | — | — | 9 |
| E + T (50/50) | | | | | | | | | | | | | | | | | | | | | | | | |
| $R_1$ = $OC_2H_5$ | 2.24 | — | — | 7 | 9 | — | — | — | — | 8 | 8 | 9 | 8 | 9 | 9 | 9 | 9 | — | — | — | 8 | — | — | 9 |
| $R_2$ = Phenyl | 0.56 | — | — | 6 | 8 | — | — | — | — | 3 | 8 | 9 | 7 | 9 | 8 | 9 | 7 | — | — | — | 8 | — | — | 8 |
| $R_3$ = 3,5-Dichloro- | 0.14 | — | — | 2 | 5 | — | — | — | — | 1 | 8 | 9 | 3 | 9 | 8 | 8 | 5 | — | — | — | 8 | — | — | 7 |
| phenyl | 0.035 | — | — | 0 | 0 | — | — | — | — | 0 | 0 | 5 | 0 | 8 | 5 | 7 | 3 | — | — | — | 7 | — | — | 3 |
| T (5/95) | | | | | | | | | | | | | | | | | | | | | | | | |
| $R_1$ = $OC_2H_5$ | 1.12 | 0 | — | 2 | 0 | — | — | — | — | 0 | 0 | 0 | 0 | 8 | 5 | 7 | — | 3 | — | 2 | 5 | — | — | 8 |
| $R_2$ = 2-Chlorophenyl | 0.56 | 0 | — | 0 | 0 | — | — | — | — | 0 | 0 | 0 | 0 | 8 | 5 | 2 | — | 0 | — | 0 | 3 | — | — | 8 |
| $R_3$ = Phenyl | 0.28 | 0 | — | 0 | 0 | — | — | — | — | 0 | 0 | 0 | 0 | 7 | 0 | 0 | — | 0 | — | 0 | 0 | — | — | 8 |
| E + T (45/55) | | | | | | | | | | | | | | | | | | | | | | | | |
| $R_1$ = $OC_2H_5$ | 1.12 | 2 | — | 0 | 8 | — | — | — | — | 0 | 3 | 0 | 2 | 9 | 8 | 8 | — | 7 | — | 7 | 9 | — | — | 7 |
| $R_2$ = 4-Chlorophenyl | 0.56 | 2 | — | 0 | 8 | — | — | — | — | 0 | 3 | 0 | 2 | 9 | 8 | 8 | — | 6 | — | 7 | 9 | — | — | 8 |
| $R_3$ = 3-Chlorophenyl | 0.28 | 1 | — | 0 | 6 | — | — | — | — | 0 | 3 | 0 | 0 | 9 | 3 | 7 | — | 6 | — | 2 | 8 | — | — | 6 |
| E + T (70/30) | 0.14 | 0 | — | 0 | 5 | — | — | — | — | 0 | 0 | 0 | 0 | 8 | 3 | 2 | — | 6 | — | 1 | 7 | — | — | 5 |
| $R_1$ = $OC_2H_5$ | 1.12 | 0 | — | 0 | 8 | — | — | — | — | 0 | 0 | 0 | 3 | 8 | 0 | 7 | — | 5 | — | 2 | 5 | — | — | 8 |
| $R_2$ = 4-Chlorophenyl | 0.56 | 0 | — | 0 | 8 | — | — | — | — | 0 | 0 | 0 | 0 | 9 | 0 | 7 | — | 5 | — | 0 | 5 | — | — | 8 |
| $R_3$ = 4-Chlorophenyl | 0.28 | 0 | — | 0 | 8 | — | — | — | — | 0 | 0 | 0 | 0 | 9 | 0 | 0 | — | 5 | — | 0 | 6 | — | — | 9 |
| E + T (45/55) | 0.14 | 0 | — | 0 | 7 | — | — | — | — | 0 | 0 | 0 | 0 | 8 | 0 | 0 | — | 5 | — | 0 | 6 | — | — | 9 |
| $R_1$ = OH | 1.12 | 2 | — | 0 | 5 | — | — | — | — | 0 | 0 | 0 | 0 | 8 | 0 | 5 | — | 5 | — | 0 | 2 | — | — | 7 |
| $R_2$ = 4-Chlorophenyl | 0.56 | 0 | — | 0 | — | — | — | — | — | 0 | 0 | 0 | 0 | 0 | 8 | 0 | 3 | — | 6 | — | 0 | — | — | — |
| $R_3$ = 3-Chlorophenyl | 0.28 | 0 | — | 0 | — | — | — | — | — | 0 | 0 | 0 | 0 | 7 | 0 | 0 | — | 5 | — | 0 | 0 | — | — | 2 |
| E + T (79/21) | | | | | | | | | | | | | | | | | | | | | | | | |
| $R_1$ = OH | 1.12 | 6 | — | 5 | 9 | — | — | — | — | 5 | 8 | 2 | 5 | 9 | 0 | 9 | — | 7 | — | 9 | 9 | — | — | 9 |
| $R_2$ = 4-Chlorophenyl | 0.28 | 3 | — | 5 | 9 | — | — | — | — | 5 | 8 | 0 | 3 | 9 | 0 | 9 | — | 8 | — | 8 | 9 | — | — | 9 |
| $R_3$ = 3-Chlorophenyl | 0.07 | 0 | — | 3 | 9 | — | — | — | — | 0 | 5 | 0 | 2 | 9 | 0 | 5 | — | 7 | — | 5 | 8 | — | — | 9 |
| E + T (30/70) | 0.035 | 0 | — | 0 | 8 | — | — | — | — | 0 | 0 | 0 | 0 | 9 | 0 | 2 | — | 2 | — | 2 | 7 | — | — | 9 |
| *$R_1$ = OH | 1.12 | 2 | — | 5.5 | 8 | — | — | — | — | 5 | 8 | 9 | 4.5 | 6 | 0 | 8 | 5 | 8 | — | 9 | 8 | — | — | 5.5 |
| $R_2$ = Phenyl | 0.56 | 0 | — | 4 | 8.5 | — | — | — | — | 5 | 8 | 8.5 | 4.5 | 6 | 0 | 8 | 5 | 5 | — | 9 | 8 | — | — | 5.5 |
| $R_3$ = 3,5-Dichloro- | 0.14 | 0 | — | 1 | 4 | — | — | — | — | 1.5 | 7.5 | 5 | 0 | 4.5 | 0 | 8 | 5 | 7 | — | 6 | 6 | — | — | 4.5 |
| phenyl | 0.07 | 0 | — | 0 | 0 | — | — | — | — | 0 | 5 | 4 | 0 | 4 | 0 | 8 | 5 | 3 | — | 2 | 3.5 | — | — | 4 |

TABLE II-continued
Postemergence Herbicidal Activity of Polysubstituted Acids and Derivatives having the Formula:

$$N{\equiv}C-CH-CH-CH_2-CO-R_1$$
$$\phantom{N{\equiv}C-CH}|\phantom{CH}|$$
$$\phantom{N{\equiv}C-CH}R_3\phantom{H}R_2$$

| Structure | Rate kg/ha | N | SE | LA | MU | PI | RW | MG | VL | TB | BA | CR | FO | WO | BG | CH | CG | CN | SY | AN | NG | ER | BB | ST |
|---|---|---|---|---|---|---|---|---|---|---|---|---|---|---|---|---|---|---|---|---|---|---|---|---|
| E + T (58/42) | | | | | | | | | | | | | | | | | | | | | | | | |
| R$_1$ = OH | 1.12 | 2 | — | 8 | 9 | — | — | — | — | 7 | 8 | 7 | 7 | 9 | 8 | 9 | — | 7 | — | 3 | 6 | — | — | 9 |
| R$_2$ = Phenyl | 0.56 | 2 | — | 7 | 9 | — | — | — | — | 7 | 8 | 5 | 8 | 9 | 8 | 9 | — | 6 | — | 3 | 5 | — | — | 9 |
| R$_3$ = 4-Fluorophenyl | 0.14 | 0 | — | 2 | 2 | — | — | — | — | 2 | 3 | 0 | 2 | 9 | 7 | 9 | — | 3 | — | 0 | 2 | — | — | 9 |
| E + T (56/44) | 0.07 | 0 | — | 0 | 0 | — | — | — | — | 0 | 2 | 0 | 0 | 9 | 1 | 6 | — | 0 | — | 0 | 1 | — | — | 9 |
| R$_1$ = OCH$_2$CH$_2$OC$_4$H$_9$-n | 1.12 | 0 | — | 0 | 0 | — | — | — | — | 0 | 5 | 0 | 5 | 9 | 9 | 9 | — | 5 | — | 2 | 5 | — | — | 9 |
| R$_2$ = Phenyl | 0.56 | 0 | — | 0 | 0 | — | — | — | — | 0 | 0 | 0 | 2 | 8 | 3 | 3 | — | 0 | — | 0 | 5 | — | — | 9 |
| R$_3$ = Phenyl | 0.28 | 0 | — | 0 | 0 | — | — | — | — | 0 | 0 | 0 | 0 | 9 | 0 | 6 | — | 0 | — | 0 | 5 | — | — | 8 |
| E + T (40/60) | 0.14 | 0 | — | 0 | 0 | — | — | — | — | 0 | 0 | 0 | 0 | 7 | 0 | 5 | — | 0 | — | 0 | 3 | — | — | 0 |
| R$_1$ = OC$_2$H$_5$ | 1.12 | 3 | — | 7 | 9 | — | — | — | — | 9 | 5 | 0 | 3 | 9 | 8 | 9 | — | 8 | — | 9 | 9 | — | — | 9 |
| R$_2$ = 4-Chlorophenyl | 0.28 | 0 | — | 3 | 7 | — | — | — | — | 5 | 5 | 0 | 3 | 9 | 3 | 9 | — | 8 | — | 8 | 9 | — | — | 9 |
| R$_3$ = 3-Chlorophenyl T | 0.07 | 0 | — | 2 | 7 | — | — | — | — | 0 | 0 | 0 | 0 | 9 | 0 | 8 | — | 7 | — | 9 | 9 | — | — | 8 |
| (19/81) | 0.035 | 0 | — | 0 | 5 | — | — | — | — | 0 | 0 | 0 | 0 | 9 | 0 | 3 | — | 7 | — | 1 | 9 | — | — | 9 |
| R$_1$ = OH | 1.12 | 0 | — | 0 | 9 | — | — | — | — | 7 | 5 | 0 | 3 | 8 | 7 | 0 | — | 3 | — | 9 | 9 | — | — | 7 |
| R$_2$ = Phenyl | 0.56 | 0 | — | 0 | 9 | — | — | — | — | 7 | 0 | 0 | 0 | 9 | 8 | 0 | — | 2 | — | 2 | 3 | — | — | 3 |
| R$_3$ = 3,4-Dichlorophenyl | 0.14 | 0 | — | 0 | 5 | — | — | — | — | 5 | 0 | 0 | 0 | 7 | 7 | 0 | — | 0 | — | 0 | 0 | — | — | 0 |
| E + T (57/43) | 0.035 | 0 | — | 0 | 2 | — | — | — | — | 0 | 0 | 0 | 0 | 7 | 0 | 0 | — | 0 | — | 0 | 0 | — | — | 0 |
| R$_1$ = OC$_2$H$_5$ | 1.12 | 0 | — | 0 | 0 | — | — | — | — | 0 | 0 | 0 | 0 | 9 | 0 | 0 | — | 0 | — | 0 | 0 | — | — | 0 |
| R$_2$ = 2,4-Dichlorophenyl | 0.56 | 0 | — | 0 | 0 | — | — | — | — | 0 | 0 | 0 | 0 | 9 | 0 | 0 | — | 0 | — | 0 | 0 | — | — | 0 |
| R$_3$ = 3-Chlorophenyl E + T (50/50) | 0.28 | 0 | — | 0 | 0 | — | — | — | — | 0 | 0 | 0 | 0 | 7 | 0 | 0 | — | 0 | — | 0 | 0 | — | — | 0 |
| R$_1$ = OH | 1.12 | 8 | — | — | 3 | — | — | — | — | 8 | 5 | 0 | 7 | 9 | 7 | 8 | -2 | — | 2 | 15 | — | — | 4 | 5 |
| R$_2$ = 4-Fluorophenyl | 0.56 | 3 | — | — | 2 | — | — | — | — | 7 | 77.5 | 0 | 7 | 9 | 7 | 7 | — | 0 | — | 0 | 0 | — | — | |
| R$_3$ = Phenyl | 0.14 | 0 | — | — | 0 | — | — | — | — | 50 | 0 | 8 | 8 | 2 | 7 | 1 | 0 | 0 | 0 | 0 | 0 | 5 | 2 | 0 |
| E + T (76/24) | 0.035 | 0 | — | — | 0 | — | — | — | — | 1 | 0 | 0 | 6 | 6 | 0 | 0 | — | 0 | — | 0 | 0 | — | — | |
| R$_1$ = OC$_2$H$_5$ | 1.12 | 8 | — | 0 | 8 | — | — | — | — | 6 | 6 | 0 | 7 | 9 | 8 | 8 | — | 7 | — | 5 | 3 | — | — | 8 |
| R$_2$ = 4-Fluorophenyl | 0.56 | 7 | — | 0 | 5 | — | — | — | — | 6 | 5 | 0 | 7 | 9 | 7 | 8 | -47 7 | — | 6 | 2 | — | — | 9 | 43 |
| R$_3$ = Phenyl E + T (60/40) | 0.14 | 1 | — | — | 0 | — | — | — | — | 3 | 0 | 0 | 3 | 8 | 6 | 7 | — | 3 | 2 | 0/1 | 0 | — | — | 2 |
|  | 0.035 | 0 | — | — | 0 | — | — | — | — | 1 | 0 | 0 | 0 | 8 | 3 | 1 | — | 0 | — | 1 | 0 | 5 | — | |
| R$_1$ = OC$_2$H$_5$ | 1.12 | 0 | — | — | 7 | — | — | — | — | 7 | 8 | 7 | 7 | 9 | 8 | 9 | — | 7 | — | 9 | 9 | — | — | 9 |
| R$_2$ = 3-Cyanophenyl | 0.56 | 0 | — | — | 6 | — | — | — | — | 0 | 8 | 0 | 3 | 9 | 8 | 9 | — | 7 | — | 9 | 9 | — | — | 9 |
| R$_3$ = 3-Chlorophenyl | 0.14 | 0 | — | — | 5 | — | — | — | — | 0 | 2 | 0 | 0 | 9 | 0 | 8 | 6 | 7 | % | 6 | 7 | — | — | 9 |
| E + T (50/50) | 0.035 | 0 | — | — | 3 | — | — | — | 0 | 0 | 0 | 0 | 9 | 5 | | | | | | | | | | |

TABLE II-continued

Postemergence Herbicidal Activity of Polysubstituted Acids and Derivatives having the Formula:

$$N\equiv C-\underset{R_3}{\underset{|}{C}}H-\underset{R_2}{\underset{|}{C}}H-CH_2-CO-R_1$$

| Structure | Rate kg/ha | N | SE | LA | MU | PI | RW | MG | VL | TB | BA | CR | FO | WO | BG | CH | CG | CN | SY | AN | NG | ER | BB | ST |
|---|---|---|---|---|---|---|---|---|---|---|---|---|---|---|---|---|---|---|---|---|---|---|---|---|
| $R_1$ = OC$_2$H$_5$ | 1.12 | 2 | — | 2 | 3 | — | — | — | — | 3 | 0 | 0 | 9 | 8 | — | — | 0 | 9 | — | — | — | 9 | — | — |
| $R_2$ = 3-Cyanophenyl | 0.56 | 0 | — | 0 | 0 | — | — | — | — | 2 | 0 | 0 | 9 | 8 | — | 6 | 0 | — | 5 | 6 | — | — | 8 | 7 |
| $R_3$ = Phenyl | 0.14 | 0 | — | 0 | 0 | — | — | — | — | 0 | 0 | 0 | 0 | 9 | 8 | 6 | — | 0 | — | 5 | 7 | — | — | — |
| π (15/85) | 0.035 | | | | | | | | | | | | | 8 | 0 | 3 | — | 0 | — | 3 | 2 | 3 | — | — |
| $R_1$ = OH | 1.12 | 2 | — | 0 | 8 | — | — | — | — | 8 | 0 | 7 | 0 | 9 | 8 | 3 | — | 7 | — | 3 | — | 3 | — | — |
| $R_2$ = 3-Cyanophenyl | 0.56 | 0 | — | 0 | 8 | — | — | — | — | 0 | 0 | 0 | 0 | 8 | 0 | 2 | — | 0 | — | — | 1 | — | — | 2 |
| $R_3$ = Phenyl | 0.14 | 0 | — | 0 | 5 | — | — | — | — | 0 | 0 | 0 | 0 | 7 | 0 | 0 | — | 0 | — | 0 | 0 | — | — | 2 |
| E + T (75/25) | 0.035 | 0 | — | 0 | 0 | — | — | — | — | 0 | 0 | 0 | 0 | 2 | 0 | 0 | — | 0 | — | 0 | 0 | — | — | 0 |
| $R_1$ = OH | 1.12 | 0 | — | 0 | 0 | — | — | — | — | 0 | 0 | 0 | 0 | 8 | 0 | 2 | — | 0 | — | 0 | 0 | — | — | 0 |
| $R_2$ = 2,4-Dichloro- | 0.56 | 0 | — | 0 | 0 | — | — | — | — | 0 | 0 | 0 | 0 | 8 | 3 | 0 | — | 0 | — | 0 | 0 | — | — | 0 |
| phenyl | 0.14 | 0 | — | 0 | 0 | — | — | — | — | 0 | 0 | 0 | 0 | 2 | 0 | 0 | — | 0 | — | 0 | 0 | — | — | 0 |
| $R_3$ = Phenyl | 0.035 | | | | | | | | | | | | | | | | | | | | | | | |
| E + T (50/50) | | | | | | | | | | | | | | | | | | | | | | | | |
| $R_1$ = OC$_2$H$_5$ | 1.12 | 2 | — | 2 | 7 | — | — | — | — | 8 | 0 | 0 | 8 | 8 | 3 | 7 | — | 3 | — | 0 | 3 | — | — | 3 |
| $R_2$ = 3-Bromophenyl | 0.56 | 2 | — | 2 | 7 | — | — | — | — | 8 | 0 | 0 | 7 | 8 | 0 | 7 | — | 2 | — | 0 | 0 | — | — | 3 |
| $R_3$ = Phenyl | 0.14 | 0 | — | 0 | 3 | — | — | — | — | 8 | 0 | 0 | 7 | 8 | 0 | 7 | — | 0 | — | 0 | 0 | — | -2 | 0 |
| T | 0.035 | 0 | — | 2 | 0 | — | — | — | — | 7 | 0 | 0 | 5 | 7 | 0 | 6 | 12 | 0 | 0 | 0 | 0 | — | 0 | 0 |
| $R_1$ = OH | 1.12 | 0 | — | 0 | 9 | — | — | — | — | 8 | 0 | 0 | 0 | 7 | 0 | 6 | — | 2 | — | 0 | 0 | — | — | 0 |
| $R_2$ = 3-Bromophenyl | 0.56 | 0 | — | 0 | 5 | — | — | — | — | 8 | 0 | 0 | 8 | 7 | 0 | 0 | — | 0 | — | 0 | 0 | — | — | 0 |
| $R_3$ = Phenyl | 0.14 | 0 | — | 0 | 2 | — | — | — | — | 7 | 0 | 0 | 8 | 5 | 0 | 0 | — | 0 | — | 0 | 0 | — | — | 0 |
| E + T | 0.035 | 0 | — | 0 | 0 | — | — | — | — | 5 | 0 | 0 | 0 | 0 | 0 | 0 | — | 7 | — | 3 | 3 | — | — | 6 |
| $R_1$ = OC$_2$H$_5$ | 1.12 | 7 | — | 0 | 5 | — | — | — | — | 8 | 7 | 0 | 8 | 9 | 7 | 9 | — | 7 | — | 2 | 2 | — | — | 6 |
| $R_2$ = 3-Fluorophenyl | 0.56 | 7 | — | 0 | 3 | — | — | — | — | 8 | 7 | 0 | 8 | 9 | 7 | 9 | — | 3 | — | 0 | 0 | — | — | 0 |
| $R_3$ = Phenyl | 0.14 | 0 | — | 0 | 0 | — | — | — | — | 7 | 5 | 0 | 7 | 8 | 0 | 8 | — | 0 | — | 5 | 8 | — | — | 8 |
| E + T | 0.035 | 7 | — | 2 | 8 | — | — | — | — | 8 | 8 | 0 | 8 | 9 | 8 | 9 | — | 7 | — | 3 | 8 | — | — | 8 |
| $R_1$ = OH | 1.12 | 0 | — | 0 | 7 | — | — | — | — | 8 | 8 | 0 | 8 | 9 | 7 | 9 | — | 5 | — | 3 | 3 | — | — | 7 |
| $R_2$ = 3-Fluorophenyl | 0.56 | 0 | — | 0 | 3 | — | — | — | — | 8 | 6 | 0 | 7 | 9 | 5 | 9 | — | 5 | — | 0 | 0 | — | — | 7 |
| $R_3$ = Phenyl | 0.14 | 0 | — | 3 | 3 | — | — | — | — | 6 | 3 | 0 | 3 | 9 | 0 | 8 | — | 3 | — | 0 | 0 | — | — | 7 |
| E + T | 0.35 | 0 | — | 0 | 0 | — | — | — | — | 3 | 0 | 0 | 0 | 9 | 0 | 0 | — | 5 | — | 0 | 0 | — | — | 6 |
| $R_1$ = OH | 0.56 | 0 | — | 0 | 0 | — | — | — | — | 0 | 0 | 0 | 0 | 9 | 0 | 0 | — | 3 | — | 0 | 0 | — | — | 7 |
| $R_2$ = Phenyl | 0.28 | 0 | — | 0 | 0 | — | — | — | — | 0 | 0 | 0 | 0 | 7 | 0 | 0 | — | | — | 0 | 0 | — | — | |
| $R_3$ = 3,4-(Methylene- | 0.14 | 0 | — | 0 | 0 | — | — | — | — | | | | | | | | | | | | | | | |
| dioxyphenyl | 0.07 | 0 | — | 0 | 0 | — | — | — | — | | | | | | | | | | | | | | | |
| E + T (59/41) | | | | | | | | | | | | | | | | | | | | | | | | |
| $R_1$ = OC$_2$H$_5$ | 1.12 | 0 | — | 0 | 8 | — | — | — | 0 | 0 | 0 | — | 3 | 9 | 0 | 9 | — | 3 | — | 0 | 0 | — | — | 0 |
| $R_2$ = 3-Chloro- | 0 | 7 | 9 | 0 | 9 | — | 6 | — | 0 | 7 | 0 | 0 | 7 | 9 | 0 | 9 | — | 2 | — | 0 | 0 | — | — | 0 |
| 4-fluorophenyl | 0.56 | 0 | — | 0 | 7 | — | — | — | — | 7 | 0 | 0 | 7 | 8 | 0 | 8 | — | 2 | — | 0 | 0 | — | — | 0 |
| $R_3$ = Phenyl | 0.28 | 0 | — | 0 | 3 | — | — | — | — | 3 | 0 | 0 | 5 | 9 | 0 | 8 | — | 0 | — | 0 | 0 | — | — | 0 |
| E + T | 0.14 | 0 | — | 0 | 0 | — | — | — | — | 0 | 0 | 0 | 3 | | | | | | | | | | | |
| | 0.07 | | | | | | | | | | | | | | | | | | | | | | | |

TABLE II-continued

Postemergence Herbicidal Activity of Polysubstituted Acids and Derivatives having the Formula:

$$N\equiv C-\underset{R_3}{\overset{}{C}}H-\underset{R_2}{\overset{}{C}}H-CH_2-CO-R_1$$

| Structure | Rate kg/ha | N | SE | LA | MU | PI | RW | MG | VL | TB | BA | CR | FO | WO | BG | CH | CG | CN | SY | AN | NG | ER | BB | ST |
|---|---|---|---|---|---|---|---|---|---|---|---|---|---|---|---|---|---|---|---|---|---|---|---|---|
| (63/37) | 0.035 | 9 | 9 | 9 | — | — | — | — | 9 | 9 | 9 | 9 | 9 | 9 | — | 0 | 9 | 9 | 0 | 9 | 1 = OH . (n-C₃H₇)₂NH | 2.0 | — | — |
| R₂ = Phenyl | 1.0 | — | — | — | — | — | — | — | — | — | — | — | 0 | 9 | — | — | 9 | — | — | 7 | 0 | 5 | 0 | 7 |
| R₃ = Phenyl | 0.5 | — | — | — | — | — | — | — | — | — | — | — | 3 | 9 | — | — | 9 | — | — | 7 | 0 | 5 | 0 | 7 |
| E + T | 0.25 | — | — | — | — | — | — | — | — | — | — | — | 0 | 9 | 9 | — | 9 | — | — | 5 | 0 | 8 | 0 | 7 |
|  | 0.13 | — | — | — | — | — | — | — | — | — | — | — | 0 | 9 | 0 | — | 9 | — | — | 3 | 0 | 5 | 0 | 5 |
| R₁ = OH . diiso- | 2.0 | — | — | — | — | — | — | — | — | — | — | — | 8 | 9 | 9 | — | 9 | — | — | 7 | 0 | 3 | 0 | 5 |
| propylamino | 1.0 | — | — | — | — | — | — | — | — | — | — | — | 5 | 9 | — | — | 7 | — | — | 2 | 0 | 3 | 0 | 5 |
| R₂ = Phenyl | 0.5 | — | — | — | — | — | — | — | — | — | — | — | 2 | 9 | — | — | 9 | — | — | 2 | 0 | 0 | 0 | 0 |
| R₃ = Phenyl | 0.25 | — | — | — | — | — | — | — | — | — | — | — | 0 | 9 | — | — | — | — | — | 0 | 0 | 0 | 0 | 0 |
| E + T | 0.13 | — | — | — | — | — | — | — | — | — | — | — | 0 | 9 | — | — | — | — | — | 0 | 0 | 0 | 0 | 0 |
| R₁ = OH . n-C₈H₁₇—NH₂ | 2.0 | — | — | — | — | — | — | — | — | — | — | — | 8 | 9 | — | — | — | — | — | 3 | 0 | 2 | 2 | 7 |
|  | 1.0 | — | — | — | — | — | — | — | — | — | — | — |  | 3 | 3 | 3 | 2 | 3 | — | — | 2 | 0 | 0 | 073 |
| R₂ = Phenyl | 0.5 | — | — | — | — | — | — | — | — | — | — | — | 0 | 9 | 0 | — | 2 | — | — | 2 | 2 | 2 | 0 | 3 |
| R₃ = Phenyl | 0.25 | — | — | — | — | — | — | — | — | — | — | — | 0 | 9 | 0 | — | 0 | — | — | 0 | 0 | 5 | 0 | 3 |
| E + T | 0.13 | — | — | — | — | — | — | — | — | — | — | — | 0 | 9 | 0 | — | 0 | — | — | 0 | 3 | 0 | 0 | 0 |
| R₁ = OH . C₂H₅NH₂ | 2.0 | — | — | — | — | — | — | — | — | — | — | — | 9 | 9 | 8 | — | 9 | — | — | 3 | 3 | 3 | 0 | 8 |
| R₂ = Phenyl | 1.0 | — | — | — | — | — | — | — | — | — | — | — | 8 | 9 | 0 | — | 6 | — | — | 3 | 3 | 3 | 0 | 8 |
| R₃ = Phenyl | 0.5 | — | — | — | — | — | — | — | — | — | — | — | 0 | 9 | 0 | — | 6 | — | — | 3 | 3 | 3 | 0 | 8 |
| E + T | 0.25 | — | — | — | — | — | — | — | — | — | — | — | 6 | 9 | 0 | — | 5 | — | — | 0 | 3 | 3 | 0 | 3 |
|  | 0.13 | — | — | — | — | — | — | — | — | — | — | — | 4 | 5 | 0 | — | — | 5 | — | 2 | 0 | 2 | 0 | 3 |
| R₁ = OC₂H₅ | 1.12 | 0 | — | 0 | 2 | — | — | — | — | 2 | 7 | 6 | 6 | 9 | 0 | 9 | — | 7 | — | — | 3 | 1 | 0 | 8 |
| R₂ = m-Nitrophenyl | 0.56 | 0 | — | 6 | 0 | — | — | — | — | 0 | 0 | 2 | 5 | 9 | 0 | 7 | — | 7 | — | 2 | 2 | 0 | 0 | 8 |
| R₃ = 3,5-Dichloro- | 0.28 | 0 | — | 6 | 0 | — | — | — | — | 0 | 0 | 0 | 2 | 9 | 0 | 2 | — | 7 | — | 2 | 0 | 0 | 0 | 5 |
| phenyl | 0.14 | 0 | — | 0 | 0 | — | — | — | — | 0 | 0 | 0 | 0 | 8 | 0 | 0 | — | 5 | — | 0 | 0 | 0 | 0 | 2 |
| E + T | 0.07 | 0 | — | 0 | 0 | — | — | — | — | 0 | 0 | 0 | 0 | 5 | 0 | 0 | — | — | — | 0 | 0 | 0 | 0 | 0 |
| (77/23) |  |  |  |  |  |  |  |  |  |  |  |  |  |  |  |  |  |  |  |  |  |  |  |  |
| R₁ = OC₂H₅ | 1.12 | 0 | — | 0 | 5 | — | — | — | — | 2 | 8 | 7 | 6 | 9 | 0 | 8 | — | 7 | — | 5 | 2 | 0 | — | 8 |
| R₂ = m-Nitrophenyl | 0.56 | 0 | — | 0 | 2 | — | — | — | — | 0 | 7 | 7 | 6 | 9 | 0 | 8 | — | 7 | — | 2 | 0 | 0 | — | 5 |
| R₃ = 3,5-Dichloro- | 0.28 | 0 | — | 0 | 0 | — | — | — | — | 0 | 3 | 3 | 6 | 9 | 0 | 8 | — | 7 | — | 0 | 0 | 0 | — | 2 |
| phenyl | 0.14 | 0 | — | 0 | 0 | — | — | — | — | 0 | 0 | 2 | 3 | 9 | 0 | 8 | — | 6 | — | 0 | 0 | 0 | — | 2 |
| E + T | 0.07 | 0 | — | 0 | 0 | — | — | — | — | 0 | 0 | 0 | 3 | 9 | 0 | 2 | — | — | — | 0 | 0 | 0 | — | 2 |
| (5/95) |  |  |  |  |  |  |  |  |  |  |  |  |  |  |  |  |  |  |  |  |  |  |  |  |
| R₁ = OH . 1,1,3,3- | 1.0 | 3 | — | 6 | 0 | — | — | — | — | 8 | 0 | 0 | 3 | 9 | 0 | 9 | — | 0 | — | 0 | 7 | 0 | — | 8 |
| Tetramethyl- | 0.5 | 0 | — | 0 | 0 | — | — | — | — | 7 | 0 | 0 | 0 | 9 | 0 | 8 | — | 0 | 0 | 0 | 0 | 0 | 5 | 8 |
| butylamine | 0.25 | 0 | — | 0 | 0 | — | — | — | — | 5 | 0 | 0 | 0 | 9 | 0 | 0 | — | 0 | — | 0 | 0 | 0 | — | 0 |
| R₂ = Phenyl | 0.13 | 0 | — | 0 | 0 | — | — | — | — | 0 | 0 | 0 | 0 | 8 | 0 | 0 | — | 0 | — | 0 | 0 | 0 | — | 0 |
| R₃ = Phenyl | 0.06 | 0 | — | 0 | 0 | — | — | — | — | 0 | 0 | 0 | 0 | 8 | — | 0 | — | — | — | 0 | 0 | 0 | — | 0 |
| E + T |  |  |  |  |  |  |  |  |  |  |  |  |  |  |  |  |  |  |  |  |  |  |  |  |
| (50/50) |  |  |  |  |  |  |  |  |  |  |  |  |  |  |  |  |  |  |  |  |  |  |  |  |
| R₁ = OC₂H₅ | 1.0 | 3 | — | 0 | 8 | — | — | — | — | — | 5 | 3 | 8 | 9 | 9 | 8 | — | 7 | — | 9 | — | — | — | 9 |
| R₂ = 3,4-Difluoro- | 0.5 | 3 | — | 0 | 5 | — | — | — | — | — | 0 | 3 | 7 | 9 | 8 | 9 | — | 2 | — | 7 | — | — | — | 8 |

TABLE II-continued
Postemergence Herbicidal Activity of Polysubstituted Acids and Derivatives having the Formula:

$$N\equiv C-\underset{R_2}{\underset{|}{CH}}-\overset{R_3}{\overset{|}{CH}}-CH_2-CO-R_1$$

| Structure | Rate kg/ha | N | SE | LA | MU | PI | RW | MG | VL | TB | BA | CR | FO | WO | BG | CH | CG | CN | SY | AN | NG | ER | BB | ST |
|---|---|---|---|---|---|---|---|---|---|---|---|---|---|---|---|---|---|---|---|---|---|---|---|---|
| phenyl | 0.25 | 0 | — | 0 | 2 | — | — | — | — | — | 0 | 0 | 5 | 9 | 8 | 9 | — | 0 | — | 6 | — | — | — | 9 |
| R$_3$ = Phenyl | 0.13 | 0 | — | 0 | 0 | — | — | — | — | — | 0 | 0 | 3 | 9 | 0 | 5 | — | 0 | — | 5 | — | — | — | 9 |
| E + T (50/50) | 0.06 | 0 | — | 0 | 0 | — | — | — | — | — | 0 | 0 | 0 | 9 | 0 | 3 | — | 0 | — | 3 | — | — | — | 9 |

E = Erythro
T = Threo
*Two or more tests:

EXAMPLE 17

Preemergence and Postemergence Herbicidal Activity of Optical Isomers of Polysubstituted Butanoic Acids Having the Formula:

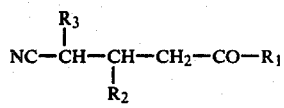

Employing the preemergence herbicidal evaluation procedure of Example 15 and the postemergence herbicidal evaluation procedure of Example 16, the (+)-threo and (−)-threo optical isomers of the above-noted compounds were evaluated. Data obtained are provided in Tables III and III-A, where it can be seen that the (−)-threo isomer is substantially more effective as both a preemergence and postemergence herbicide than the (+)-threo isomers.

These data suggest that the high degree of herbicidal activity of the polysubstituted butanoic acids, esters and derivatives of the present invention is due to only one threo stereoisomer.

TABLE III

Preemergence Herbicidal Activity of Polysubstituted Acids and Derivatives having the Formula

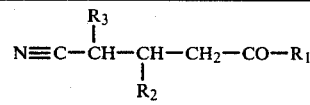

| Structure | Rate kg/ha | PN | SE | LA | MU | PI | RW | MG | VL | TB | BA | CR | FO |
|---|---|---|---|---|---|---|---|---|---|---|---|---|---|
| $R_1$ = OH | 1.12 | — | — | — | 8 | — | — | 8 | 8 | 8 | 9 | — | 7 |
| $R_2$ = Phenyl | 0.56 | — | — | — | 8 | — | — | 7 | 7 | 7 | 9 | — | 6 |
| $R_3$ = Phenyl | 0.28 | — | — | — | 2 | — | — | 0 | 6 | 3 | 9 | — | 6 |
| (−)-T | 0.14 | — | — | — | 2 | — | — | 0 | 6 | 0 | 7 | — | 6 |
|  | 0.07 | — | — | — | 0 | — | — | 0 | 6 | 0 | 0 | — | 3 |
|  | 0.03 | — | — | — | 0 | — | — | 0 | 0 | 0 | 0 | — | 0 |
| $R_1$ = OH | 1.12 | — | — | — | 5 | — | — | 0 | 8 | 0 | 7 | — | 6 |
| $R_2$ = Phenyl | 0.56 | — | — | — | 0 | — | — | 0 | 0 | 0 | 3 | — | 0 |
| $R_3$ = Phenyl | 0.28 | — | — | — | 0 | — | — | 0 | 0 | 0 | 0 | — | 0 |
| (+)-T | 0.14 | — | — | — | 0 | — | — | 0 | 0 | 0 | 0 | — | 0 |

| Structure | Rate kg/ha | WO | BG | CH | CG | CN | SY | AN | NG | ER | EB | ST |
|---|---|---|---|---|---|---|---|---|---|---|---|---|
| $R_1$ = OH | 1.12 | 9 | — | — | — | 7 | 8 | 7 | 8 | — | — | 9 |
| $R_2$ = Phenyl | 0.56 | 9 | — | — | — | 3 | 7 | 2 | 7 | — | — | 8 |
| $R_3$ 32 Phenyl | 0.28 | 9 | — | — | — | 0 | 5 | 0 | 5 | — | — | 8 |
| (−)-T | 0.14 | 9 | — | — | — | 0 | 3 | 0 | 2 | — | — | 7 |
|  | 0.07 | 8 | — | — | — | 0 | 2 | 0 | 0 | — | — | 3 |
|  | 0.03 | 7 | — | — | — | 0 | 0 | 0 | 0 | — | — | 0 |
| $R_1$ = OH | 1.12 | 9 | — | — | — | 0 | 2 | 3 | 0 | — | — | 3 |
| $R_2$ = Phenyl | 0.56 | 2 | — | — | — | 0 | 0 | 0 | 0 | — | — | 0 |
| $R_3$ = Phenyl | 0.28 | 1.5 | — | — | — | 0 | 0 | 0 | 0 | — | — | 0 |
| (+)-T | 0.14 | 0 | — | — | — | 0 | 0 | 0 | 0 | — | — | 0 |

E = Erythro
T = Threo
*Average of two or more tests.

TABLE III-A

Postemergence Herbicidal Activity of Polysubstituted Acids and Derivatives having the Formula:

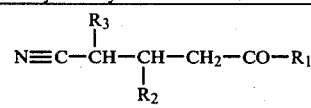

| Structure | Rate kg/ha | PN | SE | LA | MU | PI | RW | MG | VL | TB | BA | CR | FO |
|---|---|---|---|---|---|---|---|---|---|---|---|---|---|
| $R_1$ = OH | 1.12 | — | — | 9 | 9 | — | — | — | — | 9 | 8 | 0 | 8 |
| $R_2$ = Phenyl | 0.56 | — | — | 9 | 9 | — | — | — | — | 9 | 8 | 0 | 8 |
| $R_3$ = Phenyl | 0.28 | — | — | 8 | 9 | — | — | — | — | 9 | 7 | 0 | 7 |
| (−)-T | 0.14 | — | — | 6 | 7 | — | — | — | — | 9 | 6 | 0 | 7 |
|  | 0.07 | — | — | 2 | 5 | — | — | — | — | 8 | 6 | 0 | 6 |
|  | 0.035 | — | — | 0 | 0 | — | — | — | — | 7 | 2 | 0 | 6 |
|  | 0.018 | — | — | 0 | 0 | — | — | — | — | 5 | 0 | 0 | 5 |
| $R_1$ = OH | 1.12 | — | — | 2 | 3 | — | — | — | — | 7 | 0 | 0 | 5 |
| $R_2$ = Phenyl | 0.56 | — | — | 0 | 2 | — | — | — | — | 7 | 0 | 0 | 5 |
| $R_3$ = Phenyl | 0.28 | — | — | 0 | 0 | — | — | — | — | 5 | 0 | 0 | 3 |
| (+)-T | 0.14 | — | — | 0 | 0 | — | — | — | — | 2 | 0 | 0 | 3 |
|  | 0.07 | — | — | 0 | 0 | — | — | — | — | 1 | 0 | 0 | 2 |
|  | 0.035 | — | — | 0 | 0 | — | — | — | — | 1 | 0 | 0 | 0 |

| Structure | Rate kg/ha | WO | BG | CH | CG | CN | SY | AN | NG | ER | BB | ST |
|---|---|---|---|---|---|---|---|---|---|---|---|---|
| $R_1$ = OH | 1.12 | 9 | 9 | — | — | 6 | — | 8 | 8 | — | — | 9 |

TABLE III-A-continued

Postemergence Herbicidal Activity of Polysubstituted Acids and Derivatives having the Formula:

$$N\equiv C-\underset{\underset{R_2}{|}}{\overset{\overset{R_3}{|}}{CH}}-CH-CH_2-CO-R_1$$

| | | | | | | | | | | | |
|---|---|---|---|---|---|---|---|---|---|---|---|
| $R_2$ = Phenyl | 0.56 | 9 | 8 | — | — | 7 | — | 9 | 9 | — | — | 9 |
| $R_3$ = Phenyl | 0.28 | 9 | 8 | — | — | 6 | — | 7 | 8 | — | — | 9 |
| (−)-T | 0.14 | 9 | 8 | — | — | 3 | — | 6 | 8 | — | — | 9 |
| | 0.07 | 8 | 7 | — | — | 0 | — | 3 | 2 | — | — | 9 |
| | 0.035 | 8 | 6 | — | — | 0 | — | 2 | 2 | — | — | 8 |
| | 0.018 | 8 | 3 | — | — | 0 | — | 2 | 0 | — | — | 9 |
| $R_1$ = OH | 1.12 | 8 | 8 | — | — | 0 | — | 0 | 0 | — | — | 6 |
| $R_2$ = Phenyl | 0.56 | 8 | 7 | — | — | 0 | — | 0 | 0 | — | — | 2 |
| $R_3$ Phenyl | 0.28 | 8 | 5 | — | — | 0 | — | 0 | 0 | — | — | 0 |
| (+)-T | 0.14 | 8 | 0 | — | — | 0 | — | 0 | 0 | — | — | 2 |
| | 0.07 | 6 | 0 | — | — | 0 | — | 0 | 0 | — | — | 2 |
| | 0.035 | 1.5 | 0 | — | — | 0 | — | 0 | 0 | — | — | 0 |

E = Erythro
T = Threo

EXAMPLE 18

Evaluation of erythro, erythro and threo, and threo Stereoisomers as Postemergence Herbicidal Agent Dramatic herbicidal differences between erythro, erythro-threo and threo stereoisomers having identical $R_1$, $R_2$ and $R_3$ substituents, are noted in the following tests wherein compounds are evaluated as postemergence herbicides employing the procedure of Example 16. Data obtained are provided in Table IV below.

TABLE IV

Postemergence Herbicidal Activity of Polysubstituted Acids and Derivatives having the Formula:

$$N\equiv C-\underset{\underset{R_2}{|}}{\overset{\overset{R_3}{|}}{CH}}-CH-CH_2-CO-R_1$$

| Structure | Rate kg/ha | PN | SE | LA | MU | PI | RW | MG | VL | TB | BA | CR | FO |
|---|---|---|---|---|---|---|---|---|---|---|---|---|---|
| $R_1$ = OH | 1.12 | 0 | 0 | — | 0 | 0 | 0 | 0 | 2 | — | 0 | 0 | 2 |
| $R_2$ = Phenyl | 0.56 | 0 | 0 | — | 0 | 0 | 0 | 0 | 0 | — | 0 | 0 | 0 |
| $R_3$ = Phenyl | 0.28 | 0 | 0 | — | 0 | 0 | 0 | 0 | 0 | — | 0 | 0 | 0 |
| E | 0.14 | — | — | — | — | — | — | — | — | — | — | — | — |
| (95/5) | | | | | | | | | | | | | |
| *$R_1$ = OH | 1.12 | 1 | 6 | 2.8 | 5.6 | — | — | — | — | 6.3 | 2.8 | 0 | 4.8 |
| $R_2$ = Phenyl | 0.56 | 0 | 2 | 1.3 | 1.5 | — | — | — | — | 5.7 | 1.1 | 0 | 3.0 |
| $R_3$ = Phenyl | 0.28 | 0 | — | 0.5 | 0 | — | — | — | — | 3.8 | 0.1 | 0 | 2.1 |
| E + T | 0.14 | 0 | — | 0 | 0 | — | — | — | — | 0 | 0 | 0 | 0 |
| (67/33) | | | | | | | | | | | | | |
| *$R_1$ = OH | 1.12 | 5 | 7 | 7 | 7 | 5 | 6 | 6 | 6 | 8.5 | 6.6 | 0 | 8 |
| $R_2$ = Phenyl | 0.56 | 3 | 5 | 6 | 6 | 5 | 4 | 6 | 5 | 8.5 | 6.6 | 0 | 8 |
| $R_3$ = Phenyl | 0.28 | 2 | 3 | 5 | 5 | 5 | 0 | 1 | 3 | 8 | 5.3 | 0 | 7.5 |
| T | 0.14 | — | — | 5 | 3 | — | — | — | — | 8 | 5.5 | 0 | 7 |
| (5/95) | | | | | | | | | | | | | |
| *$R_1$ = CH | 1.12 | 1 | — | 2.6 | 7.6 | — | — | — | — | 6.6 | 1 | 2.6 | 3.3 |
| $R_2$ = 4-Chlorophenyl | 0.56 | 0 | — | 3 | 6.9 | — | — | — | — | 6.6 | 1 | 0 | 0.8 |
| $R_3$ = Phenyl | 0.07 | 0 | — | 0.8 | 0 | — | — | — | — | 2.3 | 1 | 0 | 0 |
| E + T | 0.035 | 0 | — | 0 | 0 | — | — | — | — | 0 | 1 | 0 | 0 |
| *$R_1$ = OH | 1.12 | 6 | — | 8 | 9 | — | — | — | — | 8.6 | 7.6 | 1.6 | 7.3 |
| $R_2$ = 4-Chlorophenyl | 0.56 | 0.5 | — | 7.5 | 8.5 | — | — | — | — | 8 | 5.6 | 0.8 | 4.3 |
| $R_3$ = Phenyl | 0.07 | 0 | — | 3 | 7 | — | — | — | — | 7 | 4.5 | 0 | 1 |
| T | 0.035 | 0 | — | 3 | 7 | — | — | — | — | 8 | 2 | 0 | 0.5 |
| *$R_1$ = OC$_2$H$_5$ | 1.12 | 0 | — | 0 | 5.5 | 5 | 0 | 0 | 2 | 4 | 2.6 | 0 | 3.3 |
| $R_2$ = 4-Chlorophenyl | 0.56 | 0 | — | 0 | 0 | 0 | 0 | 0 | 0 | 3.7 | 1 | 0 | 2.6 |
| $R_3$ = Phenyl | 0.28 | 0 | — | 0 | 0 | 0 | 0 | 0 | 0 | 0.8 | 0 | 0 | 0 |
| E | 0.14 | 0 | — | 0 | 0 | 0 | 0 | 0 | 0 | 0.8 | 0 | 0 | 0 |
| $R_1$ = OC$_2$H$_5$ | 1.12 | 0 | — | 0.3 | 7.6 | — | — | — | — | 8.6 | 2.3 | 0 | 2.6 |
| $R_2$ = 4-Chlorophenyl | 0.56 | 0 | — | 0.3 | 8 | — | — | — | — | 7.6 | 2 | 0 | 1 |
| $R_3$ = Phenyl | 0.28 | 0 | — | 0 | 4.3 | — | — | — | — | 6.6 | 1 | 0 | 0 |
| E + T | 0.14 | 0 | — | 0 | 2 | — | — | — | — | 4 | 0 | 0 | 0 |
| $R_1$ = OC$_2$H$_5$ | 1.12 | 2 | — | 0 | 8 | — | — | — | — | 0 | 3 | 0 | 2 |
| $R_2$ = 4-Chlorophenyl | 0.56 | 2 | — | 0 | 8 | — | — | — | — | 0 | 3 | 0 | 2 |
| $R_3$ = 3-Chlorophenyl | 0.28 | 1 | — | 0 | 6 | — | — | — | — | 0 | 3 | 0 | 0 |
| E + T | 0.14 | 0 | — | 0 | 5 | — | — | — | — | 0 | 0 | 0 | 0 |
| $R_1$ = OC$_2$H$_5$ | 1.12 | 3 | — | 7 | 9 | — | — | — | — | 9 | 5 | 0 | 3 |
| $R_2$ = 4-Chlorophenyl | 0.56 | 0 | — | 3 | 8 | — | — | — | — | 3 | 5 | 0 | 3 |
| $R_3$ = 3-Chlorophenyl | 0.28 | 0 | — | 3 | 7 | — | — | — | — | 5 | 5 | 0 | 3 |
| T | 0.14 | 0 | — | 2 | 7 | — | — | — | — | 0 | 3 | 0 | 0 |
| $R_1$ = OC$_2$H$_5$ | 1.12 | 0 | — | 0 | 7 | — | 0 | — | — | 9 | 8 | 3 | 7 |
| $R_2$ = Phenyl | 0.56 | 0 | — | 0 | 3 | — | 0 | — | — | 3 | 8 | 3 | 3 |
| $R_3$ = 3-Chlorophenyl | 0.28 | 0 | — | 0 | 2 | — | 0 | — | — | 3 | 7 | 0 | 2 |

TABLE IV-continued

Postemergence Herbicidal Activity of Polysubstituted Acids and Derivatives having the Formula:

$$N{\equiv}C-\underset{R_2}{\underset{|}{CH}}-\underset{}{\overset{R_3}{\underset{|}{CH}}}-CH_2-CO-R_1$$

| | Rate kg/ha | | | | | | | | | | |
|---|---|---|---|---|---|---|---|---|---|---|---|
| E + T | 0.14 | 0 | — | 0 | 0 | — | 0 | — | — | 3 | 3 | 0 | 0 |
| | 0.7 | — | — | 0 | 0 | — | 0 | — | — | 2 | 0 | 0 | 0 |
| $R_1$ = $OC_2H_5$ | 1.12 | 3 | — | 7 | 9 | — | 0 | — | — | 8 | 9 | 9 | 8 |
| $R_2$ = Phenyl | 0.56 | 0 | — | 6 | 9 | — | 0 | — | — | 9 | 9 | 9 | 8 |
| $R_3$ = 3-Chlorophenyl | 0.28 | 0 | — | 6 | 9 | — | 0 | — | — | 9 | 9 | 8 | 8 |
| T | 0.14 | — | — | 5 | 7 | — | 0 | — | — | 8 | 9 | 7 | 8 |
| | 0.07 | — | — | 0 | 3 | — | 0 | — | — | 8 | 9 | 5 | 8 |

| Structure | Rate kg/ha | WO | BG | CH | CG | CN | SY | AN | NG | ER | BB | ST |
|---|---|---|---|---|---|---|---|---|---|---|---|---|
| $R_1$ = OH | 1.12 | 2 | — | — | — | 0 | 1 | — | — | 0 | 0 | 0 |
| $R_2$ = Phenyl | 0.56 | 0 | — | — | — | 0 | 0 | — | — | 0 | 0 | 0 |
| $R_3$ = Phenyl | 0.28 | 0 | — | — | — | 0 | 0 | — | — | 0 | 0 | 0 |
| E | 0.14 | — | — | — | — | — | — | — | — | 0 | 0 | 0 |
| (95/5) | | | | | | | | | | | | |
| *$R_1$ = OH | 1.12 | 8.3 | 4.9 | 8.4 | 7.4 | 1.2 | — | 2.1 | 1.6 | 2.8 | 0.7 | 5.6 |
| $R_2$ = Phenyl | 0.56 | 7.8 | 4.8 | 6.8 | 7.0 | 0 | — | 0.9 | 0.9 | 2.0 | 0.4 | 5.6 |
| $R_3$ = Phenyl | 0.28 | 8.0 | 2.0 | 5.7 | 6.6 | 0 | — | 0.4 | 0.5 | 1.2 | 0 | 5.3 |
| E + T | 0.14 | 8.0 | 0 | 0 | — | 0 | — | 0 | 0 | 0 | 0 | 0 |
| (67/33) | | | | | | | | | | | | |
| *$R_1$ = OH | 1.12 | 9 | 8.5 | 8 | 7 | 5 | 6 | 7 | 8.5 | 1.6 | 2.2 | 9 |
| $R_2$ = Phenyl | 0.56 | 9 | 8.5 | 8 | 7 | 5 | 6 | 6 | 8 | 2.2 | 3 | 9 |
| $R_3$ = Phenyl | 0.28 | 9 | 5.5 | 8 | 7 | 3.5 | 3 | 5 | 7 | 3.3 | 3 | 9 |
| T | 0.14 | 9 | 4.5 | 8 | 7 | 1 | — | 3 | 5.5 | 2.2 | 2.2 | 9 |
| (5/95) | | | | | | | | | | | | |
| *$R_1$ = OH | 1.12 | 8.6 | 8.6 | 8 | 7 | 6.5 | — | 5.5 | 4.3 | — | — | 7.3 |
| $R_2$ = 4-Chlorophenyl | 0.56 | 8.6 | 8.6 | 7 | 7 | 2.5 | — | 4.5 | 3 | — | — | 7.3 |
| $R_3$ = Phenyl | 0.07 | 6.6 | 1.5 0.8 | 5 | 0.5 | — | 1 | 0.8 | — | — | 2 | |
| E + T | 0.035 | 5 | 0 | 0 | 3 | 0 | — | 0 | 0 | — | — | 0.3 |
| *$R_1$ = OH | 1.12 | 9 | 8.6 | 9 | 7 | 7.5 | — | 9 | 8.6 | — | — | 9 |
| $R_2$ = 4-Chlorophenyl | 0.56 | 9 | 8.6 | 8.6 | 7 | 7 | — | 9 | 7.7 | — | — | 8.6 |
| $R_3$ = Phenyl | 0.07 | 9 | 8.6 | 5.5 | 7 | 1 | — | 1.5 | 3.5 | — | — | 8.5 |
| T | 0.035 | 8.6 | 7.6 | 5 | 6 | 1.3 | — | — | — | — | — | 7 |
| *$R_1$ = $OC_2H_5$ | 1.12 | 6.4 | 3 | 7.6 | 9 | 2.3 | 0 | 3.4 | 0 | — | — | 3 |
| $R_2$ = 4-Chlorophenyl | 0.56 | 5.5 | 2.6 | 3.3 | 7 | 1.6 | 0 | 2.3 | 0 | — | — | 2.4 |
| $R_3$ = Phenyl | 0.28 | 5.5 | 0 | 0.8 | 7 | 0.8 | 0 | 1.7 | 0 | — | — | 2 |
| E | 0.14 | 4.7 | 0 | 0 | 7 | 0 | 0 | 1 | 0 | — | — | 1 |
| $R_1$ = $OC_2H_5$ | 1.12 | 9 | 8.6 | 7.6 | 9 | 6.5 | — | 8.5 | 8 | — | — | 8.6 |
| $R_2$ = 4-Chlorophenyl | 0.56 | 9 | 8.6 | 8.6 | 7 | 6.5 | — | 5.5 | 6 | — | — | 8.3 |
| $R_3$ = Phenyl | 0.28 | 9 | 8.3 | 8.6 | 7 | 5.5 | — | 5 | 5 | — | — | 7.3 |
| E + T | 0.14 | 8.3 | 6.6 | 7.6 | 6 | 3 | — | 1.5 | 3.3 | — | — | 7 |
| $R_1$ = $OC_2H_5$ | 1.12 | 9 | 8 | 8 | — | 7 | — | 7 | 9 | — | — | 7 |
| $R_2$ = 4-Chlorophenyl | 0.56 | 9 | 8 | 8 | — | 6 | — | 7 | 9 | — | — | 8 |
| $R_3$ = 3-Chlorophenyl | 0.28 | 9 | 3 | 7 | — | 6 | — | 2 | 8 | — | — | 6 |
| E + T | 0.14 | 8 | 3 | 2 | — | 6 | — | 1 | 7 | — | — | 5 |
| $R_1$ = $OC_2H_5$ | 1.12 | 9 | 8 | 9 | — | 8 | — | 9 | 9 | — | — | 9 |
| $R_2$ = 4-Chlorophenyl | 0.56 | 9 | 5 | 9 | — | 8 | — | 8 | 9 | — | — | 9 |
| $R_3$ = 3-Chlorophenyl | 0.28 | 9 | 3 | 9 | — | 8 | — | 8 | 9 | — | — | 9 |
| T | 0.14 | 9 | 3 | 9 | — | 8 | — | 9 | 9 | — | — | 8 |
| $R_1$ = $OC_2H_5$ | 1.12 | 9 | 9 | 7 | 8 | — | — | — | 3 | — | — | 7 |
| $R_2$ = Phenyl | 0.56 | 9 | 8 | 7 | 8 | — | — | — | 0 | — | — | 7 |
| $R_3$ = 3-Chlorophenyl | 0.28 | 9 | 9 | 3 | 8 | — | — | — | 0 | — | — | 7 |
| E + T | 0.14 | 9 | 2 | 3 | 7 | — | — | — | 0 | — | — | 5 |
| | 0.07 | 9 | 0 | 3 | 7 | — | — | — | 0 | — | — | 5 |
| $R_1$ = $OC_2H_5$ | 1.12 | 9 | 9 | 9 | 9 | — | — | — | 9 | — | — | 9 |
| $R_2$ = Phenyl | 0.56 | 9 | 8 | 9 | 7 | — | — | — | 9 | — | — | 9 |
| $R_3$ = 3-Chlorophenyl | 0.28 | 9 | 8 | 9 | 7 | — | — | — | 9 | — | — | 9 |
| T | 0.14 | 9 | 8 | 9 | 7 | — | — | — | 9 | — | — | 9 |
| | 0.07 | 9 | 8 | 9 | 7 | — | — | — | 9 | — | — | 9 |

E = Erythro
E + T = Erythro + Threo
T = Threo
*Average of two or more tests

I claim:

1. A method for the control of undesirable monocotyledonous and dicotyledonous plant species comprising applying to the foliage and stems of said plants or to soil containing seeds or other propagating organs of said plants, a herbicidally effective amount of a compound of formula (I):

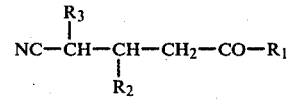

wherein $R_1$ is OH, $OR_4$, $NR_5R_6$ or OM; $R_2$ and $R_3$ each represent a member selected from the group consisting of

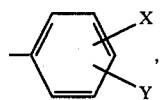

$R_4$ is alkyl $C_1-C_8$, monohaloalkyl $C_1-C_4$, monohaloalkynyl $C_3-C_4$, monohaloalkenyl $C_3-C_4$, alkoxy $C_1-C_4$ alkyl $C_1-C_4$ or hydroxyalkynyl $C_2-C_4$; $R_5$ and $R_6$ each independently represent members selected from the group consisting of H and alkyl $C_1-C_2$; M is an alkali metal, ammonium, $C_1-C_8$ mono or di-alkylammonium or hydroxyethylammonium; and X and Y each independently represent members selected from the group consisting of hydrogen, halogen, alkyl $C_1-C_4$, alkoxy $C_1-C_4$, $OCF_3$, $OCHF_2$, $CF_3$, CN, COOH, $NO_2$, OH, $SCH_3$, $NR_7R_8$, $CH_3SO_2$, and $R_7$ and $R_8$ are each hydrogen or alkyl ($C_1-C_2$).

2. A method according to claim 1 for the control of undesirable plant species wherein said compound is a threo stereoisomer of said formula (I) having a structure selected from the group consisting of:

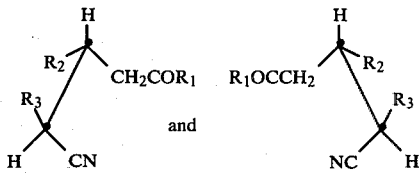

wherein $R_1$ is OH, $OR_4$ or OQ; $R_2$ and $R_3$ each represent a member selected from the group consisting of

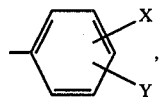

$R_4$ is alkyl $C_1-C_8$, monohaloalkyl $C_1-C_4$, monohaloalkynyl $C_3-C_4$, monohaloalkenyl $C_3-C_4$, alkoxy $C_1-C_4$ alkyl $C_1-C_4$, or hydroxyalkynyl $C_2-C_4$; Q is ammonium, $C_1-C_8$ mono or di-alkylammonium or hydroxyethylammonium, and X and Y each independently represent hydrogen, halogen, alkyl $C_1-C_4$, alkoxy $C_1-C_4$, $OCF_3$, $CF_3$, CN, COOH, $OCHF_2$, $NO_2$, OH, $SCH_3$ or $CH_3SO_2$.

3. A method according to claim 1 wherein said compound is applied to the foliage and stems of said plants or to soil containing seeds or other propagating organs thereof at a rate of between 0.035 and 11.2 kg per hectare.

4. A method according to claim 2 wherein said compound is applied at the rate of from about 0.017 to 4.48 kg per hectare to the foilage and stems of said undesirable plants or to soil containing seeds or other propagating organs of said plants.

5. A method according to claim 1 wherein $R_1$ is OH, $OR_4$ or OM and $R_2$ and $R_3$ are each chlorophenyl or one of $R_2$ and $R_3$ is phenyl and the other is phenyl, chlorophenyl, bromophenyl, chlorofluorophenyl, fluorophenyl, dichlorophenyl, trifluoromethylphenyl, methylphenyl, methoxyphenyl, cyanophenyl or nitrophenyl; $R_4$ is alkyl $C_1-C_8$, chloroethyl or n-butoxyethyl and M is sodium, lithium, ammonium, hydroxyethylammonium or ($C_1-C_8$) mono or di-alkylammonium ($C_1-C_8$).

6. A method according to claim 1 wherein said compound is erythro-threo-3-(m-chlorophenyl)-4-cyano-4-phenylbutyric acid.

7. A method according to claim 1 wherein said compound is erythro-threo-ethyl-4-cyano-3-(2,4-dichlorophenyl)-4-phenylbutyrate.

8. A method according to claim 1 wherein said compound is erythro-threo-4-cyano-4-(3,5-dichlorophenyl)-3-phenylbutyric acid.

9. A method according to claim 1 wherein said compound is erythro-threo-ethyl-3-(3-chloro-4-fluorophenyl)-4-cyano-4-phenylbutyrate.

10. A method according to claim 1 wherein said compound is erythro-threo-4-cyano-3,4-diphenylbutyric acid, dimethylamine salt.

11. A method according to claim 1 wherein said compound is erythro-threo-4-cyano-3,4-diphenylbutyric acid sodium salt.

12. A method according to claim 1 wherein said compound is erythro-threo-ethyl 4-cyano-3-(3,5-dichlorophenyl)-4-phenylbutyrate.

13. A method according to claim 1 wherein said compound is erythro-threo-4-cyano-4-(p-fluorophenyl)-3-phenylbutyric acid.

14. A method according to claim 1 wherein said compound is erythro-threo-ethyl 4-cyano-3-(p-fluorophenyl)-4-phenylbutyrate.

15. A method according to claim 1 wherein said compound is erythro-threo-ethyl 4-(m-chlorophenyl)-4-cyano-3-(2,4-dichlorophenyl)butyrate.

16. A method according to claim 2 wherein $R_1$ is OH, $OCH_3$ or $OC_2H_5$; $R_2$ is phenyl, m-nitrophenyl or p-chlorophenyl and $R_3$ is phenyl, m-chlorophenyl or 3,5-dichlorophenyl.

17. A method according to claim 2 wherein said compound is threo-ethyl 4-(m-chlorophenyl)-4-cyano-3-phenylbutyrate.

18. A method according to claim 2 wherein said compound is threo-4-cyano-3,4-diphenylbutyric acid.

19. A method according to claim 2 wherein said compound is threo-ethyl 4-cyano-3,4-diphenylbutyrate.

20. A method according to claim 2 wherein said compound is threo-ethyl 3-(p-chlorophenyl)-4-cyano-4-phenylbutyrate.

21. A method according to claim 2 wherein said compound is threo-ethyl-3-(m-bromophenyl)-4-cyano-4-phenylbutyrate.

22. A method according to claim 2 wherein said compound is threo-3-(p-chlorophenyl)-4-cyano-4-phenylbutyric acid.

23. A method according to claim 2 wherein said compound is threo-ethyl 4-cyano-4-(3,5-dichlorophenyl)-3-phenylbutyrate.

24. A method according to claim 1 wherein said compound is erythro-threo-4-(m-chlorophenyl)-4-cyano-3-phenylbutyric acid.

25. A method according to claim 2 wherein said compound is erythro-threo-ethyl 3-(p-chlorophenyl)-4-cyano-4-phenylbutyrate.

26. A herbicidal composition comprising a herbicidally effective amount of a compound according to claim 1 having the formula (I):

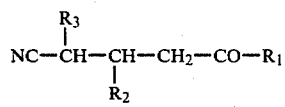

wherein $R_1$ is OH, $OR_4$, $NR_5R_6$ or OM; $R_2$ and $R_3$ each represent a member selected from the group consisting of

$R_4$ is alkyl $C_1$-$C_8$, monohaloalkyl $C_1$-$C_4$, monohaloalkynyl $C_3$-$C_4$, monohaloalkenyl $C_3$-$C_4$, alkoxy $C_1$-$C_4$ alkyl $C_1$-$C_4$ or hydroxyalkynyl $C_2$-$C_4$; $R_5$ and $R_6$ each independently represent members selected from the group consisting of hydrogen and alkyl $C_1$-$C_2$; M is an alkali metal, ammonium, $C_1$-$C_8$ mono or di-alkylammonium or hydroxyethylammonium; and X and Y each independently represent members selected from the group consisting of hydrogen, halogen, alkyl $C_1$-$C_4$, alkoxy $C_1$-$C_4$, $OCF_3$, $OCHF_2$, $CF_3$, CN, COOH, $NO_2$, OH, $SCH_3$, $NR_7R_8$ and $CH_3SO_2$; $R_7$ and $R_8$ are each hydrogen or alkyl ($C_1$-$C_2$) in admixture with an inert, solid, water insoluble diluent.

27. A composition according to claim 26 wherein the solid diluent is selected from the group consisting of silica, kaolin, attapulgite, bentonite, montmorillonite, pumice, talc, fullers earth and diatomaceous earth.

28. A threo stereoisomer of a polysubstituted butanoic acid or ester represented by a compound having a formula selected from the group consisting of:

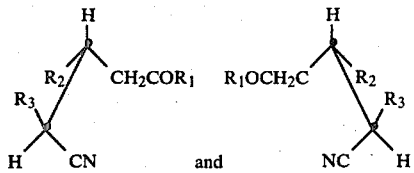

wherein $R_1$ is OH, $OR_4$ or OQ; $R_2$ and $R_3$ each represent members selected from the group consisting of

$R_4$ is alkyl $C_1$-$C_8$, monohaloalkyl $C_1$-$C_4$, monohaloalkenyl $C_3$-$C_4$, monohaloalkynyl $C_3$-$C_4$, alkoxy $C_1$-$C_4$ alkyl $C_1$-$C_4$, and hydroxyalkynyl $C_2$-$C_4$; Q is ammonium, $C_1$-$C_8$ mono or di-alkylammonium or hydroxyethylammonium; and, X and Y each independently represent members selected from the group consisting of hydrogen, halogen, alkyl $C_1$-$C_3$, $OCF_3$, $CF_3$, CN, COOH, $OCH_3$, $NO_2$, OH, $SCH_3$ or $CH_3SO_2$; and provided that when $R_4$ is ethyl at least one of $R_2$ and $R_3$ is other than phenyl.

29. A compound according to claim 28, threo-ethyl 4-cyano-4-(3,5-dichlorophenyl)-3-(m-nitrophenyl)butyrate.

30. A compound according to claim 28, threo-4-cyano-3,4-diphenylbutyric acid;

31. A compound according to claim 28, threo-ethyl 4-(m-chlorophenyl)-4-cyano-3-phenylbutyrate;

32. A compound according to claim 28, threo-ethyl 4-cyano-3-(m-nitrophenyl)-4-phenylbutyrate;

33. A compound according to claim 28, threo-ethyl 3-(p-chlorophenyl)-4-cyano-4-phenylbutyrate.

34. A compound according to claim 28, threo-3-(p-chlorophenyl)-4-cyano-4-phenylbutyric acid.

35. A compound according to claim 28, threo-4-cyano-4-(3,5-dichlorophenyl)-3-phenylbutyric acid.

36. A compound according to claim 28, threo-ethyl 4-cyano-4-(3,5-dichlorophenyl)-3-phenylbutyrate.

37. A compound according to claim 28, threo-octyl 4-cyano-3,4-diphenylbutyrate.

38. A compound according to claim 28, threo-ethyl 4-cyano-3-(m-cyanophenyl)-4-phenylbutyrate.

39. A compound according to claim 28, threo-ethyl 4-cyano-4-phenyl-3-($\alpha,\alpha,\alpha$-trifluoro-m-tolyl)butyrate.

40. A compound according to claim 28, threo-ethyl 3-(p-chlorophenyl)-4-(m-chlorophenyl)-4-cyanobutyrate.

41. A compound according to claim 23, threo-ethyl 3-(m-bromophenyl)-4-cyano-4-phenylbutyrate.

42. A compound according to claim 28, threo-3-(m-chlorophenyl)-4-cyano-4-phenylbutyric acid.

43. A compound according to claim 28, threo-ethyl 4-cyano-3-(3,5-dichlorophenyl)-4-phenylbutyrate.

44. A compound according to claim 28, threo-ethyl 4-cyano-3-(2,4-dichlorophenyl)-4-phenylbutyrate.

45. A compound according to claim 28, threo-ethyl 3-(3-chloro-4-fluorophenyl)-4-cyano-4-phenylbutyrate.

46. A compound according to claim 28, threo-methyl 4-cyano-3,4-diphenylbutyrate.

* * * * *